(12) United States Patent
Brachmann

(10) Patent No.: US 6,911,538 B2
(45) Date of Patent: Jun. 28, 2005

(54) ENGINEERED OPEN READING FRAME FOR P53

(75) Inventor: Rainer K. Brachmann, St. Louis, MO (US)

(73) Assignee: Washington University, St. Louis, MO (US)

( * ) Notice: Subject to any disclaimer, the term of this patent is extended or adjusted under 35 U.S.C. 154(b) by 451 days.

(21) Appl. No.: 10/077,176

(22) Filed: Feb. 19, 2002

(65) Prior Publication Data

US 2003/0175862 A1 Sep. 18, 2003

Related U.S. Application Data

(60) Provisional application No. 60/348,394, filed on Jan. 16, 2002.

(51) Int. Cl.⁷ .............................................. C07H 21/04
(52) U.S. Cl. ..................................... 536/23.1; 536/24.3
(58) Field of Search ............................... 536/23.1, 24.3

(56) References Cited

U.S. PATENT DOCUMENTS

| | | | |
|---|---|---|---|
| 5,830,751 A | 11/1998 | Boeke et al. | |
| 5,840,579 A | 11/1998 | Boeke et al. | |
| 6,114,148 A | * 9/2000 | Seed et al. ................. | 435/91.1 |
| 6,183,964 B1 | 2/2001 | Boeke et al. | |
| 6,277,622 B1 | * 8/2001 | Weiss ...................... | 435/252.3 |

OTHER PUBLICATIONS

Farrell et al. (The EMBO Journal, vol. 10, No. 10, p. 2879–2887, 1991).*
GenBank Accession (X60012, Jun. 23, 1994).*
"Preferred Codons for Selected Species" obtained from http://www.uky.edu/pharmacy/ps/porter/codonusage/preferred_codons.htm, accessed Oct. 14, 2004; copyright 1999, last modified Sep. 28, 2001.*

R. K. Brachmann et al., "Genetic selection of intragenic suppressor mutations that reverse the effect of common p53 cancer mutations", The EMBO Journal, 1998, pp. 1847–1859, vol. 17, no. 7.

* cited by examiner

*Primary Examiner*—Juliet C. Switzer
(74) *Attorney, Agent, or Firm*—Banner & Witcoff, Ltd.

(57) ABSTRACT

The transcription factor and tumor suppressor protein p53 is inactivated in many human cancers. Approximately forty percent of cancers carry large amounts of mutated full-length p53 protein with one of over 900 reported single amino acid changes in the p53 core domain that recognizes p53 DNA binding sites. The ability to restore function to these inactive p53 proteins would dramatically improve cancer therapy. Alternative open reading frames that are more easily engineered encode a wild-type p53. The alternative open reading frames are optimized for codon usage and expression of p53 proteins in *E. coli*, yeast and mammalian cells. The alternative open reading frames may additionally contain mutations that are naturally found in human cancers, substitutions that correspond to polymorphic p53 alleles, or mutations in residues that can be post-translationally modified.

2 Claims, 7 Drawing Sheets

ENGINEERED OPEN READING FRAME FOR P53

This application claims the priority of Application Ser. No. 60/348,394, filed Jan. 16, 2002.

This invention was made with government support under grant number CA 81511 awarded by the National Institutes of Health/National Cancer Institute. The government has certain rights to the invention.

FIELD OF THE INVENTION

The invention is related to the field of cancer therapy. More particularly, it is related to the area of studying the p53 gene and development of therapeutics related to cancers containing p53 mutations.

BACKGROUND OF THE INVENTION p53 inactivation and cancer. The tumor suppressor gene p53 is of central importance for the genetic stability of human cells (Donehower and Bradley, 1993; Haffner and Oren, 1995; Gottlieb and Oren, 1996; Ko and Prives, 1996; Hansen and Oren, 1997; Levine, 1997). The p53 protein is active as a homo-tetramer and exerts its tumor suppressor function mainly as a transcription factor that induces G1 and G2 cell cycle arrest and/or apoptosis (Donehower and Bradley, 1993; Haffner and Oren, 1995; Gottlieb and Oren, 1996; Ko and Prives, 1996; Hansen and Oren, 1997; Levine, 1997; Hermeking et al., 1998). The p53-mediated G1 arrest is its best characterized activity and involves transcriptional activation of the downstream gene $p21^{WAF1/CIP1/SDI1}$ (Haffner and Oren, 1995; Gottlieb and Oren, 1996; Ko and Prives, 1996; Hansen and Oren, 1997; Levine, 1997). Other downstream effector genes for p53-mediated G1 arrest may exist, since $p21^{-/-}$ mouse embryonic fibroblasts do not show complete abrogation of G1 arrest after DNA damage (Brugarolas et al., 1995; Deng et al., 1995). The G2/M block mediated by p53 involves, at least in part, induction of 14-3-3σ (Hermeking et al., 1998).

The mechanisms for apoptosis induction and their relative importance remain less clear at present. In certain settings p53 clearly induces pro-apoptotic genes. These include BAX and Fas/APO1 (Miyashita and Reed, 1995; Owen-Schaub et al., 1995) neither of which, however, is an absolute requirement for p53-induced apoptosis (Knudson et al., 1995; Fuchs et al., 1997; Yin et al., 1997). Recently, many more genes have been identified that are induced directly or indirectly during p53-mediated apoptosis (Polyak et al., 1997; Wu et al., 1997; Yin et al., 1998), but the essential genes for p53-induced apoptosis still have to be determined. Transcriptional repression of anti-apoptotic genes, such as bcl-2, may play a role (Haldar et al., 1994; Miyashita et al., 1994) and other non-transcriptional mechanisms may be important as well (Caelles et al., 1994; Wagner et al., 1994; Haupt et al., 1995; Wang et al., 1996; White, 1996).

Several upstream signals activate p53. These include DNA damage, hypoxia and critically low ribonucleoside triphosphate pools (Kastan et al., 1991; Graeber et al., 1996; Linke et al., 1996). Once activated, p53 induces either cell cycle arrest or apoptosis, depending on several factors such as the amount of DNA damage, cell type and cellular milieu, e.g., presence or absence of growth factors (Donehower and Bradley, 1993; Haffner and Oren, 1995; Gottlieb and Oren, 1996; Ko and Prives, 1996; Hansen and Oren, 1997; Levine, 1997).

Cancer cells show decreased fidelity in replicating their DNA, often resulting in DNA damage, and tumor masses have inadequate neovascularization leading to ribonucleoside triphosphate or oxygen deprivation, all upstream signals that activate p53. In view of p53's capability to induce cell cycle arrest or apoptosis under these conditions it is not surprising that absent or significantly reduced activity of the tumor suppressor protein p53 is a characteristic of more than half of all human cancers (Hollstein et al., 1991; Harris and Hollstein, 1993; Greenblatt et al., 1994). In the majority of cancers, p53 inactivation is caused by missense mutations in one p53 allele, often with concomitant loss-of-heterozygosity (Michalovitz et al., 1991; Vogelstein and Kinzler, 1992; Donehower and Bradley, 1993; Levine, 1997). These mutations affect almost exclusively the core DNA-binding domain of p53 that is responsible for making contacts with p53 DNA-binding sites (Cho et al., 1994), while mutations in the N-terminal transactivation domain or the C-terminal tetramerization domain are extremely rare (FIG. 1) (Beroud and Soussi, 1998; Cariello et al., 1998; Hainaut et al., 1998). Contrary to wild-type p53, p53 cancer mutants have a long half-life and accumulate to high levels in cancer cells (Donehower and Bradley, 1993; Lowe, 1995). This may be explained by their inability to activate the MDM-2 gene (Lane and Hall, 1997), since mdm-2 induces degradation of p53 via the ubiquitin pathway as part of a negative feedback loop (Haupt et al., 1997; Kubbutat et al., 1997). The unusually high frequency of p53 missense mutations in human cancers (as opposed to mutations resulting in truncated proteins) is explained by their dominant-negative effect that depends on the intact C-terminal tetramerization domain. The C-terminus allows p53 cancer mutants to form hetero-tetramers with wild-type p53 (Milner and Medcalf, 1991), thus reducing, or even abrogating, the activity of wild-type p53 protein (Michalovitz et al., 1991; Vogelstein and Kinzler, 1992; Hann, 1995; Brachmann et al., 1996; Ko and Prives, 1996). In addition, there is evidence that at least some of the same missense mutations may confer a gain-of-function (Gottlieb and Oren, 1996; Ko and Prives, 1996; Levine, 1997).

p53 abnormalities and cancer therapy. Considering the activities of the p53 tumor suppressor protein, reconstitution of wild-type p53 activity to cancers would be of large therapeutic benefit, an idea that is supported by several lines of evidence from epidemiological, clinical and basic cancer research (Fisher, 1994; Lowe, 1995; Harris, 1996a).

Several human malignancies that are usually diagnosed at a young age, such as testis cancer, pediatric acute lymphoblastic leukemia and Wilms tumor, can be successfully eradicated even at advanced stages. They all have in common that they carry wild-type p53 (Heimdal et al., 1993; Wada et al., 1993; Malkin et al., 1994). At the same time, subgroups of these malignancies with a poor prognosis, for example the anaplastic variant of Wilms tumor, commonly do carry p53 mutations (Bardeesy et al., 1995). Similarly, tumor types that are often resistant to conventional therapies and difficult to treat at advanced stages, such as lung, prostate, colorectal, breast, head and neck, pancreatic and gastric cancers, show a high frequency of p53 mutations (Hollstein et al., 1991; Fisher, 1994; Lowe, 1995; Harris, 1996a; Beroud and Soussi, 1998; Cariello et al., 1998; Hainaut et al., 1998).

These findings have spurred great interest in exploring p53 as a predictive marker for response to therapy and for overall prognosis. The majority of cancer types have been evaluated to some extent, and the publications are too numerous to be summarized here. As an example, studies in breast, head and neck, lung and ovarian cancers have found a good correlation between p53 abnormalities and poor survival and poor response to therapy (Thor et al., 1992; Allred et al., 1993; Bergh et al., 1995; Rusch et al., 1995; Sauter et al., 1995; Righetti et al., 1996; Bems et al., 1998; Huang et al., 1998). The results are not always unequivocal, as some studies were unable to detect a statistically significant difference between cancers with and without functional p53 (Isola et al., 1992; Elledge et al., 1995). These discrepancies may be due to confounding factors. For example, a cancer with a poor prognosis because of degradation of p53 by overexpressed mdm-2 may be incorrectly scored as a cancer with functional p53 if the mdm-2 status of the cancer is not evaluated. In addition, the sample size of many studies was not large enough to make firm conclusions.

Strong evidence for a central role of p53-mediated apoptosis in cancer therapy is provided by experiments in cell lines with and without functional p53. Comparison of wild-type and p53-deficient thymocytes established that p53 is required for radiation- and etoposide-induced apoptosis (Clarke et al., 1993; Lowe et al., 1993a). Similar experiments in adenovirus E1A transformed mouse embryo fibroblasts showed that apoptosis induced by radiation, 5-fluorouracil, etoposide and adriamycin also depends on functional p53 in these cells (Lowe et al., 1993b). These studies were extended into a mouse model where again only tumors with functional p53 showed good treatment responses to radiation and adriamycin, while p53-negative tumors were highly resistant to therapy and showed little evidence of apoptosis (Lowe et al., 1994). Results of the Developmental Therapeutics Program of the NCI impressively and independently confirmed these findings. An analysis of the cytostatic and cytotoxic effects of 123 compounds on 60 different human cancer cell lines showed a very good correlation between p53 mutations and resistance to many commonly used chemotherapeutic agents (O'Connor et al., 1997; Weinstein et al., 1997). All these data do not necessarily indicate that functional p53 is absolutely essential for chemotherapy-induced apoptosis. In fact, chemotherapy drugs can kill cancer cells through p53-independent mechanisms (Kaufmann, 1989; Strasser et al., 1994; Bracey et al., 1995). The sum of the evidence, however, suggests that cancer agents are significantly more effective in the presence of p53 (Fisher, 1994; Lowe, 1995; Harris, 1996a).

Based on the discussed studies and the general knowledge about p53, p53 and its pathways have been recognized as a prime target for developing new cancer therapies (Fisher, 1994; Gibbs and Oliff, 1994; Kinzler and Vogelstein, 1994; Lowe, 1995; Milner, 1995; Harris, 1996a). In particular, the high frequency of p53 mutations in cancers makes therapeutic strategies for restoring this tumor suppressor pathway highly desirable since a large number of patients could potentially benefit. It has been estimated that every year approximately 330,000 patients in the United States and 2.4 million patients worldwide are diagnosed with cancers that contain p53 mutations (Harris, 1996a, 1996b).

Strategies to partially or completely restore wild-type p53 function to cancer cells. Restoration of wild-type p53 activity to cancer cells is the most direct way of making cancer cells more susceptible to apoptosis and can be pursued in two ways. The first strategy is to reintroduce wild-type p53, perhaps by gene therapy (Roth et al., 1996; Barinaga, 1997; Nielsen and Maneval, 1998), and does not rely on the p53 status of a given cancer. The current major challenge is efficient and selective targeting of wild-type p53 expression constructs to the cancerous cells (Nielsen and Maneval, 1998). A major drawback of this approach is that it may be less effective for cancers with vast amounts of a dominant-negative p53 cancer mutant. This strategy would be greatly aided by the availability of p53 proteins that are resistant to the dominant-negative effects of p53 cancer mutants and that are superior to wild-type p53 in inducing apoptosis, classes of p53 proteins that to date have not been described.

The second strategy is only possible because of the unique pattern of p53 missense mutations in human cancers and aims at therapeutically exploiting the abundant p53 mutant protein found in many cancers. Since the resulting p53 cancer mutants are full-length proteins each with a structurally altered core domain, but an intact transactivation domain and an intact C-terminal tetramerization domain, one could restore wild-type activity to the p53 cancer mutants in these tumors (Gibbs and Oliff, 1994; Lowe, 1995; Milner, 1995; Harris, 1996a). This can be achieved in at least two ways. One attempt has been to interfere with the extreme C-terminal autoregulatory domain of p53 by using antibodies (Halazonetis and Kandil, 1993; Hupp et al., 1993; Abarzua et al., 1995; Niewolik et al., 1995) or peptides spanning part of this region (Hupp et al., 1995; Abarzua et al., 1996; Selivanova et al., 1997). This strategy presumably activates p53 cancer mutants by blocking the ability of the very C-terminus to fold back onto and inhibit the p53 core domain. It could succeed with p53 cancer mutants that retain residual activity and which only require additional activation to exceed the threshold required for biological effects. However, antibodies and peptides clearly cannot be delivered efficiently to cancer cells in patients (Selivanova et al., 1997). Small molecule compounds with similar effects could overcome this problem, but their design is currently not feasible since the exact structural basis of this negative autoregulation and of its neutralization by antibodies or peptides is not known due to lack of a crystal structure for the full-length p53 protein (Ko and Prives, 1996; Selivanova et al., 1997). In addition, this approach may activate mutant and wild-type p53 proteins indiscriminately, thus possibly causing significant side effects due to inappropriate wild-type p53-induced apoptosis in normal tissues.

A more direct approach is to revert the effects of tumorigenic mutations on the structure and function of the p53 core domain itself by means of small molecules. This strategy is preferable since it is predicted to selectively stabilize p53 cancer mutants. It also holds the promise of restoring function to completely inactive p53 cancer mutants. Restoring the normal configuration to a p53 cancer mutant is considered more challenging than inhibiting the function of a protein by small molecules (Gibbs and Oliff, 1994). However, there are examples: small molecule compounds that bind the central cavity of the hemoglobin tetramer can act as allosteric effectors and stabilize the T state of hemoglobin over the R state (Abraham et al., 1992); and small molecule compounds that stabilize the transthyretin tetramer against dissociation can prevent amyloid fibril formation in vitro (Miroy et al., 1996). Furthermore, the technology of structure-based drug design is steadily advancing so that this challenge may be met (Bohacek et al., 1996; Marrone et al., 1997).

p53 mutations and the p53 core DNA-binding domain. These considerations make it clear that a detailed understanding of the structural consequences of p53 cancer mutations on the p53 core domain is needed. More significantly, stabilizing mechanisms must be identified that can override the deleterious structural effects of p53 cancer mutations.

The crystal structure of the wild-type p53 core domain has given enormous insight into how p53 interacts with its DNA-binding sites (Cho et al., 1994). The structures of the C-terminal tetramerization domain and of the N-terminal transactivation domain (complexed to mdm-2) have been determined as well (Clore et al., 1994; Jeffrey et al., 1995; Kussie et al., 1996). The structure of the full-length protein as a homo-tetramer, however, is solely based on computer modeling (Jeffrey et al., 1995) and suggests that the core domain functions as a separate entity that is connected to the other domains through flexible linkers. The core domain spans 191 amino acids and consists of a β sandwich that serves as the scaffold for two large loops (termed L2 and L3) and a loop-sheet-helix motif. The loops and the loop-sheet-helix motif form the DNA-binding surface of p53 and provide contacts to the DNA backbone and the edges of the bases (FIG. 1A). This structural organization was considered unique until the recent discovery of p73 made it clear that p53 is actually part of a family of transcription factors (Jost et al., 1997; Kaghad et al., 1997). The vast majority of tumor-derived p53 missense mutations map to this core domain (FIG. 1B) and invariably result in the reduction or loss of DNA-binding. These cancer mutations are predicted to fall into two classes; one class of mutations maps to DNA-contacting residues and eliminates p53-DNA contacts (functional mutations); the other, larger class of mutations probably affects the structural integrity of the DNA-binding domain (structural mutations). These structural defects may range from small structural shifts to the global destabilization and unfolding of the p53 core domain. The most frequent p53 cancer mutations affect amino acids that are part of important structures of the p53 core domain, such as the L3 loop and the loop-sheet-helix motif that provide DNA contacts. However, the high frequency of a mutation does not predict how deleterious its effects on the structural integrity of the core domain are, since the frequency of these mutations is also determined by exogenous carcinogens and endogenous biological processes (Donehower and Bradley, 1993; Greenblatt et al., 1994).

To date, our understanding of the structural consequences of p53 cancer mutations is limited to predictions using the structure of the wild-type p53 core domain, biochemical data (Cho et al., 1994) and experiments with monoclonal antibodies that recognize areas of the p53 core domain that are not accessible in the correctly folded state (Donehower and Bradley, 1993; Gottlieb and Oren, 1996; Levine, 1997). Similarly, very little is known about how the effects of cancer mutations can be overcome.

There is a need in the art for the identification of small molecules and proteins that will restore function to mutant p53 proteins. Such small molecules and proteins will increase the ability of mutant p53 to induce cell cycle arrest and/or apoptosis. There is also a need in the art for reagents to aid in the development and identification of such p53 suppressors.

BRIEF SUMMARY OF THE INVENTION

These and other objects of the invention are achieved by providing one or more of the embodiments described below. In one embodiment of the invention a non-naturally occurring nucleic acid molecule encoding wild-type human p53 protein is provided. The p53 protein has a sequence shown in SEQ ID NOs: 54–57. The nucleic acid employs a plurality of alternative codons to those present in naturally occurring wild-type human p53 coding sequence as shown in SEQ ID NO: 58–61. At least a portion of the alternative codons provides additional unique restriction sites to the human p53 coding sequence.

In another embodiment of the invention a non-naturally occurring nucleic acid molecule is provided. The nucleic acid molecule employs a plurality of alternative codons to those present in naturally occurring wild-type human p53 coding sequence. The alternative codons do not cause amino acid changes from wild-type human p53. At least a portion of the alternative codons provides additional unique restriction sites to the human p53 coding sequence. The nucleic acid further comprises a p53 mutation of a human cancer.

In a further embodiment of the invention a non-naturally occurring nucleic acid molecule is provided. The nucleic acid molecule employs a plurality of alternative codons to those present in naturally occurring wild-type human p53 coding sequence. The alternative codons cause no amino acid changes from wild-type p53. At least a portion of the alternative codons provides additional unique restriction sites to the human p53 coding sequence. The nucleic acid further contains a mutation in a codon for a residue that is post-translationally modified in wild-type p53. The mutation prevents post-translational modification of the residue.

These and other embodiments of the invention, which will be apparent to those of skill in the art, provide the art with reagents to develop p53 suppressors for the treatment of cancer. Vectors that contain these reagents exhibit better expression in host cells and are more amenable to manipulation to arrive at p53 suppressors for treatment of cancer. Gene therapy for treatment of cancers with p53 mutations using these nucleic acids is also provided.

BRIEF DESCRIPTION OF THE DRAWINGS

FIG. 1A shows the structure of the p53 core domain. A β sandwich serves as the scaffold for two large loops (termed L2 and L3) and a loop-sheet-helix motif. The loops and the loop-sheet-helix motif form the DNA binding surface of p53. The L3 loop makes DNA contacts in the minor groove, while the H2 α helix and the L1 loop of the loop-sheet-helix motif make contacts in the major groove. The L2 and L3 loops provide stability to the DNA-binding surface through interactions with a Zn atom (Cho et al., 1994.) FIG. 1B is a map of tumor-derived p53 core domain mutations against a schematic p53 protein. The vast majority of tumor-derived p53 missense mutations map to the p53 core domain as shown by the mutation histogram superimposed on the schematic p53 protein. Six "hot spot" codons are preferentially mutated due to exogenous carcinogens and endogenous biological processes. Mutations in the N-terminal transactivation and the C-terminal tetramerization domain are exceedingly rare. The white box in the very C-terminus indicates the location of the autoregulatory domain.

FIG. 2A is a comparison of the p53 open reading frame before and after cloning to introduce multiple restriction sites by silent mutagenesis. Before cloning of the new open reading frame, suppressor mutations with the most frequent p53 cancer mutations required a significant amount of subcloning. FIG. 2B shows that the new pTW500 expression plasmid (designer-p53 gene) and pRB16 (native p53 gene) have the same phenotype, Ura$^+$Foa$^S$, in a yeast strain with the reporter gene 1cUAS53::URA3. FIG. 2C shows that pTW500 and pRB16 have equal growth in SC-Ura media. A control strain with the reporter gene alone does not grow, while a strain with the URA3 gene shows superior growth. FIG. 2D shows that the new p53 expression plasmid pTW500 leads to similar p53 protein levels in yeast, as compared to the previously used pRB16.

DETAILED DESCRIPTION OF THE INVENTION

Figure 1A:
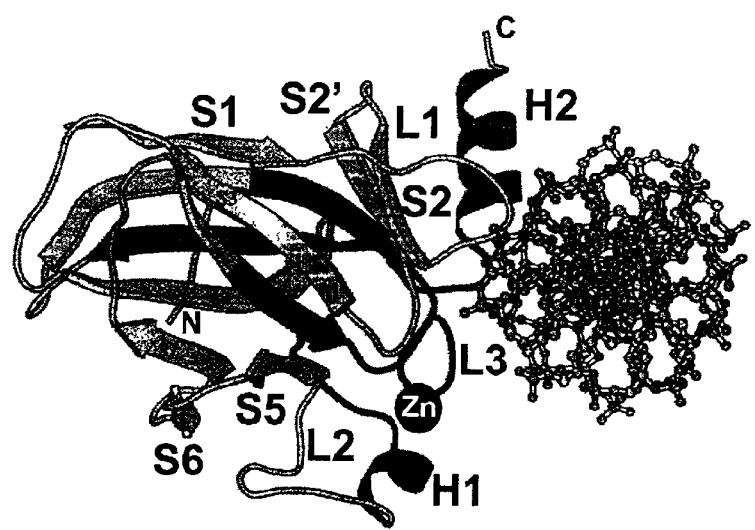
FIGS. 1A and 1B. Structure of the p53 core DNA-binding domain and pattern of missense mutations within the core domain.
Figure 1A:
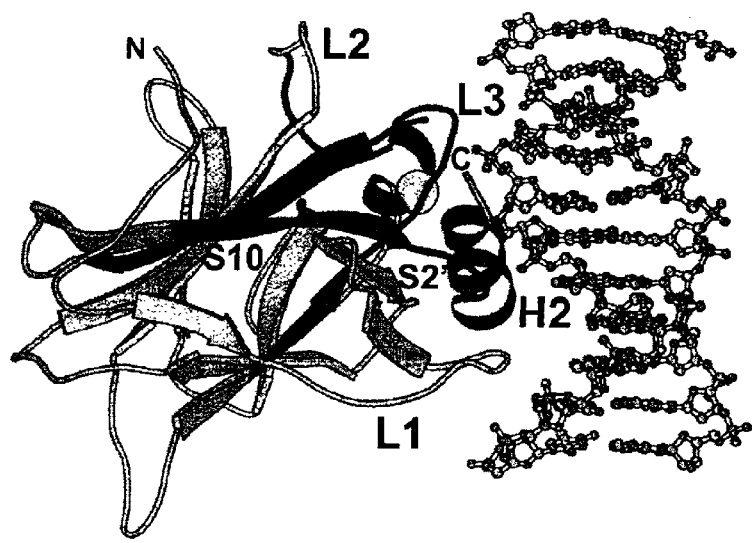
Figure 1B:
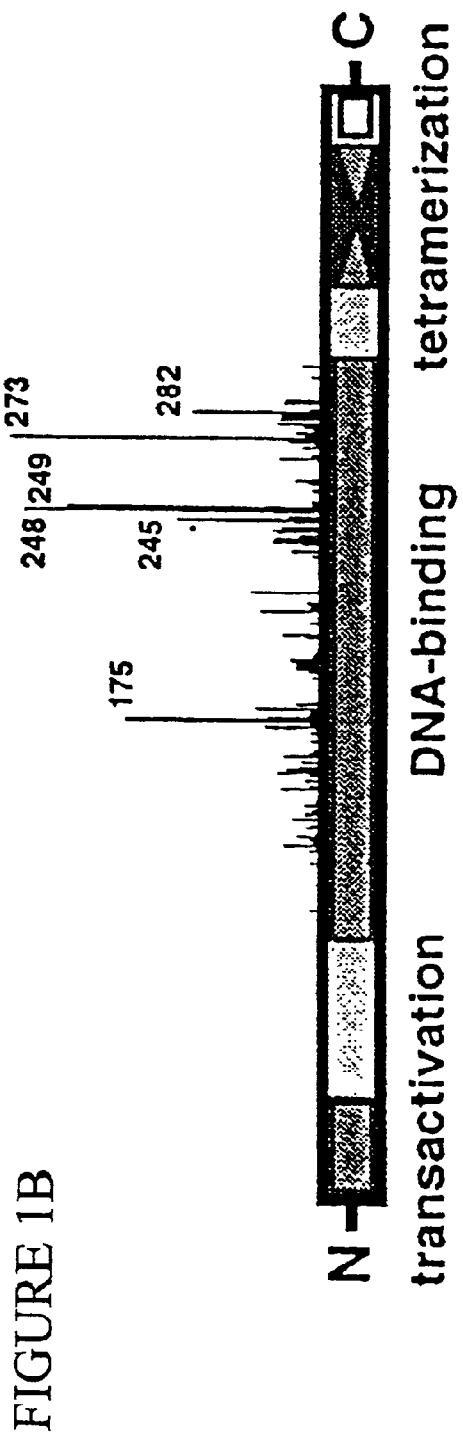

The inventor has discovered alternative p53 open reading frames with amino acid sequences identical to a wild-type p53 amino acid sequence. The open reading frames optimize cloning with and expression of p53 nucleotide sequences. The p53 nucleotide sequences can be delivered by gene therapy vectors to human cancers containing p53 mutations to optimize expression of wild-type p53. P53 suppressor mutations can be readily cloned into the alternative p53 open reading frames. Gene therapy vectors containing these sequences can be delivered to human cells containing a mutation in p53.

A naturally occurring wild-type human p53 coding sequence may be any wild-type human p53 that is naturally found in humans and is characterized by wild-type p53 activity. Examples of such polymorphic human p53 sequences can be found at the www host server, iarc.fr domain name, p53/Polymorphism.html#Table directory. Preferably the human p53 coding sequence has the sequence of GenBank Accession number NP_000537 (SEQ ID NO: 58). Common polymorphisms include GAT at codon 21, CCA at codon 36, CGG at codon 213, TCG at codon 47, and CCC at codon 72. One or more polymorphisms can be found in a single coding sequence. Most preferably the wild-type human p53 coding sequence is any of sequences SEQ ID NO: 58–61.

Similarly, the wild-type human p53 protein sequence is the sequence of any p53 protein that exhibits wild-type human p53 activity. Preferably the p53 sequence is the sequence found at GenBank Accession number NP_000537 (SEQ ID NO: 55). If the wild-type human p53 sequence is the sequence of a different polymorphic form of p53, preferably it has a Ser at residue 47 (SEQ ID NO: 56) or Pro at residue 72 (SEQ ID NO: 54), or both (SEQ ID NO: 57).

Non-naturally occurring alternative codons may be preferable for use in mammalian cells, yeast cells, bacterial cells, or any combination thereof. The alternative codons may also be more preferred for use in Drosophila cells. Any number of alternative codons may be introduced into the sequence of the wild-type human p53 coding sequence. Preferably at least 2, at least 5, at least 10, at least 15, at least 20, at least 25, at least 30, at least 40, at least 50, at least 75, at least 100, at least 120, at least 140, or at least 150 alternative codons may be introduced. The codons do not change the amino acid sequence of the p53 protein. The alternative codons can be introduced for any known purpose in the art. The alternative codons may be introduced to insert a new restriction enzyme cleavage site into the open reading frame, to delete a restriction enzyme cleavage site from the open reading frame, to produce a polymorphic p53 found in the human population that does not change the p53 amino acid sequence, or to optimize expression of the p53 nucleic acids in a particular organism.

At least a portion of the alternative codons provides additional unique restriction sites to the human p53 sequence. A portion is any percentage of the total number of alternative codons introduced into the p53 sequence. The portion may be at least 5%, 10%, 15%, 20%, 25%, 30%, 40%, 50%, 60%, 75%, 80%, 90%, 95%, or 99% of all the alternative codons introduced into the p53 encoding nucleic acids. The non-naturally occurring p53 nucleic acids may contain at least 1, at least 5, at least 10, at least 15, at least 20, at least 25, at least 30, at least 40, at least 50, at least 75, or at least 100 additional restriction sites as a result of introducing alternative codons.

Preferably the nucleic acid will have the nucleotide sequence of one of the three artificial p53 open reading frames as shown in SEQ ID NO: 1–3. The nucleic acid sequence may also contain a polymorphism common in the human population. SEQ ID NO: 62–64 are polymorphic variants of SEQ ID NO: 1. SEQ ID NO: 65–67 are polymorphic variants of SEQ ID NO: 2. SEQ ID NO: 68–70 are polymorphic variants of SEQ ID NO: 3.

The nucleic acids of the invention can be deoxyribonucleic acids (DNA) or ribonucleic acid (RNA) molecules such as mRNA. The nucleic acids can be linear nucleic acids or they can be cloned into any suitable vector. Suitable vectors include plasmids, artificial chromosomes, or viral genomes. Plasmids are well known in the art and include plasmids that are suitable for introduction of the p53 gene into bacterial, yeast, mammalian, insect, or other eukaryotic cells or organisms. The plasmids may be available through a commercial vendor, or may be noncommercial plasmids, or derivatives thereof. Artificial chromosomes are preferably the artificial chromosomes of humans, yeast, or bacteria. Viral vectors are also well known in the art. Preferably the viral genome is the genome of an adeno-associated virus, adenovirus, herpes virus, retrovirus, or vaccinia virus. Viral vectors such as Baculovirus may also be used for subsequent use in insect cells.

p53-encoding nucleic acids can be introduced into a vector by any technique known for this purpose. Several nonlimiting examples of such techniques include restriction enzyme digestion of the p53 nucleic acids and direct ligation into a vector, or PCR amplification of the p53 nucleic acids and subsequent cloning by restriction enzyme digestion and ligation into a vector. Other techniques for cloning the p53 nucleic acids into a vector can be found in Sambrook, J., Fritsch, E. and Maniatis, T., *Molecular Cloning: A Laboratory Manual* Second Edition. Cold Spring Harbor Press, Cold Spring Harbor, N.Y., and Ausubel, F. M. et al., *Current Protocols in Molecular Biology*. Wiley, Interscience New York (1987). Methods of mutagenesis of the p53 nucleic acids can also be found in these references.

It is also contemplated that the nucleic acid encoding an alternative p53 open reading frame can further comprise regulatory sequences that enhance the expression of the p53 gene. Promoters and enhancers are well known to those of skill in the art. Several nonlimiting examples include constitutive promoters such as the strong promoters of cytomegalovirus, SV40, or Rous sarcoma virus. Promoters can also be inducible promoters that are induced by drugs like tetracycline, or tissue specific promoters. Tissue specific promoters include the albumin promoter for expression in the liver, the myosin light chain 1 promoter for expression in muscle and endothelial cells, the surfactant protein A or keratin 18 for expression in lung, and the prostate specific antigen (PSA) promoter, the probasin (PB) promoter, or the prostate specific membrane antigen promoter for expression in prostate. Tumor specific promoters can also be used.

Tumor specific promoters include the tyrosine kinase promoter for B16 melanomas, the DF3/MUC1 promoters for certain breast cancers, and the a fetoprotein promoter of hepatomas. Enhancers may be used from viruses such as Rous sarcoma virus, hepatitis B virus, or simian virus-40 can be used. Enhancers from the cyclic AMP response element, serum response element, nuclear factor kappa b element, activator protein 1, or serum response factor may be used as well. Any enhancers known in the art can be used.

The nucleic acids encoding human p53 may further comprise a selectable marker gene. The selectable marker gene allows easy detection of the transfer of the p53 nucleic acids into a suitable host cell. Selectable marker genes may be genes that confer resistance to a toxic agent such as an antibiotic. Antibiotic resistance genes include those for ampicillin, tetracycline, puromycin, neomycin, and hygromycin. The selectable marker gene may confer resistance to a toxic agent; such genes include the adenine deaminase, aminoglycoside phosphotransferase, dehydrofolate reductase or xanthine-guanine phosphoribosyltransferase gene. The selectable marker gene may alternatively be a reporter gene whose expression is monitored readily by assay. Several nonlimiting examples of such reporter genes are chloramphenicol transacetylase, firefly luciferase, beta galactosidase, secreted alkaline phosphatase, and beta glucuronidase. The marker gene can also be a gene that allows growth of a cell on medium lacking an amino acid. An example of a selectable marker gene of yeast is the URA3 gene. Counterselectable genes can also be used with yeast such as LYS2, LYS5, CAN1, MET2, MET15, and GAL1. Other such marker genes are known in the art.

The nucleic acids of the invention can also be isolated or in a cell. The cells can be of any type including mammalian cells, insect cells, *Drosophila* cells, yeast cells or bacterial cells. If the cells are mammalian cells, they can be the cells of any species including humans, mice, monkeys, pigs, rats, cows, horses, cats, or dogs. The mammalian cells can further be manipulated to knock out one or both endogenous copies of the cell's p53 genes encoded in its cellular DNA, thus allowing study of the alternative human p53 nucleic acids alone in the cells.

The mammalian cells can be in the body of a mammal or may be in in vitro culture. If the cells are in culture, the cells may be primary cells or may be a stable cell line. The cells may also contain a different wild type p53 gene or may have a p53 gene encoding a p53 mutation that has been identified as being associated with a human cancer, a p53 mutation that has not yet been associated with a human cancer, or a p53 mutation that is not associated with a human cancer. The cells may also be tumor cells that may or may not contain a mutant p53 gene. If the cells are in the body of a mammal the non-naturally occurring p53 nucleic acids can be introduced as gene therapy to supply p53 activity or additional p53 activity to the cells.

The human p53 nucleic acids may be introduced into cells by any means known in the art. The nucleic acids may be inserted into the cells by direct transfer, by microinjecting the nucleic acids into the cells. The nucleic acids may also be complexed in a lipid preparation such as liposomes, or coacervated with a polymeric cation. The nucleic acids may alternatively be transferred into cells by electroporation, using DEAE dextran or calcium phosphate. The human p53 nucleic acids may further be transferred into cells using viruses with suitable characteristics for entry into the cells. The transfer of the p53 nucleic acids into the cells may achieve stable or transient transfection.

The non-naturally occurring p53 nucleic acids may be introduced into cells for expression and purification of p53 proteins. The purified human p53 protein may be used for crystallographic studies or for in vitro assays. Alternatively, the human p53 protein expressed from the non-naturally occurring nucleic acids may be assayed for activity in the cells. Yeast functional assays can be performed with the p53 expressed from the non-naturally occurring nucleic acids introduced into yeast (Brachmann et al., 1996; Vidal et al., 1996). Similarly mammalian cell assays have been developed for the study of p53 function. (Lowe et al., 1993b.)

The non-naturally occurring nucleic acid molecule may additionally contain a p53 mutation found in a human cancer. The mutation may be any p53 mutation found in a human cancer. Human cancers containing p53 mutations include tumors of the digestive organs, respiratory system, breast, female genital organs, head and neck, hematopoeitic system, skin, brain, bladder, male genital organs, soft tissues, bone and others. Mutations of human p53 found in cancer include, but are not limited to: Lys132Arg; Cys135Tyr; Cys141Tyr; Pro151Ser; Gly154Val; Val157Phe; Arg158His; Arg158Leu; Ala161Thr; Tyr163Cys; Val173Leu; Val173Met; Arg175His; Cys176Phe; Cys176Tyr; His179Arg; His179Tyr; Ile195Thr; Tyr205Cys; His214Arg; Tyr220Cys; Tyr234Cys; Met237Ile; Cys238Tyr; Ser241Phe; Cys242Phe; Gly245Asp; Gly245Cys; Gly245Ser; Gly245Val; Arg248Gln; Arg248Leu; Arg248Trp; Arg249Met; Arg249Ser; Gly266Arg; Gly266Glu; Val272Met; Arg273Cys; Arg273His; Arg273Leu; Cys275Tyr; Pro278Leu; Pro278Ser; Arg280Lys; Arg280Thr; Asp281Glu; Arg282Trp; Glu285Lys; and Glu286Lys. Preferably the non-naturally occurring nucleic acid molecule containing a mutation found in a human cancer has a nucleotide sequence shown in one of SEQ ID NO: 4–53. It is also contemplated that the nucleic acid additionally contains a suppressor mutation of the p53 mutation that is found in human cancer.

Alternatively a non-naturally occurring nucleic acid molecule may contain a mutation in a codon for a residue that is post-translationally modified in wild-type p53. The mutation prevents posttranslational modification of the residue. The posttranslational modification may be phosphorylation, acetylation, sumoylation, or ubiquitylation.

The residue modified by posttranslational modification may be any residue. If the posttranslational modification is phosphorylation, the residue modified may be any serine, threonine, or tyrosine. Preferably the residue modified is a serine at residue 6, 9, 15, 20, 33, 37, 46, 315, 371, 376, 378, or 392, or the threonine at residue 18 or 81. If the residue is modified by acetylation/deacetylation the residue is preferably a lysine at residue 320, 370, 372, 373, 381, or 382. If the residue is modified by sumoylation/desumoylation the residue is preferably the lysine at residue 386.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

A new p53 open reading frame for identification and evaluation of intragenic suppressor mutations of the most common p53 cancer mutations. Our previous study clearly established that various mechanisms for stabilizing the p53 core domain exist; and it is very likely that additional ones are waiting to be discovered (Brachmann et al., 1998). In light of the discovered p53 suppressor mutations and the need for a comprehensive analysis for the most common p53 cancer mutations, we have designed a much-improved strategy that will require more initial effort, but dramatically streamline future analyses. The design is based on several shortcomings that we encountered and includes the synthesis of a new p53 ORF with multiple restriction sites, as well as specific codon choices for p53 cancer mutations to allow for easy secondary screens.

Figure 2A:
FIGS. 2A, 2B, 2C, and 2D show the design and characterization of a new p53 open reading frame.
Figure 2A:
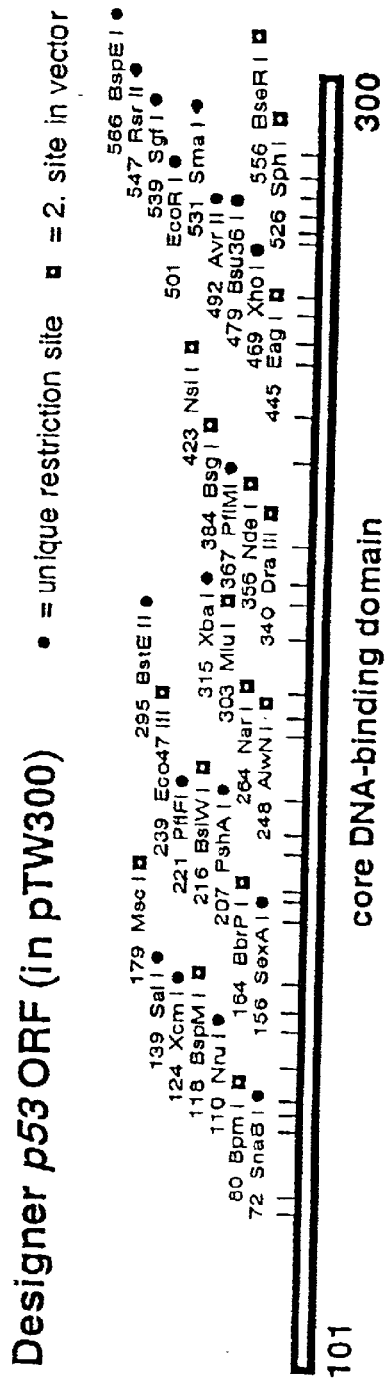

Once we had isolated the suppressor mutations in our prior study, we were very interested in establishing whether these mutations would be able to suppress other cancer mutations. This was fairly easily achieved for mutations such as T123A and T123P yet very cumbersome for N239Y, S240N and N268D due to the scarcity of naturally present restriction sites. We therefore synthesized an entirely new p53 ORF that includes a multitude of unique restriction sites or sites with one additional site in the vector. The introduction of restriction sites by silent mutagenesis was performed using the program WebCutter 2.0 (http file type, www host server, firstmarket.com domain name, cutter/cut2.html directory) and the result is shown in FIG. 2A.

The new ORF was assembled from four fragments that were 379, 249, 257 and 325 base pairs long. Between 3 and 8 clones were sequenced for each of the p53 ORF fragments. This identified clones without mutations for 2 of the 4 fragments. The third fragment could be constructed by combining the areas of two clones without mutations. The fourth fragment was constructed by repairing a single mutation with oligonucleotides. After assembling the entire new p53 ORF with the ADH1-promoter and CYC1-terminator in pRS413 (CEN/HIS3), we compared the new pTW500 with the previously used p53 expression plasmid pRB16 (FIG. 2).

Figure 2B:
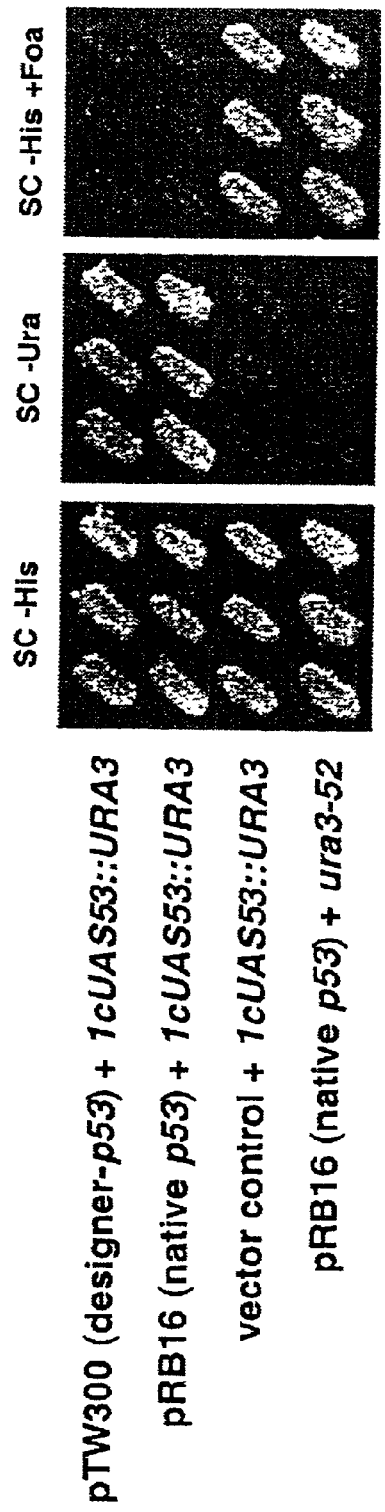

Both p53 expression plasmids showed the same phenotype in the presence of the p53-responsive URA3 reporter gene 1cUAS53::URA3 (FIG. 2B). Four independent transformants were Ura$^+$Foa$^S$, while controls lacking either a p53 expression plasmid or the reporter gene had the opposite phenotype, Ura$^-$Foa$^R$. All strains grew on SC-His plates, indicating the presence of the plasmid with the marker gene HIS3.

Figure 2C:
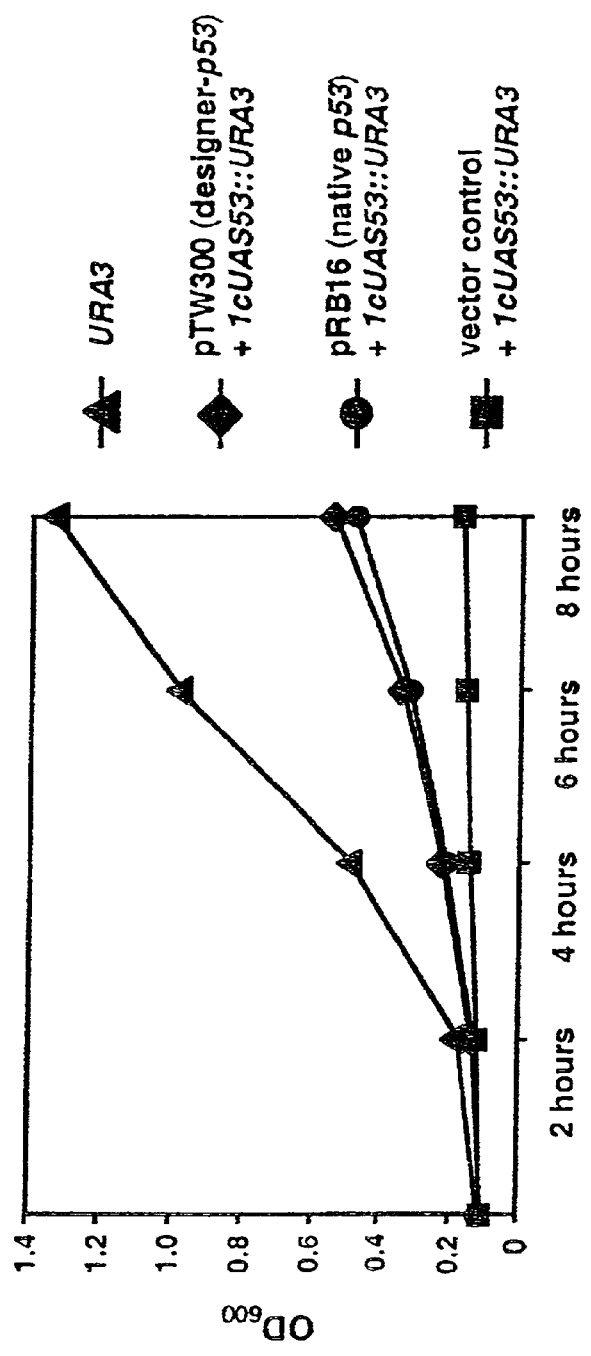
Figure 2D:
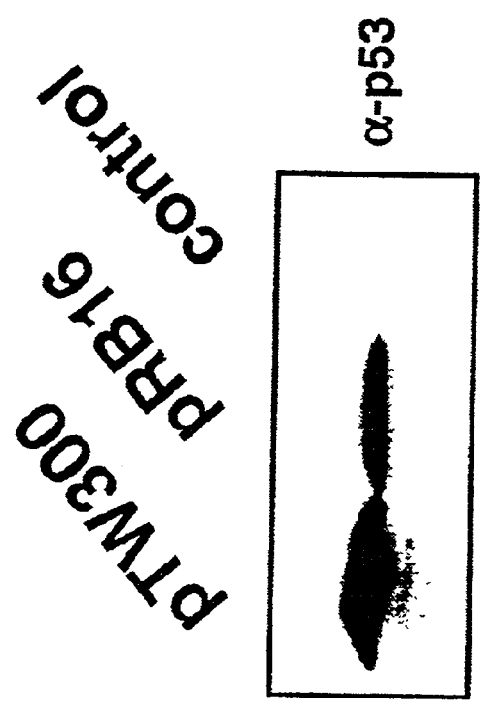

Comparison of the growth rates in SC-Ura media confirmed the results of the plating assays: both plasmids lead to the expression of similar amounts of p53 protein (FIG. 2C). Western Blot analysis using a monoclonal anti-p53 antibody showed that pTW500 indeed leads to p53 protein levels that are similar to and maybe slightly higher than those with pRB 16 (FIG. 2D).

This new p53 ORF is also optimized as much as possible for the preferential codon usage of E. coli, yeast and mammalian cells (Zhang et al., 1991; Wada et al., 1992). To make diagnostic restriction digestions easier to interpret, we also destroyed a variety of restriction sites.

Example 2

Figure 3:
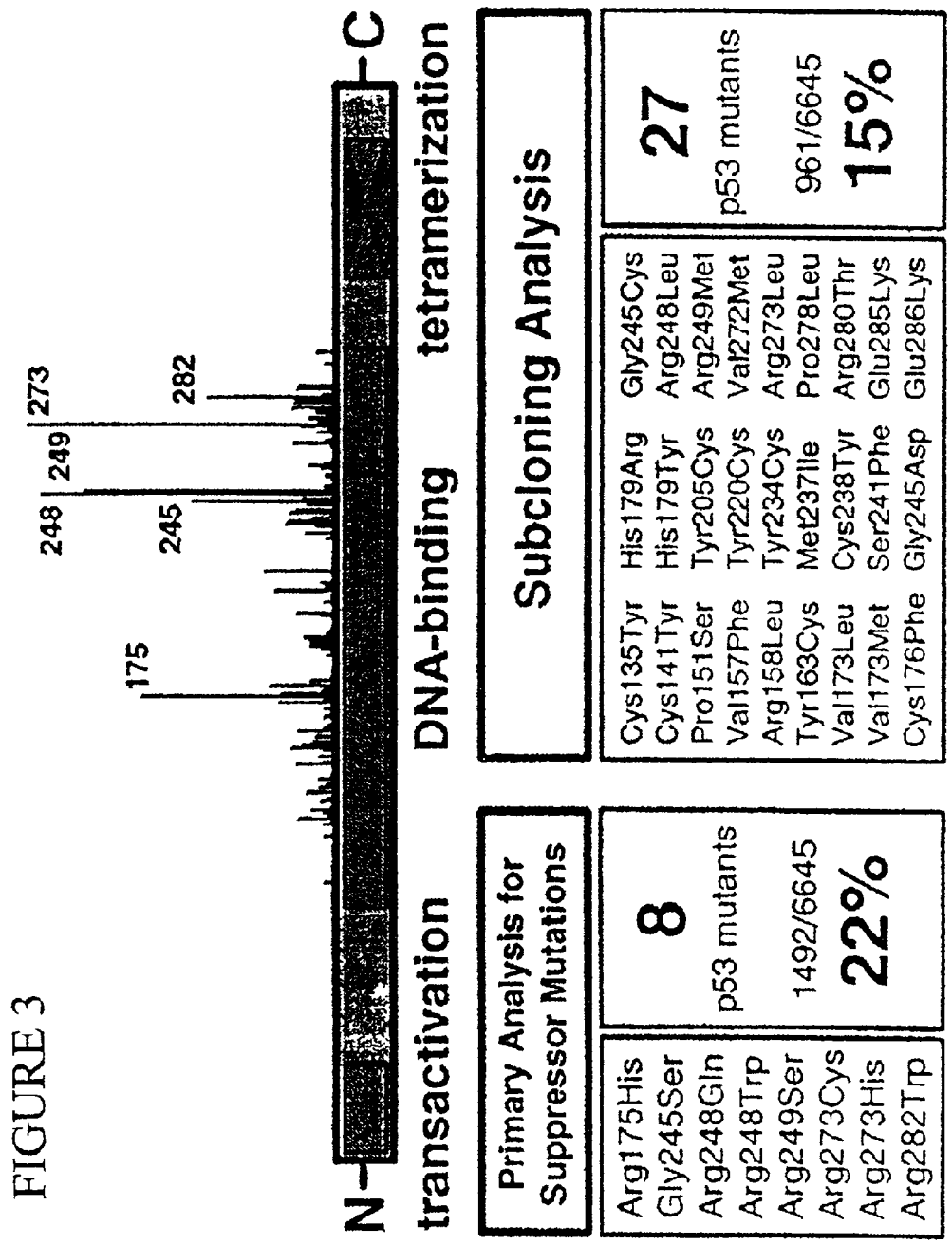
FIG. 3 shows the p53 cancer mutation to be analyzed. The p53 cancer mutations were chosen by their relative frequency in human cancer. All eight cancer mutations that will be used for the search of suppressor mutations are located at "hot spot" codons, codons that have a particularly high frequency of mutations. The first set and the second set of mutations (chosen for the subcloning analysis) comprise approximately 37% of all human cancers with p53 mutations. This is estimated to correspond to 123,000 cancer patients per year in the United States and 890,000 cancer patients worldwide (Harris, 1996a, 1996b.)

Construction of expression cassettes for the most common mutated p53 proteins in humans. A comprehensive analysis is needed to better understand the structural dynamics of the p53 core domain and to potentially find suppressor mutations that have a universal effect. We chose to study the 50 most frequent p53 cancer mutations. Based on several international databases for p53 cancer mutations (Beroud and Soussi, 1998; Cariello et al., 1998; Hainaut et al., 1998), we initially selected a total of eight mutations (FIG. 3). Each of these cancer mutations represents between 1.6% and 4.2% of all human cancers with p53 mutations, totaling 22% (estimated to represent 73,000 cancer patients per year in the United States and 530,000 cancer patients worldwide), (Harris, 1996a, 1996b). Besides their high frequency, these eight cancer mutations also well represent the most important structural motifs of the p53 core domain (L2 loop: codon 175, L3 loop: codons 245, 248 and 249, loop-sheet-helix motif: codons 273 and 282).

We further chose 27 mutations to examine in this final evaluation (FIG. 3). Each cancer mutation in the second set accounts for 0.04 to 1.1% of reported p53 mutations, totaling 15% of all human cancers with p53 mutations (estimated to represent 50,000 cancer patients per year in the United States and 360,000 cancer patients worldwide), (Harris, 1996a, 1996b). This second set reflects many different mechanisms of destabilizing the p53 core domain since the mutations locate to different structural motifs (β sandwich: 8; loop-sheet-helix motif: 7; L2 loop: 5; L3 loop: 7).

Example 3

Identification of suppressor mutations for the most common p53 cancer mutations. New suppressor mutations have been isolated in the new p53 ORF of plasmid pTW500. In order to isolate the new suppressor mutations alone, they will be subcloned into pTW500 and into the pCMVneo-based mammalian expression plasmid for p53 (See Example 1). All subcloning steps will be confirmed either by sequencing or by verifying the loss or gain of a unique restriction site.

Materials and Methods

Transcriptional activity of wild-type p53 in yeast. This assay scores for the transcriptional activity of wild-type p53 and uses an artificial reporter gene, 1cUAS53::URA3, with a synthetic consensus p53 DNA-binding site upstream of URA3 (Brachmann et al., 1996; Vidal et al., 1996). Human p53 is expressed from a yeast CEN expression plasmid under the control of the constitutive promoter ADH1. This p53 yeast assay is unique in that it not only allows selection for, but also against functional p53 (Brachmann and Boeke, 1997). Therefore, it can quickly classify any p53 protein for its activity: p53 proteins with wild-type p53 activity induce URA43 expression which enables the yeast reporter strain to survive on plates without Uracil (Ura$^+$), but also sensitizes the strain to 5-fluoro-orotic acid (5-Foa) resulting in the second phenotype, Foa sensitivity (Foa$^S$). p53 cancer mutants that have lost function have the opposite phenotype of wild-type p53, Ura$^-$ Foa$^R$ (Brachmann et al., 1996). p53 proteins with partial loss of wild-type p53 function can be easily detected as well since they have the intermediate Ura$^+$Foa$^R$ phenotype. This reflects sufficient URA3 expression for survival on SC-Ura plates, but insufficient expression to be sensitive to 5-Foa.

Engineered p53 open reading frame. A new ORF for wild-type p53 with multiple silent restriction sites and optimized for codon usage in bacteria, yeast and mammalian cells (Wada, 199; Zhang, 1991) was designed with WebCutter 2.0 (http file type, www host server, firstmarket.com domain name, cutter/cut2.html directory) and constructed using the "KAPPA" method (Holowachuk, 1995). When compared with the natural p53 yeast expression plasmid pRB16, the engineered p53 ORF in the same yeast plasmid resulted in two-fold more p53 protein and identical yeast phenotypes (Brachmann, 1996; Brachmann, 1998; Vidal, 1996). Annealed oligonucleotides encoding for the most common p53 cancer mutations (see Table 2) were cloned into the engineered p53 ORF.

PCR- and oligonucleotide-mediated mutagenesis strategy to identify intragenic suppressor mutations for p53 cancer mutations. PCR-mediated mutagenesis was performed as previously described (Brachmann, 1998), except that engineered p53 ORFs for the p53 cancer mutants, mutagenic PCR conditions (Lin-Goerke, 1997; Svetlov, 1998) and Rby377, a diploid yeast strain with two copies of the p53-dependent URA3 reporter gene, were used. A library of annealed oligonucleotides that equally represented all possible amino acid changes in codons 239 and 240 and had approximately one in 100 additional nucleotides mutated were cloned into PflMI-NsiI gapped yeast expression plasmids for p53 cancer mutants, transformed into Rby377 and analyzed as described (Brachmann, 1998).

Yeast and mammalian assays for p53. Yeast assays for p53 and mammalian reporter gene assays were performed as described (Brachmann, 1996; Brachmann, 1998; Vidal, 1996).

REFERENCES

The disclosures of the following are expressly incorporated herein for all purposes.

Abarzua, P., LoSardo, J. E., Gubler, M. L., and Neri, A. (1995). Microinjection of monoclonal antibody PAb421 into human SW480 colorectal carcinoma cells restores the transcription activation function to mutant p53. Cancer Res 55, 3490–4.

Abarzua, P., LoSardo, J. E., Gubler, M. L., Spathis, R., Lu, Y. A., Felix, A., and Neri, A. (1996). Restoration of the transcription activation function to mutant p53 in human cancer cells. Oncogene 13, 2477–82.

Abraham, D. J., Wireko, F. C., Randad, R. S., Poyart, C., Kister, J., Bohn, B., Liard, J. F., and Kunert, M. P. (1992). Allosteric modifiers of hemoglobin: 2-[4-[[(3,5-disubstituted anilino)carbonyl]methyl]phenoxy]-2-methylpropionic acid derivatives that lower the oxygen affinity of hemoglobin in red cell suspensions, in whole blood, and in vivo in rats. Biochemistry 31, 9141–9.

Allred, D. C., Clark, G. M., Elledge, R., Fuqua, S. A., Brown, R. W., Chamness, G. C., Osborne, C. K., and McGuire, W. L. (1993). Association of p53 protein expression with tumor cell proliferation rate and clinical outcome in node-negative breast cancer. J Natl Cancer Inst 85, 200–6.

Baker, S. J., Markowitz, S., Fearon, E. R., Willson, J. K., and Vogelstein, B. (1990). Suppression of human colorectal carcinoma cell growth by wild-type p53. Science 249, 912–5.

Baldwin, E. T., Bhat, T. N., Liu, B., Pattabiraman, N., and Erickson, J. W. (1995). Structural basis of drug resistance for the V82A mutant of HIV-1 proteinase. Nat Struct Biol 2, 244–9.

Bardeesy, N., Beckwith, J. B., and Pelletier, J. (1995). Clonal expansion and attenuated apoptosis in Wilms' tumors are associated with p53 gene mutations. Cancer Res 55, 215–9.

Barinaga, M. (1997). From bench top to bedside. Science 278, 1036–9.

Bergh, J., Norberg, T., Sjogren, S., Lindgren, A., and Holmberg, L. (1995). Complete sequencing of the p53 gene provides prognostic information in breast cancer patients, particularly in relation to adjuvant systemic therapy and radiotherapy. Nat Med 1, 1029-34.

Berns, E. M., Klijn, J. G., van Putten, W. L., de Witte, H. H., Look, M. P., Meijer-van Gelder, M. E., Willman, K., Portengen, H., Benraad, T. J., and Foekens, J. A. (1998). p53 protein accumulation predicts poor response to tamoxifen therapy of patients with recurrent breast cancer. J Clin Oncol 16, 121–7.

Beroud, C., and Soussi, T. (1998). p53 gene mutation: software and database. Nucleic Acids Res 26, 200–4.

Bohacek, R. S., McMartin, C., and Guida, W. C. (1996). The art and practice of structure-based drug design: a molecular modeling perspective. Med Res Rev 16, 3–50.

Bracey, T. S., Miller, J. C., Preece, A., and Paraskeva, C. (1995). Gamma-radiation-induced apoptosis in human colorectal adenoma and carcinoma cell lines can occur in the absence of wild type p53. Oncogene 10, 2391–6.

Brachmann, R. K., and Boeke, J. D. (1997). Tag games in yeast: the two-hybrid system and beyond. Curr Opin Biotechnol 8, 561–8.

Brachmann, R. K., Vidal, M., and Boeke, J. D. (1996). Dominant-negative p53 mutations selected in yeast hit cancer hot spots. Proc Natl Acad Sci USA 93, 4091–5.

Brachmann, R. K., Yu, K., Eby, Y., Pavletich, N. P., and Boeke, J. D. (1998). Genetic selection of intragenic suppressor mutations that reverse the effect of common p53 cancer mutations. EMBO J. 17, 1847–59.

Brugarolas, J., Chandrasekaran, C., Gordon, J. I., Beach, D., Jacks, T., and Hannon, G. J. (1995). Radiation-induced cell cycle arrest compromised by p21 deficiency. Nature 377, 552–7.

Bullock, A. N., Henckel, J., and Fersht, A. R. (2000). Quantitative analysis of residual folding and DNA binding in mutant p53 core domain: definition of mutant states for rescue in cancer therapy. Oncogene. 19, 1245–56.

Cadwell, R. C., and Joyce, G. F. (1995). Mutagenic PCR. In PCR primer—a laboratory manual, C. W. Dieffenbach and G. S. Dveksler, eds., Cold Spring Harbor Laboratory Press, pp. 583–9.

Caelles, C., Helmberg, A., and Karin, M. (1994). p53-dependent apoptosis in the absence of transcriptional activation of p53-target genes. Nature 370, 220–3.

Cariello, N. F., Douglas, G. R., Gorelick, N. J., Hart, D. W., Wilson, J. D., and Soussi, T. (1998). Databases and software for the analysis of mutations in the human p53 gene, human hprt gene and both the lacI and lacZ gene in transgenic rodents. Nucleic Acids Res 26, 198–9.

Cho, Y., Gorina, S., Jeffrey, P. D., and Pavletich, N. P. (1994). Crystal structure of a p53 tumor suppressor-DNA complex: understanding tumorigenic mutations. Science 265, 346–55.

Clarke, A. R., Purdie, C. A., Harrison, D. J., Morris, R. G., Bird, C. C., Hooper, M. L., and Wyllie, A. H. (1993). Thymocyte apoptosis induced by p53-dependent and independent pathways. Nature 362, 849–52.

Clore, G. M., Omichinski, J. G., Sakaguchi, K., Zambrano, N., Sakamoto, H., Appella, E., and Gronenborn, A. M. (1994). High-resolution structure of the oligomerization domain of p53 by multidimensional NMR. Science 265, 386–91.

Cotton, F. A., Hazen, E. E., Jr., and Legg, M. J. (1979). Staphylococcal nuclease: proposed mechanism of action based on structure of enzyme-thymidine 3',5'-bisphosphate-calcium ion complex at 1.5-A resolution. Proc Natl Acad Sci USA 76, 2551–5.

Deng, C., Zhang, P., Harper, J. W., Elledge, S. J., and Leder, P. (1995). Mice lacking p21CIP1/WAF1 undergo normal development, but are defective in G1 checkpoint control. Cell 82, 675–84.

Donehower, L. A., and Bradley, A. (1993). The tumor suppressor p53. Biochim Biophys Acta 1155, 181–205.

el-Deiry, W. S., Tokino, T., Velculescu, V. E., Levy, D. B., Parsons, R., Trent, J. M., Lin, D., Mercer, W. E., Kinzler, K. W., and Vogelstein, B. (1993). WAF1, a potential mediator of p53 tumor suppression. Cell 75, 817–25.

Eliyahu, D., Goldfinger, N., Pinhasi-Kimhi, O., Shaulsky, G., Skumik, Y., Arai, N., Rotter, V., and Oren, M. (1988). Meth A fibrosarcoma cells express two transforming mutant p53 species. Oncogene 3, 313–21.

Elledge, R. M., Gray, R., Mansour, E., Yu, Y., Clark, G. M., Ravdin, P., Osborne, C. K., Gilchrist, K., Davidson, N. E., Robert, N., Tormey, D. C., and Allred, D. C. (1995). Accumulation of p53 protein as a possible predictor of response to adjuvant combination chemotherapy with cyclophosphamide, methotrexate, fluorouracil, and prednisone for breast cancer. J Natl Cancer Inst 87, 1254–6.

Erickson, J., Neidhart, D. J., VanDlie, J., Kempf, D. J., Wang, X. C., Norbeck, D. W., Plattner, J. J., Rittenhouse, J. W., Turon, M., Wideburg, N., Kohlbrenner, W. E., Simmer, R., Helfrich, R., Paul, D. A., and Knigge, M. (1990). Design, activity, and 2.8 A crystal structure of a C2 symmetric inhibitor complexed to HIV-1 protease. Science 249, 527–33.

Erickson, J. W., and Burt, S. K. (1996). Structural mechanisms of HIV drug resistance. Annu Rev Pharmacol Toxicol 36, 545–71.

Fisher, D. E. (1994). Apoptosis in cancer therapy: crossing the threshold. Cell 78, 539–42.

Foster, B. A., Coffey, H. A., Morin, M. J., Rastinejad, F. (1999). Pharmacological rescue of mutant p53 conformation and function. Science. 286, 2507–10.

Freeman, J., Schmidt, S., Scharer, E., and Iggo, R. (1994). Mutation of conserved domain II alters the sequence specificity of DNA binding by the p53 protein. EMBO J 13, 5393–400.

Friend, S. (1994). p53: a glimpse at the puppet behind the shadow play. Science 265, 334–5.

Fuchs, E. J., McKenna, K. A., and Bedi, A. (1997). p53-dependent DNA damage-induced apoptosis requires Fas/APO-1-independent activation of CPP32beta. Cancer Res 57, 2550–4.

Gibbs, J. B., and Oliff, A. (1994). Pharmaceutical research in molecular oncology. Cell 79, 193–8.

Gorina, S., and Pavletich, N. P. (1996). Structure of the p53 tumor suppressor bound to the ankyrin and SH3 domains of 53BP2. Science 274, 1001–5.

Gottlieb, T. M., and Oren, M. (1996). p53 in growth control and neoplasia. Biochim Biophys Acta 1287, 77–102.

Graeber, T. G., Osmanian, C., Jacks, T., Housman, D. E., Koch, C. J., Lowe, S. W., and Giaccia, A. J. (1996). Hypoxia-mediated selection of cells with diminished apoptotic potential in solid tumours. Nature 379, 88–91.

Greenblatt, M. S., Bennett, W. P., Hollstein, M., and Harris, C. C. (1994). Mutations in the p53 tumor suppressor gene: clues to cancer etiology and molecular pathogenesis. Cancer Res 54, 4855–78.

Haffner, R., and Oren, M. (1995). Biochemical properties and biological effects of p53. Curr Opin Genet Dev 5, 84–90.

Hainaut, P., Hernandez, T., Robinson, A., Rodriguez-Tome, P., Flores, T., Hollstein, M., Harris, C. C., and Montesano, R. (1998). IARC Database of p53 gene mutations in human tumors and cell lines: updated compilation, revised formats and new visualisation tools. Nucleic Acids Res 26, 205–13.

Hainaut, P, and Hollstein, M. (2000). p53 and human cancer: the first ten thousand mutations. Adv. Cancer Res. 77, 81–137.

Halazonetis, T. D., and Kandil, A. N. (1993). Conformational shifts propagate from the oligomerization domain of p53 to its tetrameric DNA binding domain and restore DNA binding to select p53 mutants. EMBO J 12, 5057–64.

Haldar, S., Negrini, M., Monne, M., Sabbioni, S., and Croce, C. M. (1994). Down-regulation of bcl-2 by p53 in breast cancer cells. Cancer Res 54, 2095–7.

Hann, B. C. L., D. P. (1995). The dominating effect of mutant p53. Nature Genetics 9, 221–222.

Hansen, R., and Oren, M. (1997). p53; from inductive signal to cellular effect. Curr Opin Genet Dev 7, 46–51.

Harris, C. C. (1996a). Structure and function of the p53 tumor suppressor gene: clues for rational cancer therapeutic strategies. Journal of the National Cancer Institute 88, 1442–1454.

Harris, C. C. (1996b). p53 tumor suppressor gene: from the basic research laboratory to the clinic—an abridged historical perspective. Carcinogenesis 17, 1187–98.

Harris, C. C., and Hollstein, M. (1993). Clinical implications of the p53 tumor-suppressor gene. N Engl J Med 329, 1318–27.

Harvey, M., Vogel, H., Morris, D., Bradley, A., Bernstein, A., and Donehower, L. A. (1995). A mutant p53 transgene accelerates tumour development in heterozygous but not nullizygous p53-deficient mice. Nat Genet 9, 305–11.

Haupt, Y., Maya, R., Kazaz, A., and Oren, M. (1997). Mdm2 promotes the rapid degradation of p53. Nature 387, 296–9.

Haupt, Y., Rowan, S., Shaulian, E., Vousden, K. H., and Oren, M. (1995). Induction of apoptosis in HeLa cells by trans-activation-deficient p53. Genes Dev 9, 2170–83.

Heimdal, K., Lothe, R. A., Lystad, S., Holm, R., Fossa, S. D., and Borresen, A. L. (1993). No germline TP53 mutations detected in familial and bilateral testicular cancer. Genes Chromosomes Cancer 6, 92–7.

Hermeking, H., Lengauer, C., Polyak, K., He, T.-C., Zhang, L., Thiagalingam, S., Kinzler, K. W., and Vogelstein, B. (1998). 14-3-3σ is a p53-regulated inhibitor of G2/M progression. Molecular Cell 1, 3–11.

Hernandez-Boussard, T., Rodriguez-Tome, P., Montesano, R., and Hainaut, P. (1999). IARC p53 mutation database: a relational database to compile and analyze p53 mutation in human tumors and cell lines. International Agency for Research on Cancer. Hum. Mutat. 14, 1–8.

Hinds, P., Finlay, C., and Levine, A. J. (1989). Mutation is required to activate the p53 gene for cooperation with the ras oncogene and transformation. J Virol 63, 739–46.

Hollstein, M., Sidransky, D., Vogelstein, B., and Harris, C. C. (1991). p53 mutations in human cancers. Science 253, 49–53.

Holowachuk, E. W., and Ruhoff, M. S. (1995). Efficient gene synthesis by Klenow assembly/extension-Pfu polymerase amplification (KAPPA) of overlapping oligonucleotides. PCR Methods Appl 4, 299–302.

Huang, C. L., Taki, T., Adachi, M., Konishi, T., Higashiyama, M., Kinoshita, M., Hadama, T., and Miyake, M. (1998). Mutations of p53 and K-ras genes as prognostic factors for non-small cell lung cancer. Int J Oncol 12, 553–63.

Hupp, T. R., Meek, D. W., Midgley, C. A., and Lane, D. P. (1993). Activation of the cryptic DNA binding function of mutant forms of p53. Nucleic Acids Res 21, 3167–74.

Hupp, T. R., Sparks, A., and Lane, D. P. (1995). Small peptides activate the latent sequence-specific DNA binding function of p53. Cell 83, 237–45.

Hupp, T. R., Lane, D. P., and Ball, K. L. (2000). Strategies for manipulating the p53 pathway in the treatment of human cancer. Biochem J. 352, 1–17.

Isola, J., Visakorpi, T., Holli, K., and Kallioniemi, O. P. (1992). Association of overexpression of tumor suppressor protein p53 with rapid cell proliferation and poor prognosis in node-negative breast cancer patients. J Natl Cancer Inst 84, 1109–14.

Jeffrey, P. D., Gorina, S., and Pavletich, N. P. (1995). Crystal structure of the tetramerization domain of the p53 tumor suppressor at 1.7 angstroms. Science 267, 1498–502.

Jost, C. A., Marin, M. C., and Kaelin, W. G., Jr. (1997). p73 is a human p53-related protein that can induce apoptosis. Nature 389, 191–4.

Kaghad, M., Bonnet, H., Yang, A., Creancier, L., Biscan, J. C., Valent, A., Minty, A., Chalon, P., Lelias, J. M., Dumont, X., Ferrara, P., McKeon, F., and Caput, D. (1997). Monoallelically expressed gene related to p53 at 1p36, a region frequently deleted in neuroblastoma and other human cancers. Cell 90, 809–19.

Kastan, M. B., Onyekwere, O., Sidransky, D., Vogelstein, B., and Craig, R. W. (1991). Participation of p53 protein in the cellular response to DNA damage. Cancer Res 51, 6304–11.

Kaufmann, S. H. (1989). Induction of endonucleolytic DNA cleavage in human acute myelogenous leukemia cells by etoposide, camptothecin, and other cytotoxic anticancer drugs: a cautionary note. Cancer Res 49, 5870–8.

Kinzler, K. W., and Vogelstein, B. (1994). Cancer therapy meets p53. N Engl J Med 331, 49–50.

Kirsch, D. G., Kastan, M. B. (1998). Tumor-suppressor p53: implications fo tumor development and prognosis. J. Clin. Oncol. 16, 3158–3168.

Knudson, C. M., Tung, K. S., Tourtellotte, W. G., Brown, G. A., and Korsmeyer, S. J. (1995). Bax-deficient mice with lymphoid hyperplasia and male germ cell death. Science 270, 96–9.

Ko, L. J., and Prives, C. (1996). p53: puzzle and paradigm. Genes Dev 10, 1054–72.

Kubbutat, M. H., Jones, S. N., and Vousden, K. H. (1997). Regulation of p53 stability by Mdm2. Nature 387, 299–303.

Kussie, P. H., Gorina, S., Marechal, V., Elenbaas, B., Moreau, J., Levine, A. J., and Pavletich, N. P. (1996). Structure of the MDM2 oncoprotein bound to the p53 tumor suppressor transactivation domain. Science 274, 948–53.

Lane, D. P., and Hall, P. A. (1997). MDM2—arbiter of p53's destruction. Trends Biochem Sci 22, 372–4.

Levine, A. J. (1997). p53, the cellular gatekeeper for growth and division. Cell 88, 323–31.

Lin-Goerke, J. L., Robbins, D. J., and Burczak, J. D. (1997). PCR-based random mutagenesis using manganese and reduced dNTP concentration. Biotechniques 23, 409–12.

Linke, S. P., Clarkin, K. C., Di Leonardo, A., Tsou, A., and Wahl, G. M. (1996). A reversible, p53-dependent G0/G1 cell cycle arrest induced by ribonucleotide depletion in the absence of detectable DNA damage. Genes Dev 10, 934–47.

Lowe, S. W. (1995). Cancer therapy and p53. Curr Opin Oncol 7, 547–53.

Lowe, S. W., Bodis, S., McClatchey, A., Remington, L., Ruley, H. E., Fisher, D. E., Housman, D. E., and Jacks, T. (1994). p53 status and the efficacy of cancer therapy in vivo. Science 266, 807–10.

Lowe, S. W., Schmitt, E. M., Smith, S. W., Osborne, B. A., and Jacks, T. (1993a). p53 is required for radiation-induced apoptosis in mouse thymocytes. Nature 362, 847–9.

Lowe, S. W., Ruley, H. E., Jacks, T., and Housman, D. E. (1993b). p53-dependent apoptosis modulates the cytotoxicity of anticancer agents. Cell 74, 957–67.

Malkin, D., Sexsmith, E., Yeger, H., Williams, B. R., and Coppes, M. J. (1994). Mutations of the p53 tumor suppressor gene occur infrequently in Wilms' tumor. Cancer Res 54, 2077–9.

Marcus, S., Polverino, A., Barr, M., and Wigler, M. (1994). Complexes between STE5 and components of the pheromone-responsive mitogen-activated protein kinase module. Proc Natl Acad Sci USA 91, 7762–6.

Marrone, T. J., Briggs, J. M., and McCammon, J. A. (1997). Structure-based drug design: computational advances. Annu Rev Pharmacol Toxicol 37, 71–90.

Michalovitz, D., Halevy, O., and Oren, M. (1991). p53 mutations: gains or losses? J Cell Biochem 45, 22–9.

Miller, M., Schneider, J., Sathyanarayana, B. K., Toth, M. V., Marshall, G. R., Clawson, L., Selk, L., Kent, S. B., and Wlodawer, A. (1989). Structure of complex of synthetic HIV-1 protease with a substrate-based inhibitor at 2.3 A resolution. Science 246, 1149–52.

Milner, J. (1995). DNA damage, p53 and anticancer therapies. Nature Medicine 1, 879–80.

Milner, J., and Medcalf, E. A. (1991). Cotranslation of activated mutant p53 with wild type drives the wild-type p53 protein into the mutant conformation. Cell 65, 765–74.

Miroy, G. J., Lai, Z., Lashuel, H. A., Peterson, S. A., Strang, C., and Kelly, J. W. (1996). Inhibiting transthyretin amyloid fibril formation via protein stabilization. Proc Natl Acad Sci USA 93, 15051–6.

Miura, M., Zhu, H., Rotello, R., Hartwieg, E. A., and Yuan, J. (1993). Induction of apoptosis in fibroblasts by IL-1 beta-converting enzyme, a mammalian homolog of the C. elegans cell death gene ced-3. Cell 75, 653–60.

Miyashita, T., Krajewski, S., Krajewska, M., Wang, H. G., Lin, H. K., Liebermann, D. A., Hoffman, B., and Reed, J. C. (1994). Tumor suppressor p53 is a regulator of bcl-2 and bax gene expression in vitro and in vivo. Oncogene 9, 1799–805.

Miyashita, T., and Reed, J. C. (1995). Tumor suppressor p53 is a direct transcriptional activator of the human bax gene. Cell 80, 293–9.

Muhlrad, D., Hunter, R., and Parker, R. (1992). A rapid method for localized mutagenesis of yeast genes. Yeast 8, 79–82.

Navia, M. A., Fitzgerald, P. M., McKeever, B. M., Leu, C. T., Heimbach, J. C., Herber, W. K., Sigal, I. S., Darke, P. L., and Springer, J. P. (1989). Three-dimensional structure of aspartyl protease from human immunodeficiency virus HIV-1. Nature 337, 615–20.

Nielsen, L. L., and Maneval, D. C. (1998). P53 tumor suppressor gene therapy for cancer. Cancer Gene Ther 5, 52–63.

Niewolik, D., Vojtesek, B., and Kovarik, J. (1995). p53 derived from human tumour cell lines and containing distinct point mutations can be activated to bind its consensus target sequence. Oncogene 10, 881–90.

Nikolova, P. V., Wong, K. B., DeDecker, B., Henckel, J., and Fersht, A. R. (2000). Mechanism of rescue of common p53 cancer mutation by second-site suppressor mutations. EMBO J. 19, 370–378.

O'Connor, P. M., Jackman, J., Bae, I., Myers, T. G., Fan, S., Mutoh, M., Scudiero, D. A., Monks, A., Sausville, E. A., Weinstein, J. N., Friend, S., Fornace, A. J., Jr., and Kohn, K. W. (1997). Characterization of the p53 tumor suppressor pathway in cell lines of the National Cancer Institute anticancer drug screen and correlations with the growth-inhibitory potency of 123 anticancer agents. Cancer Res 57, 4285–300.

Oren, M. (1997). Lonely no more: p53 finds its kin in a tumor suppressor haven. Cell 90, 829–32.

Owen-Schaub, L. B., Zhang, W., Cusack, J. C., Angelo, L. S., Santee, S. M., Fujiwara, T., Roth, J. A., Deisseroth, A. B., Zhang, W. W., Kruzel, E., and Radinsky, R. (1995). Wild-type human p53 and a temperature-sensitive mutant induce Fas/APO-1 expression. Mol Cell Biol 15, 3032–40.

Pavletich, N. P., Chambers, K. A., and Pabo, C. O. (1993). The DNA-binding domain of p53 contains the four conserved regions and the major mutation hot spots. Genes Dev 7, 2556–64.

Polyak, K., Xia, Y., Zweier, J. L., Kinzler, K. W., and Vogelstein, B. (1997). A model for p53-induced apoptosis. Nature 389, 300–5.

Prives, C. (1994). How loops, beta sheets, and alpha helices help us to understand p53. Cell 78, 543–6.

Prives, C. (1998). Signaling to p53: breaking the MDM2-p53 circuit. Cell. 95, 5–8.

Prives, C., and Hall, P. A. (1999). The p53 pathway. J. Pathol. 187, 112–26.

Righetti, S.C., Della Torre, G., Pilotti, S., Menard, S., Ottone, F., Colnaghi, M. I., Pierotti, M. A., Lavarino, C., Comarotti, M., Oriana, S., Bohm, S., Bresciani, G. L., Spatti, G., and Zunino, F. (1996). A comparative study of p53 gene mutations, protein accumulation, and response to cisplatin-based chemotherapy in advanced ovarian carcinoma. Cancer Res 56, 689–93.

Rose, R. B., Craik, C. S., and Stroud, R. M. (1998). Domain flexibility in retroviral proteases: structural implications for drug resistant mutations. Biochemistry 37, 2607–21.

Roth, J. A., Nguyen, D., Lawrence, D. D., Kemp, B. L., Carrasco, C. H., Ferson, D. Z., Hong, W. K., Komaki, R., Lee, J. J., Nesbitt, J. C., Pisters, K. M., Putnam, J. B., Schea, R., Shin, D. M., Walsh, G. L., Dolormente, M. M., Han, C. I., Martin, F. D., Yen, N., Xu, K., Stephens, L. C., McDonnell, T. J., Mukhopadhyay, T., and Cai, D. (1996). Retrovirus-mediated wild-type p53 gene transfer to tumors of patients with lung cancer. Nat Med 2, 985–91.

Rovinski, B., and Benchimol, S. (1988). Immortalization of rat embryo fibroblasts by the cellular p53 oncogene. Oncogene 2, 445–52.

Rusch, V., Klimstra, D., Venkatraman, E., Oliver, J., Martini, N., Gralla, R., Kris, M., and Dmitrovsky, E. (1995). Aberrant p53 expression predicts clinical resistance to cisplatin-based chemotherapy in locally advanced non-small cell lung cancer. Cancer Res 55, 5038–42.

Sauter, E. R., Ridge, J. A., Litwin, S., and Langer, C. J. (1995). Pretreatment p53 protein expression correlates with decreased survival in patients with end-stage head and neck cancer. Clinical Cancer Research 1, 1407–12.

Selivanova, G., Iotsova, V., Okan, I., Fritsche, M., Strom, M., Groner, B., Grafstrom, R. C., and Wiman, K. G. (1997). Restoration of the growth suppression function of mutant p53 by a synthetic peptide derived from the p53 C-terminal domain. Nat Med 3, 632–8.

Shortle, D., and Lin, B. (1985). Genetic analysis of staphylococcal nuclease: identification of three intragenic "global" suppressors of nuclease-minus mutations. Genetics 110, 539–55.

Stenger, J. E., Mayr, G. A., Mann, K., and Tegtmeyer, P. (1992). Formation of stable p53 homotetramers and multiples of tetramers. Mol Carcinog 5, 102–6.

Strasser, A., Harris, A. W., Jacks, T., and Cory, S. (1994). DNA damage can induce apoptosis in proliferating lymphoid cells via p53-independent mechanisms inhibitable by Bcl-2. Cell 79, 329–39.

Svetlov, V., and Cooper, T. G. (1998). Efficient PCR-based random mutagenesis of sub-genic (100 bp) DNA fragments. Yeast 14, 89–91.

Thiagalingam, S., Kinzler, K. W., and Vogelstein, B. (1995). PAK1, a gene that can regulate p53 activity in yeast. Proc Natl Acad Sci USA 92, 6062–6.

Thor, A. D., Moore, D. H., II, Edgerton, S. M., Kawasaki, E. S., Reihsaus, E., Lynch, H. T., Marcus, J. N., Schwartz, L., Chen, L. C., Mayall, B. H., and Smith, H. S. (1992). Accumulation of p53 tumor suppressor gene protein: an independent marker of prognosis in breast cancers. J Natl Cancer Inst 84, 845–55.

Vidal, M., Brachmann, R. K., Fattaey, A., Harlow, E., and Boeke, J. D. (1996). Reverse two-hybrid and one-hybrid systems to detect dissociation of protein-protein and DNA-protein interactions. Proc. Natl. Acad. Sci. USA 93, 10315–10320.

Vogelstein, B., and Kinzler, K. W. (1992). p53 function and dysfunction. Cell 70, 523–6.

Vogelstein, B., and Kinzler, K. W. (1994). Tumour-suppressor genes. X-rays strike p53 again. Nature 370, 174–5.

Vogelstein, B., Lane, D., and Levine, A. J. (2000). Surfing the p53 network. Nature 408, 307–10.

Wada, K., Wada, Y., Ishibashi, F., Gojobori, T., and Ikemura, T. (1992). Codon usage tabulated from the GenBank genetic sequence data. Nucleic Acids Res 20 Suppl, 2111–8.

Wada, M., Bartram, C. R., Nakamura, H., Hachiya, M., Chen, D. L., Borenstein, J., Miller, C. W., Ludwig, L., Hansen-Hagge, T. E., Ludwig, W. D., Reiter, A., Mizoguchi, H., and Koeffler, H. P. (1993). Analysis of p53 mutations in a large series of lymphoid hematologic malignancies of childhood. Blood 82, 3163–9.

Wagner, A. J., Kokontis, J. M., and Hay, N. (1994). Myc-mediated apoptosis requires wild-type p53 in a manner independent of cell cycle arrest and the ability of p53 to induce p21waf1/cip1. Genes Dev 8, 2817–30.

Waldman, T., Kinzler, K. W., and Vogelstein, B. (1995). p21 is necessary for the p53-mediated GI arrest in human cancer cells. Cancer Res 55, 5187–90.

Wallace-Brodeur, R. R., and Lowe, S. W. (1999). Clinical implications of p53 mutations. Cell Mol. Life Sci. 55, 64–75.

Wang, X. W., Vermeulen, W., Coursen, J. D., Gibson, M., Lupold, S. E., Forrester, K., Xu, G., Elmore, L., Yeh, H., Hoeijmakers, J. H., and Harris, C. C. (1996). The XPB and XPD DNA helicases are components of the p53-mediated apoptosis pathway. Genes Dev 10, 1219–32.

Watanabe, M., Fukutome, K., Shiraishi, T., Murata, M., Kawamura, J., Shimazaki, J., Kotake, T., and Yatani, R. (1997). Differences in the p53 gene mutational spectra of prostate cancers between Japan and Western countries. Carcinogenesis 18, 1355–8.

Weinstein, J. N., Myers, T. G., O'Connor, P. M., Friend, S. H., Formace, A. J., Jr., Kohn, K. W., Fojo, T., Bates, S. E., Rubinstein, L. V., Anderson, N. L., Buolamwini, J. K., van Osdol, W. W., Monks, A. P., Scudiero, D. A., Sausville, E. A., Zaharevitz, D. W., Bunow, B., Viswanadhan, V. N., Johnson, G. S., Wittes, R. E., and Paull, K. D. (1997). An information-intensive approach to the molecular pharmacology of cancer. Science 275, 343–9.

White, E. (1996). Life, death, and the pursuit of apoptosis. Genes Dev 10, 1–15.

Wieczorek, A. M., Waterman, J. L., Waterman, M. J., and Halazonetis, T. D. (1996). Structure-based rescue of common tumor-derived p53 mutants. Nat Med 2, 1143–6.

Wlodawer, A., Miller, M., Jaskolski, M., Sathyanarayana, B. K., Baldwin, E., Weber, I. T., Selk, L. M., Clawson, L., Schneider, J., and Kent, S. B. (1989). Conserved folding in retroviral proteases: crystal structure of a synthetic HIV-1 protease. Science 245, 616–21.

Wu, G. S., Burns, T. F., McDonald III, E. R., Jiang, W., Meng, R., Krantz, I. D., Kao, G., Gan, D.-D., Zhou, J. Y., Muschel, R., Hamilton, S. R., Spinner, N. B., Markowitz, S., Wu, G., and El-Deiry, W. S. (1997). KILLER/DR5 is a DNA damage-inducible p53-regulated death receptor gene. Nature Genetics 17, 141–3.

Yin, C., Knudson, C. M., Korsmeyer, S. J., and Van Dyke, T. (1997). Bax suppresses tumorigenesis and stimulates apoptosis in vivo. Nature 385, 637–40.

Yin, Y., Terauchi, Y., Solomon, G. G., Aizawa, S., Rangarajan, P. N., Yazaki, Y., Kadowaki, T., and Barrett, J. C. (1998). Involvement of p85 in p53-dependent apoptotic response to oxidative stress. Nature 391, 707–10.

Zhang, S. P., Zubay, G., and Goldman, E. (1991). Low-usage codons in Escherichia coli, yeast, fruit fly and primates. Gene 105, 61–72.

Zhu, L., van den Heuvel, S., Helin, K., Fattaey, A., Ewen, M., Livingston, D., Dyson, N., and Harlow, E. (1993). Inhibition of cell proliferation by p107, a relative of the retinoblastoma protein. Genes Dev 7, 1111–25.

What is claimed is:

1. An isolated nucleic acid molecule comprising a nucleotide sequence as shown in SEQ ID NO: 1.

2. A cell comprising the nucleic acid molecule of claim 1, wherein said cell is in in vitro culture.

* * * * *

SEQUENCE LISTING

<160> NUMBER OF SEQ ID NOS: 71

<210> SEQ ID NO 1
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 1

```
atggaagaac cacagtcaga tcctagcgtc gaaccacctc tgagtcagga aacctttca      60 gacctgtgga aattgcttcc tgaaaacaac gttctgtccc cattgcctag tcaagcaatg     120
gatgatttga tgctgtcccc agacgatatt gaacaatggt tcactgaaga tccaggccca     180
gatgaagctc cacgaatgcc agaggccgct ccaccggttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagccctt aacaagatgt tttgccaact cgcgaagacc     420
tgcccagtcc aactgtgggt cgactccacc cctccacctg gtacacgtgt ccgcgcaatg     480
gccatctaca agcagagcca gcacatgacg gaggtcgtac gacgctgtcc acaccatgag     540
cgctgctcag attctgatgg tctggcgcca ccacagcatc ttatccgagt ggaaggtaac     600
ctacgcgtgg agtatctaga tgaccgcaac acttttcgac acagtgtggt ggtgccatat     660
gagccaccag aagttggctc tgactgcacc accatccact acaactatat gtgtaacagt     720
tcatgcatgg gcggcatgaa ccgcggccg atcctgacca tcatcactct cgaggattcc     780
tcaggtaatc tcctaggacg gaattccttt gaggtgcgtg tttgtgcatg cccgggccgc     840
gatcgccgga ccgaagagga gaatctccgg aagaaaggtg agcctcacca cgagctgcca     900
ccaggaagca ctaagcgagc actgccaaac aacaccagca gttctccaca gccaaagaag     960
aaacctttgg acggagaata tttcacccttt cagatccgtg gccgtgagcg gttcgagatg    1020
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                      1182
```

<210> SEQ ID NO 2
<211> LENGTH: 1182
<212> TYPE: DNA
<213> ORGANISM: Artificial Sequence
<220> FEATURE:

<223> OTHER INFORMATION: Produced by genetic engineering

<400> SEQUENCE: 2

```
atggaagaac cacagtcaga tcctagcgtc gaaccacccc tgagtcagga aaccttttca      60
gatctgtgga agcttcttcc tgaaaacaac gttctgtccc cattgcctag tcaagcaatg     120
gatgatttga tgctgagccc agacgatatt gaacaatggt tcactgagga tccaggccca     180
gatgaagctc cacgaatgcc agaggccgct ccaccggttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagcccct aacaagatgt tttgccaact cgcgaagacc     420
tgcccagtcc aactgtgggt cgactccacc cctccacctg gtacacgtgt ccgcgcaatg     480
gccatctaca agcagagcca gcacatgacg gaggtcgtac gacgctgtcc acaccatgag     540
cgctgctcag attctgatgg tctggcgcca ccacagcatc ttatccgagt ggaaggtaac     600
ctacgcgtgg agtatctaga tgaccgcaac acttttcgac acagtgtggt ggtgccatat     660
gagccaccag aagttggctc tgactgcacc accatccact acaactatat gtgtaacagt     720
tcatgcatgg gcggcatgaa ccggcggccg atcctgacca tcatcactct cgaggattcc     780
tcaggtaatc tcctaggacg gaattccttt gaggtgcgtg tttgtgcatg cccgggccgc     840
gatcgccgga ccgaagagga gaatctccgg aagaaggtg agcctcacca cgagctgcca     900
ccaggaagca ctaagcgagc actgccaaac acaccagca gttctccaca gccaaagaag     960
aaacctttgg acggagaata tttcacccct cagatccgtg gccgtgagcg gttcgagatg    1020
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                       1182
```

<210> SEQ ID NO 3
<211> LENGTH: 1181
<212> TYPE: DNA
<213> ORGANISM: Artificial Sequence
<220> FEATURE:
<223> OTHER INFORMATION: Produced by genetic engineering

<400> SEQUENCE: 3

```
atggaagaac cacagtcaga tcctagcgtc gaaccacccc tgagtcagga aaccttttca      60
gatctgtgga agcttcttcc tgaaaacaac gttctgtccc cattgcctag tcaagcaatg     120
gatgatttga tgctgagccc agacgatatt gaacaatggt tcactgagga tccaggccca     180
gatgaagctc cacgaatgcc agaggccgct ccaccggttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagcccct aacaagatgt tttgccaact cgcgaagacc     420
tgcccagtcc aactgtgggt cgactccacc cctccacctg gtacacgtgt ccgcgcaatg     480
gccatctaca agcagagcca gcacatgacg gaggtcgtac gacgctgtcc acaccatgag     540
cgctgctcag attctgatgg tctggcgcca ccacagcatc ttatccgagt ggaaggtaac     600
ctacgcgtgg agtatctaga tgaccgcaac acttttcgac acagtgtggt ggtgccatat     660
gagccaccag aagttggctc tgactgcacc accatccact acaactatat gtgtaacagt     720
tcatgcatgg gcggcatgaa ccggcggccg atcctgacca tcatcactct cgaggattcc     780
```

```
tcaggtaatc tcctaggacg gaattccttt gaggtgcgtg tttgtgcatg cccgggccgc      840
gatcgccgga ccgaagagga gaatctccgg aagaaggtg agcctcacca cgagctgcca      900
ccaggaagca ctaagcgagc actgccaaac aacacgagct cttctccaca gccaaagaag     960
aaacctttgg acggagaata tttcaccctg cagatccgtg gccgtgagcg gttcgagatg    1020
ttccgagagc tgaatgaggc cttagaactt aaggatgccc aggctggtaa ggagccagga    1080
ggcagccggg cccattcgtc tcacctgaag tccaaaaagg gtcagtctac tagtcgccat    1140
aaaaaactga gttcaagacc gaaggtcctg actcagactg a                        1181

<210> SEQ ID NO 4
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 4
atggaagaac acagtcaga tcctagcgtc gaaccacctc tgagtcagga aaccttttca      60
gacctgtgga aattgcttcc tgaaaacaac gttctgtccc cattgcctag tcaagcaatg    120
gatgatttga tgctgtcccc agacgatatt gaacaatggt tcactgaaga tccaggccca    180
gatgaagctc cacgaatgcc agaggccgct ccaccggttg ccccagcacc agcagctcct    240
acaccggcgg ccccagctcc ggccccatcc tggcctctgt catcttctgt cccttcccag    300
aaaacctacc agggcagcta cggtttccgt ctgggcttct tgcattctgg aactgccaag    360
tctgttactt gtacgtactc tccagcccct aacaagatgt tttgccaact cgcgaagacc    420
tgcccagtcc aactgtgggt cgactccacc cctccacctg gtacacgtgt ccgcgcaatg    480
gccatctaca gcagagcca gcacatgacg gaggtcgtac gtcactgtcc acaccatgag     540
cgctgctcag attctgatgg tctggcgcca ccacagcatc ttatccgagt ggaaggtaac    600
ctacgcgtgg agtatctaga tgaccgcaac acttttcgac acagtgtggt ggtgccatat    660
gagccaccag aagttggctc tgactgcacc accatccact acaactatat gtgtaacagt    720
tcatgcatgg gcggcatgaa ccggcggccg atcctgacca tcatcactct cgaggattcc    780
tcaggtaatc tcctaggacg gaattccttt gaggtgcgtg tttgtgcatg cccgggccgc    840
gatcgccgga ccgaagagga gaatctccgg aagaaggtg agcctcacca cgagctgcca     900
ccaggaagca ctaagcgagc actgccaaac aacaccagca gttctccaca gccaaagaag    960
aaacctttgg acggagaata tttcaccctt cagatccgtg gccgtgagcg gttcgagatg   1020
ttccgagagc tgaatgaggc cttagaactt aaggatgccc aggctggtaa ggagccagga   1080
ggcagccgtg ctcatagcag ccacctgaag tccaaaaagg gtcagtctac ctcccgccat   1140
aaaaaactga tgttcaagac cgaaggtcct gactcagact ga                      1182

<210> SEQ ID NO 5
<211> LENGTH: 1181
<212> TYPE: DNA
<213> ORGANISM: Artificial Sequence
<220> FEATURE:
<223> OTHER INFORMATION: Produced by genetic engineering

<400> SEQUENCE: 5
tggaagaacc acagtcagat cctagcgtcg aaccacctct gagtcaggaa accttttcag     60
acctgtggaa attgcttcct gaaaacaacg ttctgtcccc attgcctagt caagcaatgg    120
```

-continued

```
atgatttgat gctgtcccca gacgatattg aacaatggtt cactgaagat ccaggcccag    180
atgaagctcc acgaatgcca gaggccgctc caccggttgc cccagcacca gcagctccta    240
caccggcggc cccagctccg gccccatcct ggcctctgtc atcttctgtc ccttcccaga    300
aaacctacca gggcagctac ggtttccgtc tgggcttctt gcattctgga actgccaagt    360
ctgttacttg tacgtactct ccagccctta acaagatgtt ttgccaactc gcgaagacct    420
gcccagtcca actgtgggtc gactccaccc ctccacctgg tacacgtgtc cgcgcaatgg    480
ccatctacaa gcagagccag cacatgacgg aggtcgtacg acgctgtcca caccatgagc    540
gctgctcaga ttctgatggt ctggcgccac cacagcatct tatccgagtg gaaggtaacc    600
tacgcgtgga gtatctagat daccgcaaca cttttcgaca cagtgtggtg gtgccatatg    660
agccaccaga agttggctct gactgcacca ccatccacta caactatatg tgtaacagtt    720
catgcatggg cggcatgaac cagcggccga tcctgaccat catcactctc gaggattcct    780
caggtaatct cctaggacgg aattcctttg aggtgcgtgt ttgtgcatgc ccgggccgcg    840
atcgccggac cgaagaggag aatctccgga agaaggtga gcctcaccac gagctgccac    900
caggaagcac taagcgagca ctgccaaaca acaccagcag ttctccacag ccaaagaaga    960
aacctttgga cggagaatat ttcacccttc agatccgtgg ccgtgagcgg ttcgagatgt   1020
tccgagagct gaatgaggcc ttagaactta aggatgccca ggctggtaag gagccaggag   1080
gcagccgtgc tcatagcagc cacctgaagt ccaaaaaggg tcagtctacc tcccgccata   1140
aaaaactgat gttcaagacc gaaggtcctg actcagactg a                      1181
```

<210> SEQ ID NO 6
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 6

```
atggaagaac cacagtcaga tcctagcgtc gaaccacctc tgagtcagga aaccttttca     60
gacctgtgga aattgcttcc tgaaaacaac gttctgtccc cattgcctag tcaagcaatg    120
gatgatttga tgctgtcccc agacgatatt gaacaatggt tcactgaaga tccaggccca    180
gatgaagctc cacgaatgcc agaggccgct ccaccggttg ccccagcacc agcagctcct    240
acaccggcgg ccccagctcc ggccccatcc tggcctctgt catcttctgt cccttcccag    300
aaaacctacc agggcagcta cggtttccgt ctgggcttct tgcattctgg aactgccaag    360
tctgttactt gtacgtactc tccagcccct taacaagatgt tttgccaact cgcgaagacc    420
tgcccagtcc aactgtgggt cgactccacc cctccacctg gtacacgtgt ccgcgcaatg    480
gccatctaca agcagagcca gcacatgacg gaggtcgtac gacgctgtcc acaccatgag    540
cgctgctcag attctgatgg tctggcgcca ccacagcatc ttatccgagt ggaaggtaac    600
ctacgcgtgg agtatctaga tgaccgcaac acttttcgac acagtgtggt ggtgccatat    660
gagccaccag aagttggctc tgactgcacc accatccact acaactatat gtgtaacagt    720
tcatgcatgg gcggcatgaa ccggcggccg atcctgacca tcatcactct cgaggattcc    780
tcaggtaatc tcctaggacg gaattccttt gaggtgcacg tttgtgcatg cccgggccgc    840
gatcgccgga ccgaagagga gaatctccgg aagaaggtga gcctcacca cgagctgcca    900 ccaggaagca ctaagcgagc actgccaaac aacaccagca gttctccaca gccaaagaag    960
aaacctttgg acggagaata tttcacccctt cagatccgtg gccgtgagcg gttcgagatg   1020
```

```
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                       1182

<210> SEQ ID NO 7
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 7
atggaagaac cacagtcaga tcctagcgtc gaaccacctc tgagtcagga aaccttttca     60
gacctgtgga aattgcttcc tgaaaacaac gttctgtccc cattgcctag tcaagcaatg    120
gatgatttga tgctgtcccc agacgatatt gaacaatggt tcactgaaga tccaggccca    180
gatgaagctc cacgaatgcc agaggccgct ccaccggttg ccccagcacc agcagctcct    240
acaccggcgg ccccagctcc ggccccatcc tggcctctgt catcttctgt cccttcccag    300
aaaacctacc agggcagcta cggtttccgt ctgggcttct tgcattctgg aactgccaag    360
tctgttactt gtacgtactc tccagcccct aacaagatgt tttgccaact cgcgaagacc    420
tgcccagtcc aactgtgggt cgactccacc cctccacctg gtacacgtgt ccgcgcaatg    480
gccatctaca gcagagcca gcacatgacg gaggtcgtac gacgctgtcc acaccatgag    540
cgctgctcag attctgatgg tctggcgcca ccacagcatc ttatccgagt ggaaggtaac    600
ctacgcgtgg agtatctaga tgaccgcaac acttttcgac acagtgtggt ggtgccatat    660
gagccaccag aagttggctc tgactgcacc accatccact acaactatat gtgtaacagt    720
tcatgcatgg gcggcatgaa ctggcggccg atcctgacca tcatcactct cgaggattcc    780
tcaggtaatc tcctaggacg gaattccttt gaggtgcgtg tttgtgcatg cccgggccgc    840
gatcgccgga ccgaagagga gaatctccgg aagaaggtg agcctcacca cgagctgcca    900
ccaggaagca ctaagcgagc actgccaaac aacaccagca gttctccaca gccaaagaag    960
aaacctttgg acggagaata tttcaccctt cagatccgtg gccgtgagcg gttcgagatg   1020
ttccgagagc tgaatgaggc cttagaactt aaggatgccc aggctggtaa ggagccagga   1080
ggcagccgtg ctcatagcag ccacctgaag tccaaaaagg gtcagtctac ctcccgccat   1140
aaaaaactga tgttcaagac cgaaggtcct gactcagact ga                      1182

<210> SEQ ID NO 8
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 8
atggaagaac cacagtcaga tcctagcgtc gaaccacctc tgagtcagga aaccttttca     60
gacctgtgga aattgcttcc tgaaaacaac gttctgtccc cattgcctag tcaagcaatg    120
gatgatttga tgctgtcccc agacgatatt gaacaatggt tcactgaaga tccaggccca    180
gatgaagctc cacgaatgcc agaggccgct ccaccggttg ccccagcacc agcagctcct    240
acaccggcgg ccccagctcc ggccccatcc tggcctctgt catcttctgt cccttcccag    300
aaaacctacc agggcagcta cggtttccgt ctgggcttct tgcattctgg aactgccaag    360
```

| | |
|---|---:|
| tctgttactt gtacgtactc tccagcccit aacaagatgt tttgccaact cgcgaagacc | 420 |
| tgcccagtcc aactgtgggt cgactccacc cctccacctg gtacacgtgt ccgcgcaatg | 480 |
| gccatctaca agcagagcca gcacatgacg gaggtcgtac gacgctgtcc acaccatgag | 540 |
| cgctgctcag attctgatgg tctggcgcca ccacagcatc ttatccgagt ggaaggtaac | 600 |
| ctacgcgtgg agtatctaga tgaccgcaac acttttcgac acagtgtggt ggtgccatat | 660 |
| gagccaccag aagttggctc tgactgcacc accatccact acaactatat gtgtaacagt | 720 |
| tcatgcatgg gcggcatgaa ccggcggccg atcctgacca tcatcactct cgaggattcc | 780 |
| tcaggtaatc tcctaggacg gaattccttt gaggtgtgcg tttgtgcatg cccgggccgc | 840 |
| gatcgccgga ccgaagagga gaatctccgg aagaaggtg agcctcacca cgagctgcca | 900 |
| ccaggaagca ctaagcgagc actgccaaac aacaccagca gttctccaca gccaaagaag | 960 |
| aaacctttgg acggagaata tttcacccit cagatccgtg gccgtgagcg gttcgagatg | 1020 |
| ttccgagagc tgaatgaggc cttagaactt aaggatgccc aggctggtaa ggagccagga | 1080 |
| ggcagccgtg ctcatagcag ccacctgaag tccaaaaagg gtcagtctac ctcccgccat | 1140 |
| aaaaaactga tgttcaagac cgaaggtcct gactcagact ga | 1182 |

<210> SEQ ID NO 9
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 9

| | |
|---|---:|
| atggaagaac cacagtcaga tcctagcgtc gaaccacctc tgagtcagga aaccttttca | 60 |
| gacctgtgga aattgcttcc tgaaaacaac gttctgtccc cattgcctag tcaagcaatg | 120 |
| gatgatttga tgctgtcccc agacgatatt gaacaatggt tcactgaaga tccaggccca | 180 |
| gatgaagctc cacgaatgcc agaggccgct ccaccggttg ccccagcacc agcagctcct | 240 |
| acaccggcgg ccccagctcc ggccccatcc tggcctctgt catcttctgt cccttcccag | 300 |
| aaaacctacc agggcagcta cggtttccgt ctgggcttct tgcattctgg aactgccaag | 360 |
| tctgttactt gtacgtactc tccagcccit aacaagatgt tttgccaact cgcgaagacc | 420 |
| tgcccagtcc aactgtgggt cgactccacc cctccacctg gtacacgtgt ccgcgcaatg | 480 |
| gccatctaca agcagagcca gcacatgacg gaggtcgtac gacgctgtcc acaccatgag | 540 |
| cgctgctcag attctgatgg tctggcgcca ccacagcatc ttatccgagt ggaaggtaac | 600 |
| ctacgcgtgg agtatctaga tgaccgcaac acttttcgac acagtgtggt ggtgccatat | 660 |
| gagccaccag aagttggctc tgactgcacc accatccact acaactatat gtgtaacagt | 720 |
| tcatgcatgg gcggcatgaa ccggcggccg atcctgacca tcatcactct cgaggattcc | 780 |
| tcaggtaatc tcctaggacg gaattccttt gaggtgtgcg tttgtgcatg cccgggccgc | 840 |
| gactggcgga ccgaagagga gaatctccgg aagaaggtg agcctcacca cgagctgcca | 900 |
| ccaggaagca ctaagcgagc actgccaaac aacaccagca gttctccaca gccaaagaag | 960 |
| aaacctttgg acggagaata tttcacccit cagatccgtg gccgtgagcg gttcgagatg | 1020 |
| ttccgagagc tgaatgaggc cttagaactt aaggatgccc aggctggtaa ggagccagga | 1080 |
| ggcagccgtg ctcatagcag ccacctgaag tccaaaaagg gtcagtctac ctcccgccat | 1140 |
| aaaaaactga tgttcaagac cgaaggtcct gactcagact ga | 1182 |

-continued

```
<210> SEQ ID NO 10
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 10
atggaagaac cacagtcaga tcctagcgtc gaaccacctc tgagtcagga aaccttttca      60
gacctgtgga aattgcttcc tgaaaacaac gttctgtccc cattgcctag tcaagcaatg     120
gatgatttga tgctgtcccc agacgatatt gaacaatggt tcactgaaga tccaggccca     180
gatgaagctc cacgaatgcc agaggccgct ccaccggttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagcccct aacaagatgt tttgccaact cgcgaagacc     420
tgcccagtcc aactgtgggt cgactccacc cctccacctg gtacacgtgt ccgcgcaatg     480
gccatctaca gcagagcca gcacatgacg gaggtcgtac gacgctgtcc acaccatgag     540
cgctgctcag attctgatgg tctggcgcca ccacagcatc ttatccgagt ggaaggtaac     600
ctacgcgtgg agtatctaga tgaccgcaac acttttcgac acagtgtggt ggtgccatat     660
gagccaccag aagttggctc tgactgcacc accatccact acaactatat gtgtaacagt     720
tcatgcatgg gcggcatgaa ccggtctccg atcctgacca tcatcactct cgaggattcc     780
tcaggtaatc tcctaggacg gaattccttt gaggtgcgtg tttgtgcatg cccgggccgc     840
gatcgccgga ccgaagagga gaatctccgg aagaaggtg agcctcacca cgagctgcca     900
ccaggaagca ctaagcgagc actgccaaac acaccagca gttctccaca gccaaagaag     960
aaacctttgg acggagaata tttcaccctt cagatccgtg gccgtgagcg gttcgagatg     1020
ttccgagagc tgaatgaggc cttagaactt aaggatgccc aggctggtaa ggagccagga     1080
ggcagccgtg ctcatagcag ccacctgaag tccaaaaagg gtcagtctac ctcccgccat     1140
aaaaaactga tgttcaagac cgaaggtcct gactcagact ga                       1182

<210> SEQ ID NO 11
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 11
atggaagaac cacagtcaga tcctagcgtc gaaccacctc tgagtcagga aaccttttca      60
gacctgtgga aattgcttcc tgaaaacaac gttctgtccc cattgcctag tcaagcaatg     120
gatgatttga tgctgtcccc agacgatatt gaacaatggt tcactgaaga tccaggccca     180
gatgaagctc cacgaatgcc agaggccgct ccaccggttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagcccct aacaagatgt tttgccaact cgcgaagacc     420
tgcccagtcc aactgtgggt cgactccacc cctccacctg gtacacgtgt ccgcgcaatg     480
gccatctaca gcagagcca gcacatgacg gaggtcgtac gacgctgtcc acaccatgag     540
cgctgctcag attctgatgg tctggcgcca ccacagcatc ttatccgagt ggaaggtaac     600
```

```
ctacgcgtgg agtatctaga tgaccgcaac acttttcgac acagtgtggt ggtgccatat      660
gagccaccag aagttggctc tgactgcacc accatccact acaactatat gtgtaacagt      720
tcatgcatgg gctctatgaa ccggcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaggtg agcctcacca cgagctgcca       900
ccaggaagca ctaagcgagc actgccaaac aacaccagca gttctccaca gccaaagaag      960
aaacctttgg acggagaata tttcacccctt cagatccgtg gccgtgagcg gttcgagatg    1020
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                       1182

<210> SEQ ID NO 12
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 12
atggaagaac cacagtcaga tcctagcgtc gaaccacctc tgagtcagga aaccttttca       60
gacctgtgga aattgcttcc tgaaaacaac gttctgtccc cattgcctag tcaagcaatg      120
gatgatttga tgctgtcccc agacgatatt gaacaatggt tcactgaaga tccaggccca      180
gatgaagctc cacgaatgcc agaggccgct ccaccggttg ccccagcacc agcagctcct      240
acaccggcgg ccccagctcc ggccccatcc tggcctctgt catcttctgt cccttcccag      300
aaaacctacc agggcagcta cggtttccgt ctgggcttct tgcattctgg aactgccaag      360
tctgttactt gtacgtactc tccagcccctt aacaagatgt tttgccaact cgcgaagacc      420
tgcccagtcc aactgtgggt cgactccacc cctccacctg gtacacgtgt ccgcgcaatg      480
gccatctaca gcagagcca gcacatgacg gaggtcgtac gacgctgtcc acaccatgag      540
cgctgctcag attctgatgg tctggcgcca ccacagcatc ttatccgagt ggaaggtaac      600
ctacgcgtgg agtatctaga tgaccgcaac acttttcgac acagtgtggt ggtgccatgc      660
gagccaccag aagttggctc tgactgcacc accatccact acaactatat gtgtaacagt      720
tcatgcatgg gcggcatgaa ccggcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaggtg agcctcacca cgagctgcca       900
ccaggaagca ctaagcgagc actgccaaac aacaccagca gttctccaca gccaaagaag      960
aaacctttgg acggagaata tttcacccctt cagatccgtg gccgtgagcg gttcgagatg    1020
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                       1182

<210> SEQ ID NO 13
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 13
```

-continued

```
atggaagaac cacagtcaga tcctagcgtc gaaccacctc tgagtcagga aaccttttca      60
gacctgtgga aattgcttcc tgaaaacaac gttctgtccc cattgcctag tcaagcaatg     120
gatgatttga tgctgtcccc agacgatatt gaacaatggt tcactgaaga tccaggccca     180
gatgaagctc cacgaatgcc agaggccgct ccaccggttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagccctt aacaagatgt tttgccaact cgcgaagacc     420
tgcccagtcc aactgtgggt cgactccacc cctccacctg gtacacgtgt ccgcgcaatg     480
gccatctaca gcagagcca gcacatgacg gaggtcgtac gacgcttccc acaccatgag     540
cgctgctcag attctgatgg tctggcgcca ccacagcatc ttatccgagt ggaaggtaac     600
ctacgcgtgg agtatctaga tgaccgcaac acttttcgac acagtgtggt ggtgccatat     660
gagccaccag aagttggctc tgactgcacc accatccact acaactatat gtgtaacagt     720
tcatgcatgg gcggcatgaa ccggcggccg atcctgacca tcatcactct cgaggattcc     780
tcaggtaatc tcctaggacg gaattccttt gaggtgcgtg tttgtgcatg cccgggccgc     840
gatcgccgga ccgaagagga gaatctccgg aagaaggtg agcctcacca cgagctgcca     900
ccaggaagca ctaagcgagc actgccaaac aacaccagca gttctccaca gccaaagaag     960
aaacctttgg acgagaata tttcacccctt cagatccgtg ccgtgagcg gttcgagatg    1020 ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                       1182
```

<210> SEQ ID NO 14
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 14

```
atggaagaac cacagtcaga tcctagcgtc gaaccacctc tgagtcagga aaccttttca      60
gacctgtgga aattgcttcc tgaaaacaac gttctgtccc cattgcctag tcaagcaatg     120
gatgatttga tgctgtcccc agacgatatt gaacaatggt tcactgaaga tccaggccca     180
gatgaagctc cacgaatgcc agaggccgct ccaccggttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagccctt aacaagatgt tttgccaact cgcgaagacc     420
tgcccagtcc aactgtgggt cgactccacc cctccacctg gtacacggtt ccgcgcaatg     480
gccatctaca gcagagcca gcacatgacg gaggtcgtac gacgctgtcc acaccatgag     540
cgctgctcag attctgatgg tctggcgcca ccacagcatc ttatccgagt ggaaggtaac     600
ctacgcgtgg agtatctaga tgaccgcaac acttttcgac acagtgtggt ggtgccatat     660
gagccaccag aagttggctc tgactgcacc accatccact acaactatat gtgtaacagt     720
tcatgcatgg gcggcatgaa ccggcggccg atcctgacca tcatcactct cgaggattcc     780
tcaggtaatc tcctaggacg gaattccttt gaggtgcgtg tttgtgcatg cccgggccgc     840
```

```
gatcgccgga ccgaagagga gaatctccgg aagaaaggtg agcctcacca cgagctgcca      900
ccaggaagca ctaagcgagc actgccaaac aacaccagca gttctccaca gccaaagaag      960
aaacctttgg acggagaata tttcacccct tcagatccgtg gccgtgagcg gttcgagatg    1020
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                        1182
```

<210> SEQ ID NO 15
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 15

```
atggaagaac cacagtcaga tcctagcgtc gaaccacctc tgagtcagga aaccttttca       60
gacctgtgga aattgcttcc tgaaaacaac gttctgtccc cattgcctag tcaagcaatg      120
gatgatttga tgctgtcccc agacgatatt gaacaatggt tcactgaaga tccaggccca      180
gatgaagctc cacgaatgcc agaggccgct ccaccggttg ccccagcacc agcagctcct      240
acaccggcgg ccccagctcc ggccccatcc tggcctctgt catcttctgt cccttcccag      300 aaacctacc agggcagcta cggtttccgt ctgggcttct tgcattctgg aactgccaag      360
tctgttactt gtacgtactc tccagccctt aacaagatgt tttgccaact cgcgaagacc      420
tgcccagtcc aactgtgggt cgactccacc cctccacctg gtacacgtgt ccgcgcaatg      480
gccatctaca gcagagcca gcacatgacg gaggtcgtac gacgctgtcc acaccatgag      540
cgctgctcag attctgatgg tctggcgcca ccacagcatc ttatccgagt ggaaggtaac      600
ctacgcgtgg agtatctaga tgaccgcaac acttttcgac acagtgtggt ggtgccatat      660
gagccaccag aagttggctc tgactgcacc accatccact acaactacat atgtaacagt      720
tcatgcatgg gcggcatgaa ccggcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaaggtg agcctcacca cgagctgcca      900
ccaggaagca ctaagcgagc actgccaaac aacaccagca gttctccaca gccaaagaag      960
aaacctttgg acggagaata tttcacccct tcagatccgtg gccgtgagcg gttcgagatg   1020
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat   1140
aaaaaactga tgttcaagac cgaaggtcct gactcagact ga                       1182
```

<210> SEQ ID NO 16
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 16

```
atggaagaac cacagtcaga tcctagcgtc gaaccacctc tgagtcagga aaccttttca       60
gacctgtgga aattgcttcc tgaaaacaac gttctgtccc cattgcctag tcaagcaatg      120
gatgatttga tgctgtcccc agacgatatt gaacaatggt tcactgaaga tccaggccca      180
gatgaagctc cacgaatgcc agaggccgct ccaccggttg ccccagcacc agcagctcct      240
```

```
acaccggcgg ccccagctcc ggccccatcc tggcctctgt catcttctgt cccttcccag        300
aaaacctacc agggcagcta cggtttccgt ctgggcttct tgcattctgg aactgccaag        360
tctgttactt gtacgtactc tccagcccct aacaagatgt tttgccaact cgcgaagacc        420
tgcccagtcc aactgtgggt cgactccacc cctccacctg gtacacgtgt ccgcgcaatg        480
gccatctaca agcagagcca gcacatgacg gaggtcgtac gacgctgtcc acaccatgag        540
cgctgctcag attctgatgg tctggcgcca ccacagcatc ttatccgagt ggaaggtaac        600
ctacgcgtgg agtatctaga tgaccgcaac acttttcgac acagtgtggt ggtgccatat        660
gagccaccag aagttggctc tgactgcacc accatccact acaactatat gtgtaacagt        720
tcatgcatgg gcggcatgaa ccggcggccg atcctgacca tcatcactct cgaggattcc        780
tcaggtaatc tcctaggacg gaattccttt gaggtgctcg tttgtgcatg cccgggccgc        840
gatcgccgga ccgaagagga gaatctccgg aagaaggtg agcctcacca cgagctgcca        900
ccaggaagca ctaagcgagc actgccaaac aacaccagca gttctccaca gccaaagaag        960
aaacctttgg acgagaata tttcacccct cagatccgtg gccgtgagcg gttcgagatg       1020
ttccgagagc tgaatgaggc cttagaactt aaggatgccc aggctggtaa ggagccagga       1080
ggcagccgtg ctcatagcag ccacctgaag tccaaaaagg gtcagtctac ctcccgccat       1140
aaaaaactga tgttcaagac cgaaggtcct gactcagact ga                         1182

<210> SEQ ID NO 17
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 17
atggaagaac cacagtcaga tcctagcgtc gaaccacctc tgagtcagga aacctttca         60 gacctgtgga aattgcttcc tgaaaacaac gttctgtccc cattgcctag tcaagcaatg       120
gatgatttga tgctgtcccc agacgatatt gaacaatggt tcactgaaga tccaggccca       180
gatgaagctc cacgaatgcc agaggccgct ccaccggttg ccccagcacc agcagctcct       240
acaccggcgg ccccagctcc ggccccatcc tggcctctgt catcttctgt cccttcccag       300
aaaacctacc agggcagcta cggtttccgt ctgggcttct tgcattctgg aactgccaag       360
tctgttactt gtacgtactc tccagcccct aacaagatgt tttgccaact cgcgaagacc       420
tgcccagtcc aactgtgggt cgactccacc cctccacctg gtacacgtgt ccgcgcaatg       480
gccatctaca agcagagcca gcacatgacg gaggtcgtac gacgctgtcc acaccatgag       540
cgctgctcag attctgatgg tctggcgcca ccacagcatc ttatccgagt ggaaggtaac       600
ctacgcgtgg agtatctaga tgaccgcaac acttttcgac acagtgtggt ggtgccatat       660
gagccaccag aagttggctc tgactgcacc accatccact acaactatat gtgtaacagt       720
tcatgcatgg gcggcatgaa ccggcggccg atcctgacca tcatcactct cgaggattcc       780
tcaggtaatc tcctaggacg gaattccttt gaggtgcgtg tttgtgcatg cccgggccgc       840
gatcgccgga ccaaggagga gaatctccgg aagaaggtg agcctcacca cgagctgcca        900
ccaggaagca ctaagcgagc actgccaaac aacaccagca gttctccaca gccaaagaag       960
aaacctttgg acgagaata tttcacccct cagatccgtg gccgtgagcg gttcgagatg      1020
ttccgagagc tgaatgaggc cttagaactt aaggatgccc aggctggtaa ggagccagga      1080
```

```
ggcagccgtg ctcatagcag ccacctgaag tccaaaaagg gtcagtctac ctcccgccat    1140
aaaaaactga tgttcaagac cgaaggtcct gactcagact ga                       1182

<210> SEQ ID NO 18
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 18
atggaagaac cacagtcaga tcctagcgtc gaaccacctc tgagtcagga aacctttca      60 gacctgtgga aattgcttcc tgaaaacaac gttctgtccc cattgcctag tcaagcaatg    120
gatgatttga tgctgtcccc agacgatatt gaacaatggt tcactgaaga tccaggccca    180
gatgaagctc cacgaatgcc agaggccgct ccaccggttg ccccagcacc agcagctcct    240
acaccggcgg ccccagctcc ggccccatcc tggcctctgt catcttctgt cccttcccag    300
aaaacctacc agggcagcta cggtttccgt ctgggcttct tgcattctgg aactgccaag    360
tctgttactt gtacgtactc tccagccctt aacaagatgt tttgccaact cgcgaagacc    420
tgcccagtcc aactgtgggt cgactccacc cctccacctg gtacacgtgt ccgcgcaatg    480
gccatctaca gcagagcca gcacatgacg gaggtcgtac gacgctgtcc acaccatgag    540
cgctgctcag attctgatgg tctggcgcca ccacagcatc ttatccgagt ggaaggtaac    600
ctacgcgtgg agtatctaga tgaccgcaac acttttcgac acagtgtggt ggtgccatat    660
gagccaccag aagttggctc tgactgcacc accatccact acaactatat gtgtaacagt    720
tcatgcatgg gagacatgaa ccggcggccg atcctgacca tcatcactct cgaggattcc    780
tcaggtaatc tcctaggacg gaattccttt gaggtgcgtg tttgtgcatg cccgggccgc    840
gatcgccgga ccgaagagga gaatctccgg aagaaggtg agcctcacca cgagctgcca    900
ccaggaagca ctaagcgagc actgccaaac aacaccagca gttctccaca gccaaagaag    960
aaacctttgg acgagaata tttcacccctt cagatccgtg gccgtgagcg gttcgagatg   1020
ttccgagagc tgaatgaggc cttagaactt aaggatgccc aggctggtaa ggagccagga   1080
ggcagccgtg ctcatagcag ccacctgaag tccaaaaagg gtcagtctac ctcccgccat   1140
aaaaaactga tgttcaagac cgaaggtcct gactcagact ga                     1182

<210> SEQ ID NO 19
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 19
atggaagaac cacagtcaga tcctagcgtc gaaccacctc tgagtcagga aacctttca      60 gacctgtgga aattgcttcc tgaaaacaac gttctgtccc cattgcctag tcaagcaatg    120
gatgatttga tgctgtcccc agacgatatt gaacaatggt tcactgaaga tccaggccca    180
gatgaagctc cacgaatgcc agaggccgct ccaccggttg ccccagcacc agcagctcct    240
acaccggcgg ccccagctcc ggccccatcc tggcctctgt catcttctgt cccttcccag    300
aaaacctacc agggcagcta cggtttccgt ctgggcttct tgcattctgg aactgccaag    360
tctgttactt gtacgtactc tccagccctt aacaagatgt tttgccaact cgcgaagacc    420
tgcccagtcc aactgtgggt cgactccacc cctccacctg gtacacgtgt ccgcgcaatg    480
```

```
gccatctaca agcagagcca gcacatgacg gaggtcgtac gacgctgtcc acaccgtgag    540
cgctgctcag attctgatgg tctggcgcca ccacagcatc ttatccgagt ggaaggtaac    600
ctacgcgtgg agtatctaga tgaccgcaac acttttcgac acagtgtggt ggtgccatat    660
gagccaccag aagttggctc tgactgcacc accatccact acaactatat gtgtaacagt    720
tcatgcatgg gcggcatgaa ccggcggccg atcctgacca tcatcactct cgaggattcc    780
tcaggtaatc tcctaggacg gaattccttt gaggtgcgtg tttgtgcatg cccgggccgc    840
gatcgccgga ccgaagagga gaatctccgg aagaaaggtg agcctcacca cgagctgcca    900
ccaggaagca ctaagcgagc actgccaaac aacaccagca gttctccaca gccaaagaag    960
aaacctttgg acgagaata tttcacccctt cagatccgtg gccgtgagcg gttcgagatg   1020
ttccgagagc tgaatgaggc cttagaactt aaggatgccc aggctggtaa ggagccagga   1080
ggcagccgtg ctcatagcag ccacctgaag tccaaaaagg gtcagtctac ctcccgccat   1140
aaaaaactga tgttcaagac cgaaggtcct gactcagact ga                       1182
```

<210> SEQ ID NO 20
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 20

```
atggaagaac cacagtcaga tcctagcgtc gaaccacctc tgagtcagga aacctttca    60 gacctgtgga aattgcttcc tgaaaacaac gttctgtccc cattgcctag tcaagcaatg    120
gatgatttga tgctgtcccc agacgatatt gaacaatggt tcactgaaga tccaggccca    180
gatgaagctc cacgaatgcc agaggccgct ccaccggttg ccccagcacc agcagctcct    240
acaccggcgg ccccagctcc ggccccatcc tggcctctgt catcttctgt cccttcccag    300
aaaacctacc agggcagcta cggtttccgt ctgggcttct gcattctgg aactgccaag    360 tctgttactt gtacgtactc tccagcccctt aacaagatgt tttgccaact cgcgaagacc    420
tgcccagtcc aactgtgggt cgactccacc cctccacctg gtacacgtgt ccgcgcaatg    480
gccatctgca agcagagcca gcacatgacg gaggtcgtac gacgctgtcc acaccatgag    540
cgctgctcag attctgatgg tctggcgcca ccacagcatc ttatccgagt ggaaggtaac    600
ctacgcgtgg agtatctaga tgaccgcaac acttttcgac acagtgtggt ggtgccatat    660
gagccaccag aagttggctc tgactgcacc accatccact acaactatat gtgtaacagt    720
tcatgcatgg gcggcatgaa ccggcggccg atcctgacca tcatcactct cgaggattcc    780
tcaggtaatc tcctaggacg gaattccttt gaggtgcgtg tttgtgcatg cccgggccgc    840
gatcgccgga ccgaagagga gaatctccgg aagaaaggtg agcctcacca cgagctgcca    900
ccaggaagca ctaagcgagc actgccaaac aacaccagca gttctccaca gccaaagaag    960
aaacctttgg acgagaata tttcacccctt cagatccgtg gccgtgagcg gttcgagatg   1020
ttccgagagc tgaatgaggc cttagaactt aaggatgccc aggctggtaa ggagccagga   1080
ggcagccgtg ctcatagcag ccacctgaag tccaaaaagg gtcagtctac ctcccgccat   1140
aaaaaactga tgttcaagac cgaaggtcct gactcagact ga                       1182
```

<210> SEQ ID NO 21
<211> LENGTH: 1182
<212> TYPE: DNA

<213> ORGANISM: Artificial Sequence
<220> FEATURE:
<223> OTHER INFORMATION: Produced by genetic engineering

<400> SEQUENCE: 21

| | |
|---|---|
| atggaagaac cacagtcaga tcctagcgtc gaaccacctc tgagtcagga aacctttca | 60 |
| gacctgtgga aattgcttcc tgaaaacaac gttctgtccc cattgcctag tcaagcaatg | 120 |
| gatgatttga tgctgtcccc agacgatatt gaacaatggt tcactgaaga tccaggccca | 180 |
| gatgaagctc cacgaatgcc agaggccgct ccaccggttg ccccagcacc agcagctcct | 240 |
| acaccggcgg ccccagctcc ggccccatcc tggcctctgt catcttctgt ccttcccag | 300 |
| aaaacctacc agggcagcta cggtttccgt ctgggcttct tgcattctgg aactgccaag | 360 |
| tctgttactt gtacgtactc tccagccctt aacaagatgt tttgccaact cgcgaagacc | 420 |
| tgcccagtcc aactgtgggt cgactccacc cctccacctg tacacgtgt ccgcgcaatg | 480 |
| gccatctaca gcagagcca gcacatgacg gaggtcgtac gacgctgtcc acaccatgag | 540 |
| cgctgctcag attctgatgg tctggcgcca ccacagcatc ttatccgagt ggaaggtaac | 600 |
| ctacgcgtgg agtgcctaga tgaccgcaac acttttcgac acagtgtggt ggtgccatat | 660 |
| gagccaccag aagttggctc tgactgcacc accatccact acaactatat gtgtaacagt | 720 |
| tcatgcatgg gcggcatgaa ccggcggccg atcctgacca tcatcactct cgaggattcc | 780 |
| tcaggtaatc tcctaggacg gaattccttt gaggtgcgtg tttgtgcatg cccgggccgc | 840 |
| gatcgccgga ccgaagagga gaatctccgg aagaaggtg agcctcacca cgagctgcca | 900 |
| ccaggaagca ctaagcgagc actgccaaac aacaccagca gttctccaca gccaaagaag | 960 |
| aaacctttgg acgagaata tttcacccctt cagatccgtg gccgtgagcg gttcgagatg | 1020 |
| ttccgagagc tgaatgaggc cttagaactt aaggatgccc aggctggtaa ggagccagga | 1080 |
| ggcagccgtg ctcatagcag ccacctgaag tccaaaaagg gtcagtctac ctcccgccat | 1140 |
| aaaaaactga tgttcaagac cgaaggtcct gactcagact ga | 1182 |

<210> SEQ ID NO 22
<211> LENGTH: 1181
<212> TYPE: DNA
<213> ORGANISM: Artificial Sequence
<220> FEATURE:
<223> OTHER INFORMATION: Produced by genetic engineering

<400> SEQUENCE: 22

| | |
|---|---|
| tggaagaacc acagtcagat cctagcgtcg aaccacctct gagtcaggaa accttttcag | 60 |
| acctgtggaa attgcttcct gaaaacaacg ttctgtcccc attgcctagt caagcaatgg | 120 |
| atgatttgat gctgtcccca gacgatattg aacaatggtt cactgaagat ccaggcccag | 180 |
| atgaagctcc acgaatgcca gaggccgctc caccggttgc cccagcacca gcagctccta | 240 |
| caccggcggc cccagctccg gccccatcct ggcctctgtc atcttctgtc cttcccaga | 300 |
| aaacctacca gggcagctac ggtttccgtc tgggcttctt gcattctgga actgccaagt | 360 |
| ctgttacttg tacgtactct ccagcccctta acaagatgtt ttgccaactc gcgaagacct | 420 |
| gcccagtcca actgtgggtc gactccaccc ctccacctgg tacacgtgtc ctcgcgatgg | 480 |
| ccatctacaa gcagagccag cacatgacgg aggtcgtacg acgctgtcca caccatgagc | 540 |
| gctgctcaga ttctgatggt ctggcgccac cacagcatct tatccgagtg aaggtaacc | 600 |
| tacgcgtgga gtgcctagat gaccgcaaca cttttcgaca cagtgtggtg gtgccatatg | 660 |
| agccaccaga agttggctct gactgcacca ccatccacta caactatatg tgtaacagtt | 720 |

| catgcatggg cggcatgaac cggcggccga tcctgaccat catcactctc gaggattcct | 780 |
| caggtaatct cctaggacgg aattcctttg aggtgcgtgt tgtgcatgc ccgggccgcg | 840 |
| atcgccggac cgaagaggag aatctccgga agaaaggtga gcctcaccac gagctgccac | 900 |
| caggaagcac taagcgagca ctgccaaaca acaccagcag ttctccacag ccaaagaaga | 960 |
| aacctttgga cggagaatat ttcacccttc agatccgtgg ccgtgagcgg ttcgagatgt | 1020 |
| tccgagagct gaatgaggcc ttagaactta aggatgccca ggctggtaag gagccaggag | 1080 |
| gcagccgtgc tcatagcagc cacctgaagt ccaaaaaggg tcagtctacc tcccgccata | 1140 |
| aaaaactgat gttcaagacc gaaggtcctg actcagactg a | 1181 |

<210> SEQ ID NO 23
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 23

| atggaagaac cacagtcaga tcctagcgtc gaaccacctc tgagtcagga aaccttttca | 60 |
| gacctgtgga aattgcttcc tgaaaacaac gttctgtccc cattgcctag tcaagcaatg | 120 |
| gatgatttga tgctgtcccc agacgatatt gaacaatggt tcactgaaga tccaggccca | 180 |
| gatgaagctc cacgaatgcc agaggccgct ccaccggttg ccccagcacc agcagctcct | 240 |
| acaccggcgg cccccagctcc ggccccatcc tggcctctgt catcttctgt cccttcccag | 300 |
| aaaacctacc agggcagcta cggttttccgt ctgggcttct tgcattctgg aactgccaag | 360 |
| tctgttactt gtacgtactc tccagccctt aacaagatgt tttgccaact cgcgaagacc | 420 |
| tgcccagtcc aactgtgggt cgactccacc cctccacctg gtacacgtgt ccgcgcaatg | 480 |
| gccatctaca agcagagcca gcacatgacg gaggtcgtac gacgctgtcc acaccatgag | 540 |
| cgctgctcag attctgatgg tctggcgcca ccacagcatc ttatccgagt ggaaggtaac | 600 |
| ctacgcgtgg agtatctaga tgaccgcaac acttttcgac acagtgtggt ggtgccatat | 660 |
| gagccaccag aagttggctc tgactgcacc accatccact acaactatat gtgtaacagt | 720 |
| ttctgcatgg gcggcatgaa ccgcggccg atcctgacca tcatcactct cgaggattcc | 780 |
| tcaggtaatc tcctaggacg gaattccttt gaggtgcgtg tttgtgcatg cccgggccgc | 840 |
| gatcgccgga ccgaagagga gaatctccgg aagaaaggtg agcctcacca cgagctgcca | 900 |
| ccaggaagca ctaagcgagc actgccaaac aacaccagca gttctccaca gccaaagaag | 960 |
| aaacctttgg acgagaata tttcacccctt cagatccgtg gccgtgagcg gttcgagatg | 1020 |
| ttccgagagc tgaatgaggc cttagaactt aaggatgccc aggctggtaa ggagccagga | 1080 |
| ggcagccgtg ctcatagcag ccacctgaag tccaaaaagg gtcagtctac ctcccgccat | 1140 |
| aaaaaactga tgttcaagac cgaaggtcct gactcagact ga | 1182 |

<210> SEQ ID NO 24
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 24

| atggaagaac cacagtcaga tcctagcgtc gaaccacctc tgagtcagga aaccttttca | 60 |

```
gacctgtgga aattgcttcc tgaaaacaac gttctgtccc cattgcctag tcaagcaatg      120
gatgatttga tgctgtcccc agacgatatt gaacaatggt tcactgaaga tccaggccca      180
gatgaagctc cacgaatgcc agaggccgct ccaccggttg ccccagcacc agcagctcct      240
acaccggcgg ccccagctcc ggccccatcc tggcctctgt catcttctgt cccttcccag      300
aaaacctacc aggcagcta cggtttccgt ctgggcttct tgcattctgg aactgccaag       360
tctgttactt gtacgtactc tccagccctt aacaagatgt tttgccaact cgcgaagacc      420
tgcccagtcc aactgtgggt cgactccacc cctccacctg gtacacgtgt ccgcgcaatg      480
gccatctaca agcagagcca gcacatgacg gaggtcgtac gacgctgtcc acaccatgag      540
cgctgctcag attctgatgg tctggcgcca ccacagcatc ttatccgagt ggaaggtaac      600
ctacgcgtgg agtatctaga tgaccgcaac acttttcgac acagtgtggt ggtgccatat      660
gagccaccag aagttggctc tgactgcacc accatccact gcaactatat gtgtaacagt      720
tcatgcatgg gcggcatgaa ccggcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaaggtg agcctcacca cgagctgcca      900
ccaggaagca ctaagcgagc actgccaaac aacaccagca gttctccaca gccaaagaag      960
```

<210> SEQ ID NO 25
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 25

```
atggaagaac cacagtcaga tcctagcgtc gaaccacctc tgagtcagga aaccttttca       60
gacctgtgga aattgcttcc tgaaaacaac gttctgtccc cattgcctag tcaagcaatg      120
gatgatttga tgctgtcccc agacgatatt gaacaatggt tcactgaaga tccaggccca      180
gatgaagctc cacgaatgcc agaggccgct ccaccggttg ccccagcacc agcagctcct      240
acaccggcgg ccccagctcc ggccccatcc tggcctctgt catcttctgt cccttcccag      300
aaaacctacc aggcagcta cggtttccgt ctgggcttct tgcattctgg aactgccaag       360
tctgttactt gtacgtactc tccagccctt aacaagatgt tttgccaact cgcgaagacc      420
tgcccagtcc aactgtgggt cgactccacc cctccacctg gtacacgtgt ccgcgcaatg      480
gccatctaca agcagagcca gcacatgacg gaggtcgtac gacgctgtcc acaccatgag      540
cgctgctcag attctgatgg tctggcgcca ccacagcatc ttatccgagt ggaaggtaac      600
ctacgcgtgg agtatctaga tgaccgcaac acttttcgac acagtgtggt ggtgccatat      660
gagccaccag aagttggctc tgactgcacc accatccact gcaactatat gtgtaacagt      720
tcatgcatgg gctgcatgaa ccggcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaaggtg agcctcacca cgagctgcca      900
ccaggaagca ctaagcgagc actgccaaac aacaccagca gttctccaca gccaaagaag      960
```

```
aaacctttgg acggagaata tttcacccct cagatccgtg gccgtgagcg gttcgagatg      1020
ttccgagagc tgaatgaggc cttagaactt aaggatgccc aggctggtaa ggagccagga      1080
ggcagccgtg ctcatagcag ccacctgaag tccaaaaagg gtcagtctac ctcccgccat      1140
aaaaaactga tgttcaagac cgaaggtcct gactcagact ga                         1182
```

<210> SEQ ID NO 26
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 26

```
atggaagaac cacagtcaga tcctagcgtc gaaccacctc tgagtcagga aacctttca       60 gacctgtgga aattgcttcc tgaaaacaac gttctgtccc cattgcctag tcaagcaatg      120
gatgatttga tgctgtcccc agacgatatt gaacaatggt tcactgaaga tccaggccca      180
gatgaagctc cacgaatgcc agaggccgct ccaccggttg ccccagcacc agcagctcct      240
acaccggcgg ccccagctcc ggccccatcc tggcctctgt catcttctgt cccttcccag      300
aaaacctacc aggcagcta cggtttccgt ctgggcttct tgcattctgg aactgccaag      360
tctgttactt gtacgtactc tccagccctt aacaagatgt tttgccaact cgcgaagacc      420
tgcccagtcc aactgtgggt cgactccacc cctccacctg gtacgcgtgt gcacgcaatg      480
gccatctaca agcagagcca gcacatgacg gaggtcgtac gacgctgtcc acaccatgag      540
cgctgctcag attctgatgg tctggcgcca ccacagcatc ttatccgagt ggaaggtaac      600
ctacgcgtgg agtatctaga tgaccgcaac acttttcgac acagtgtggt ggtgccatat      660
gagccaccag aagttggctc tgactgcacc accatccact acaactatat gtgtaacagt      720
tcatgcatgg gcggcatgaa ccgcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaaggtg agcctcacca cgagctgcca      900
ccaggaagca ctaagcgagc actgccaaac aacaccagca gttctccaca gccaaagaag      960
aaacctttgg acggagaata tttcacccct cagatccgtg gccgtgagcg gttcgagatg      1020
ttccgagagc tgaatgaggc cttagaactt aaggatgccc aggctggtaa ggagccagga      1080
ggcagccgtg ctcatagcag ccacctgaag tccaaaaagg gtcagtctac ctcccgccat      1140
aaaaaactga tgttcaagac cgaaggtcct gactcagact ga                         1182
```

<210> SEQ ID NO 27
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 27

```
atggaagaac cacagtcaga tcctagcgtc gaaccacctc tgagtcagga aacctttca       60 gacctgtgga aattgcttcc tgaaaacaac gttctgtccc cattgcctag tcaagcaatg      120
gatgatttga tgctgtcccc agacgatatt gaacaatggt tcactgaaga tccaggccca      180
gatgaagctc cacgaatgcc agaggccgct ccaccggttg ccccagcacc agcagctcct      240
acaccggcgg ccccagctcc ggccccatcc tggcctctgt catcttctgt cccttcccag      300
```

| | |
|---|---|
| aaaacctacc agggcagcta cggtttccgt ctgggcttct tgcattctgg aactgccaag | 360 |
| tctgttactt gtacgtactc tccagcccttt aacaagatgt tttgccaact cgcgaagacc | 420 |
| tgcccagtcc aactgtgggt cgactccacc cctccacctg gtacacgtgt ccgcgcaatg | 480 |
| gccatctaca agcagagcca gcacatgacg gaggtcgtac gacgctgtcc acaccatgag | 540 |
| cgctgctcag attctgatgg tctggcgcca ccacagcatc ttatccgagt ggaaggtaac | 600 |
| ctacgcgtgg agtatctaga tgaccgcaac acttttcgac acagtgtggt ggtgccatat | 660 |
| gagccaccag aagttggctc tgactgcacc accatccact acaactatat gtgtaacagt | 720 |
| tcatgcatgg gcggcatgaa cctgaggccg atcctgacca tcatcactct cgaggattcc | 780 |
| tcaggtaatc tcctaggacg gaattccttt gaggtgcgtg tttgtgcatg cccgggccgc | 840 |
| gatcgccgga ccgaagagga gaatctccgg aagaaaggtg agcctcacca cgagctgcca | 900 |
| ccaggaagca ctaagcgagc actgccaaac aacaccagca gttctccaca gccaaagaag | 960 |
| aaaccttttgg acgagaata tttcacccttt cagatccgtg gccgtgagcg gttcgagatg | 1020 |
| ttccgagagc tgaatgaggc cttagaactt aaggatgccc aggctggtaa ggagccagga | 1080 |
| ggcagccgtg ctcatagcag ccacctgaag tccaaaaagg gtcagtctac ctcccgccat | 1140 |
| aaaaaactga tgttcaagac cgaaggtcct gactcagact ga | 1182 |

<210> SEQ ID NO 28
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 28

| | |
|---|---|
| atggaagaac cacagtcaga tcctagcgtc gaaccacctc tgagtcagga aacctttttca | 60 |
| gacctgtgga aattgcttcc tgaaaacaac gttctgtccc cattgcctag tcaagcaatg | 120 |
| gatgatttga tgctgtcccc agacgatatt gaacaatggt tcactgaaga tccaggccca | 180 |
| gatgaagctc cacgaatgcc agaggccgct ccaccggttg ccccagcacc agcagctcct | 240 |
| acaccggcgg ccccagctcc ggccccatcc tggcctctgt catcttctgt cccttcccag | 300 |
| aaaacctacc agggcagcta cggtttccgt ctgggcttct tgcattctgg aactgccaag | 360 |
| tctgttactt gtacgtactc tccagcccttt aacaagatgt tttgccaact cgcgaagacc | 420 |
| tgcccagtcc aactgtgggt cgactccacc cctccacctg gtacacgtgt ccgcgcaatg | 480 |
| gccatctaca agcagagcca gcacatgacg gaggtcgtac gacgctgtcc acactacgag | 540 |
| cgctgctcag attctgatgg tctggcgcca ccacagcatc ttatccgagt ggaaggtaac | 600 |
| ctacgcgtgg agtatctaga tgaccgcaac acttttcgac acagtgtggt ggtgccatat | 660 |
| gagccaccag aagttggctc tgactgcacc accatccact acaactatat gtgtaacagt | 720 |
| tcatgcatgg gcggcatgaa ccggcggccg atcctgacca tcatcactct cgaggattcc | 780 |
| tcaggtaatc tcctaggacg gaattccttt gaggtgcgtg tttgtgcatg cccgggccgc | 840 |
| gatcgccgga ccgaagagga gaatctccgg aagaaaggtg agcctcacca cgagctgcca | 900 |
| ccaggaagca ctaagcgagc actgccaaac aacaccagca gttctccaca gccaaagaag | 960 |
| aaaccttttgg acgagaata tttcacccttt cagatccgtg gccgtgagcg gttcgagatg | 1020 |
| ttccgagagc tgaatgaggc cttagaactt aaggatgccc aggctggtaa ggagccagga | 1080 |
| ggcagccgtg ctcatagcag ccacctgaag tccaaaaagg gtcagtctac ctcccgccat | 1140 |
| aaaaaactga tgttcaagac cgaaggtcct gactcagact ga | 1182 |

<210> SEQ ID NO 29
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 29

| | |
|---|---|
| atggaagaac cacagtcaga tcctagcgtc gaaccacctc tgagtcagga aacctttca | 60 |
| gacctgtgga aattgcttcc tgaaaacaac gttctgtccc cattgcctag tcaagcaatg | 120 |
| gatgatttga tgctgtcccc agacgatatt gaacaatggt tcactgaaga tccaggccca | 180 |
| gatgaagctc cacgaatgcc agaggccgct ccaccggttg ccccagcacc agcagctcct | 240 |
| acaccggcgg ccccagctcc ggccccatcc tggcctctgt catcttctgt cccttcccag | 300 |
| aaaacctacc agggcagcta cggtttccgt ctgggcttct gcattctggg aactgccaag | 360 |
| tctgttactt gtacgtactc tccagccctt aacaagatgt tttgccaact cgcgaagacc | 420 |
| tgcccagtcc aactgtgggt cgactccacc cctccacctg gtacacgtgt ccgcgcaatg | 480 |
| gccatctaca agcagagcca gcacatgacg gaggtcgtac gacgctgtcc acaccatgag | 540 |
| cgctgctcag attctgatgg tctggcgcca ccacagcatc ttatccgagt ggaaggtaac | 600 |
| ctacgcgtgg agtatctaga tgaccgcaac acttttcgac acagtgtggt ggtgccatat | 660 |
| gagccaccag aagttggctc tgactgcacc accatccact acaactatat gtgtaacagt | 720 |
| tcatgcatgg gcggcatgaa ccggcggccg atcctgacca tcatcactct cgaggattcc | 780 |
| tcaggtaatc tcctaggacg gaattccttt gaggtgcgtg tttgtgcatg cccgggtacc | 840 |
| gatcgccgga ccgaagagga gaatctccgg aagaaaggtg agcctcacca cgagctgcca | 900 |
| ccaggaagca ctaagcgagc actgccaaac aaccagcag ttctccaca gccaaagaag | 960 |
| aaacctttgg acggagaata tttcaccctt cagatccgtg gccgtgagcg gttcgagatg | 1020 |
| ttccgagagc tgaatgaggc cttagaactt aaggatgccc aggctggtaa ggagccagga | 1080 |
| ggcagccgtg ctcatagcag ccacctgaag tccaaaaagg gtcagtctac ctcccgccat | 1140 |
| aaaaaactga tgttcaagac cgaaggtcct gactcagact ga | 1182 |

<210> SEQ ID NO 30
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 30

| | |
|---|---|
| atggaagaac cacagtcaga tcctagcgtc gaaccacctc tgagtcagga aacctttca | 60 |
| gacctgtgga aattgcttcc tgaaaacaac gttctgtccc cattgcctag tcaagcaatg | 120 |
| gatgatttga tgctgtcccc agacgatatt gaacaatggt tcactgaaga tccaggccca | 180 |
| gatgaagctc cacgaatgcc agaggccgct ccaccggttg ccccagcacc agcagctcct | 240 |
| acaccggcgg ccccagctcc ggccccatcc tggcctctgt catcttctgt cccttcccag | 300 |
| aaaacctacc agggcagcta cggtttccgt ctgggcttct gcattctggg aactgccaag | 360 |
| tctgttactt gtacgtactc tccagccctt aacaagatgt tttgccaact cgcgaagacc | 420 |
| tgcccagtcc aactgtgggt cgactccacg tccccacctg gtacacgtgt ccgcgcaatg | 480 |
| gccatctaca agcagagcca gcacatgacg gaggtcgtac gacgctgtcc acaccatgag | 540 |

```
cgctgctcag attctgatgg tctggcgcca ccacagcatc ttatccgagt ggaaggtaac      600
ctacgcgtgg agtatctaga tgaccgcaac acttttcgac acagtgtggt ggtgccatat      660
gagccaccag aagttggctc tgactgcacc accatccact acaactatat gtgtaacagt      720
tcatgcatgg gcggcatgaa ccggcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaaggtg agcctcacca cgagctgcca      900
ccaggaagca ctaagcgagc actgccaaac aacaccagca gttctccaca gccaaagaag      960 aaaccttttgg acgagaata tttcacccctt cagatccgtg gccgtgagcg gttcgagatg     1020
ttccgagagc tgaatgaggc cttagaactt aaggatgccc aggctggtaa ggagccagga     1080
ggcagccgtg ctcatagcag ccacctgaag tccaaaaagg gtcagtctac ctcccgccat     1140
aaaaaactga tgttcaagac cgaaggtcct gactcagact ga                        1182
```

<210> SEQ ID NO 31
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 31

```
atggaagaac cacagtcaga tcctagcgtc gaaccacctc tgagtcagga aacctttttca      60 gacctgtgga aattgcttcc tgaaaacaac gttctgtccc cattgcctag tcaagcaatg     120
gatgatttga tgctgtcccc agacgatatt gaacaatggt tcactgaaga tccaggccca     180
gatgaagctc cacagaatgcc agaggccgct ccaccggttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagccctt aacaagatgt tttgccaact cgcgaagacg     420
tacccagtcc aactgtgggt cgactccacc cctccacctg gtacacgtgt ccgcgcaatg     480
gccatctaca agcagagcca gcacatgacg gaggtcgtac gacgctgtcc acaccatgag     540
cgctgctcag attctgatgg tctggcgcca ccacagcatc ttatccgagt ggaaggtaac     600
ctacgcgtgg agtatctaga tgaccgcaac acttttcgac acagtgtggt ggtgccatat     660
gagccaccag aagttggctc tgactgcacc accatccact acaactatat gtgtaacagt     720
tcatgcatgg gcggcatgaa ccggcggccg atcctgacca tcatcactct cgaggattcc     780
tcaggtaatc tcctaggacg gaattccttt gaggtgcgtg tttgtgcatg cccgggccgc     840
gatcgccgga ccgaagagga gaatctccgg aagaaaggtg agcctcacca cgagctgcca     900
ccaggaagca ctaagcgagc actgccaaac aacaccagca gttctccaca gccaaagaag     960 aaaccttttgg acgagaata tttcacccctt cagatccgtg gccgtgagcg gttcgagatg    1020
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                       1182
```

<210> SEQ ID NO 32
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 32

```
atggaagaac cacagtcaga tcctagcgtc gaaccacctc tgagtcagga aacctttca      60
gacctgtgga aattgcttcc tgaaaacaac gttctgtccc cattgcctag tcaagcaatg    120
gatgatttga tgctgtcccc agacgatatt gaacaatggt tcactgaaga tccaggccca   180
gatgaagctc cacgaatgcc agaggccgct ccaccggttg ccccagcacc agcagctcct   240
acaccggcgg ccccagctcc ggccccatcc tggcctctgt catcttctgt cccttcccag   300
aaaacctacc aggcagcta cggtttccgt ctgggcttct tgcattctgg aactgccaag    360
tctgttactt gtacgtactc tccagcccct aacaagatgt tttgccaact cgcgaagacc   420
tgcccagtcc aactgtgggt cgactccacc cctccacctg gtacacgtgt ccgcgcaatg   480
gccatctaca agcagagcca gcacatgacg gaggtcgtac gacgctgtcc acaccatgag   540
cgctgctcag attctgatgg tctggcgcca ccacagcatc ttatccgagt ggaaggtaac   600
ctacgcgtgg agtatctaga tgaccgcaac acttttcgac acagtgtggt ggtgccatat   660
gagccaccag aagttggctc tgactgcacc accatccact acaactatat gtgtaacagt   720
tcatgcatgg gcggcatgaa ccggatgccg atcctgacca tcatcactct cgaggattcc   780
tcaggtaatc tcctaggacg gaattccttt gaggtgcgtg tttgtgcatg cccgggccgc   840
gatcgccgga ccgaagagga gaatctccgg aagaaaggtg agcctcacca cgagctgcca   900
ccaggaagca ctaagcgagc actgccaaac aacaccagca gttctccaca gccaaagaag   960
aaacctttgg acggagaata tttcacccct cagatccgtg gccgtgagcg gttcgagatg   1020
ttccgagagc tgaatgaggc cttagaactt aaggatgccc aggctggtaa ggagccagga   1080
ggcagccgtg ctcatagcag ccacctgaag tccaaaaagg gtcagtctac ctcccgccat   1140
aaaaaactga tgttcaagac cgaaggtcct gactcagact ga                      1182
```

<210> SEQ ID NO 33
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 33

```
atggaagaac cacagtcaga tcctagcgtc gaaccacctc tgagtcagga aacctttca      60
gacctgtgga aattgcttcc tgaaaacaac gttctgtccc cattgcctag tcaagcaatg    120
gatgatttga tgctgtcccc agacgatatt gaacaatggt tcactgaaga tccaggccca   180
gatgaagctc cacgaatgcc agaggccgct ccaccggttg ccccagcacc agcagctcct   240
acaccggcgg ccccagctcc ggccccatcc tggcctctgt catcttctgt cccttcccag   300
aaaacctacc aggcagcta cggtttccgt ctgggcttct tgcattctgg aactgccaag    360
tctgttactt gtacgtactc tccagcccct aacaagatgt tttgccaact cgcgaagacc   420
tgcccagtcc aactgtgggt cgactccacc cctccacctg gtacacgtgt ccgcgcaatg   480
gccatctaca agcagagcca gcacatgacg gaggtcgtac gacgctgtcc acaccatgag   540
cgctgctcag attctgatgg tctggcgcca ccacagcatc ttatccgagt ggaaggtaac   600
ctacgcgtgg agtatctaga tgaccgcaac acttttcgac acagtgtggt ggtgccatat   660
gagccaccag aagttggctc tgactgcacc accatccact acaactatat gtgtaacagt   720
tcatgcatgg gcggcatgaa ccggcggccg atcctgacca tcatcactct cgaggattcc   780
```

```
tcaggtaatc tcctaggacg gaattccttt gaggtgcgtg tttgtgcatg cagcggccgc      840
gatcgccgga ccgaagagga gaatctccgg aagaaaggtg agcctcacca cgagctgcca      900
ccaggaagca ctaagcgagc actgccaaac aacaccagca gttctccaca gccaaagaag      960
aaacctttgg acggagaata tttcacccct cagatccgtg gccgtgagcg gttcgagatg     1020
ttccgagagc tgaatgaggc cttagaactt aaggatgccc aggctggtaa ggagccagga     1080
ggcagccgtg ctcatagcag ccacctgaag tccaaaaagg gtcagtctac ctcccgccat     1140
aaaaaactga tgttcaagac cgaaggtcct gactcagact ga                       1182
```

<210> SEQ ID NO 34
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 34

```
atggaagaac cacagtcaga tcctagcgtc gaaccacctc tgagtcagga aaccttttca       60
gacctgtgga aattgcttcc tgaaaacaac gttctgtccc cattgcctag tcaagcaatg      120
gatgatttga tgctgtcccc agacgatatt gaacaatggt tcactgaaga tccaggccca      180
gatgaagctc cacgaatgcc agaggccgct ccaccggttg ccccagcacc agcagctcct      240
acaccggcgg ccccagctcc ggccccatcc tggcctctgt catcttctgt cccttcccag      300
aaaacctacc agggcagcta cggtttccgt ctgggcttct tgcattctgg aactgccaag      360
tctgttactt gtacgtactc tccagccctt aacaagatgt tttgccaact cgcgaagacc      420
tgcccagtcc aactgtgggt cgactccacc cctccacctg gtacacgtgt ccgcgcaatg      480
gccatctaca agcagagcca gcacatgacg gaggtcgtac gacgctgtcc acaccatgag      540
cgctgctcag attctgatgg tctggcgcca ccacagcatc ttatccgagt ggaaggtaac      600
ctacgcgtgg agtatctaga tgaccgcaac acttttcgac acagtgtggt ggtgccatat      660
gagccaccag aagttggctc tgactgcacc accatccact acaactatat gtgtaacagt      720
tcatgcatgg gcggcatgaa ccggcggccg atcctgacca tcatcactct cgaggattcc      780
tcaggtaatc tcctaggacg gaattccttt gagatgcgtg tttgtgcatg cccgggccgc      840
gatcgccgga ccgaagagga gaatctccgg aagaaaggtg agcctcacca cgagctgcca      900
ccaggaagca ctaagcgagc actgccaaac aacaccagca gttctccaca gccaaagaag      960
aaacctttgg acggagaata tttcacccct cagatccgtg gccgtgagcg gttcgagatg     1020
ttccgagagc tgaatgaggc cttagaactt aaggatgccc aggctggtaa ggagccagga     1080
ggcagccgtg ctcatagcag ccacctgaag tccaaaaagg gtcagtctac ctcccgccat     1140
aaaaaactga tgttcaagac cgaaggtcct gactcagact ga                       1182
```

<210> SEQ ID NO 35
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 35

```
atggaagaac cacagtcaga tcctagcgtc gaaccacctc tgagtcagga aaccttttca       60
gacctgtgga aattgcttcc tgaaaacaac gttctgtccc cattgcctag tcaagcaatg      120
gatgatttga tgctgtcccc agacgatatt gaacaatggt tcactgaaga tccaggccca      180
```

-continued

```
gatgaagctc cacgaatgcc agaggccgct ccaccggttg ccccagcacc agcagctcct      240
acaccggcgg ccccagctcc ggccccatcc tggcctctgt catcttctgt cccttcccag      300
aaaacctacc agggcagcta cggtttccgt ctgggcttct tgcattctgg aactgccaag      360
tctgttactt gtacgtactc tccagccctt aacaagatgt tttgccaact cgcgaagacc      420
tgcccagtcc aactgtgggt cgactccacc cctccacctg gtacacgtgt ccgcgcaatg      480
gccatctaca agcagagcca gcacatgacg gaggtcgtac gacgctgtcc acaccatgag      540
cgctgctcag attctgatgg tctggcgcca ccacagcatc ttatccgagt ggaaggtaac      600
ctacgcgtgg agtatctaga tgaccgcaac acttttcgac acagtgtggt ggtgccatat      660
gagccaccag aagttggctc tgactgcacc accatccact acaactatat gtgtaacagt      720
tcatgcatgg gcggcatgaa ccggcggccg atcctgacca tcatcactct cgaggattcc      780
tcaggtaatc tcctaggacg gaattccttt gaggtgcgtg tttgtgcatg cccggggccgc     840 gatcgccgga ccgaaaagga gaatctccgg aagaaggtg agcctcacca cgagctgcca      900
ccaggaagca ctaagcgagc actgccaaac aacaccagca gttctccaca gccaaagaag      960
aaacctttgg acggagaata tttcacccct cagatccgtg gccgtgagcg gttcgagatg     1020
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                        1182
```

<210> SEQ ID NO 36
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 36

```
atggaagaac cacagtcaga tcctagcgtc gaaccacctc tgagtcagga aacctttttca     60 gacctgtgga aattgcttcc tgaaaacaac gttctgtccc cattgcctag tcaagcaatg    120
gatgatttga tgctgtcccc agacgatatt gaacaatggt tcactgaaga tccaggccca    180
gatgaagctc cacgaatgcc agaggccgct ccaccggttg ccccagcacc agcagctcct    240
acaccggcgg ccccagctcc ggccccatcc tggcctctgt catcttctgt cccttcccag    300
aaaacctacc agggcagcta cggtttccgt ctgggcttct tgcattctgg aactgccaag    360
tctgttactt gtacgtactc tccagccctt aacaagatgt tttgccaact cgcgaagacc    420
tgcccagtcc aactgtgggt cgactccacc cctccacctg gtacacgtgt ccgcgcaatg    480
gccatctaca agcagagcca gcacatgacg gaggtcctgc gacgctgtcc acaccatgag    540
cgctgctcag attctgatgg tctggcgcca ccacagcatc ttatccgagt ggaaggtaac    600
ctacgcgtgg agtatctaga tgaccgcaac acttttcgac acagtgtggt ggtgccatat    660
gagccaccag aagttggctc tgactgcacc accatccact acaactatat gtgtaacagt    720
tcatgcatgg gcggcatgaa ccggcggccg atcctgacca tcatcactct cgaggattcc    780
tcaggtaatc tcctaggacg gaattccttt gaggtgcgtg tttgtgcatg cccggggccgc   840 gatcgccgga ccgaagagga gaatctccgg aagaaggtg agcctcacca cgagctgcca    900
ccaggaagca ctaagcgagc actgccaaac aacaccagca gttctccaca gccaaagaag    960
aaacctttgg acggagaata tttcacccct cagatccgtg gccgtgagcg gttcgagatg   1020
```

```
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                      1182
```

<210> SEQ ID NO 37
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 37

```
atggaagaac cacagtcaga tcctagcgtc gaaccacctc tgagtcagga aaccttttca    60
gacctgtgga aattgcttcc tgaaaacaac gttctgtccc cattgcctag tcaagcaatg    120
gatgatttga tgctgtcccc agacgatatt gaacaatggt tcactgaaga tccaggccca    180
gatgaagctc cacgaatgcc agaggccgct ccaccggttg ccccagcacc agcagctcct    240
acaccggcgg ccccagctcc ggccccatcc tggcctctgt catcttctgt cccttcccag    300
aaacctaccc aggcagctac ggtttccgt ctgggcttct tgcattctgg aactgccaag    360
tctgttactt gtacgtactc tccagccctt aacaagatgt tttgccaact cgcgaagacc    420
tgcccagtcc aactgtgggt cgactccacc cctccacctg gtacacgtgt ccgcgcaatg    480
gccatctaca gcagagcca gcacatgacg gaggtcgtac gacgctgtcc acaccatgag    540
cgctgctcag attctgatgg tctggcgcca ccacagcatc ttatccgagt ggaaggtaac    600
ctacgcgtgg agtatctaga tgaccgcaac acttttcgac acagtgtggt ggtgccatat    660
gagccaccag aagttggctc tgactgcacc accatccact acaactatat gtgtaacagt    720
tcatgcatgg gcgtcatgaa ccggcggccg atcctgacca tcatcactct cgaggattcc    780
tcaggtaatc tcctaggacg gaattccttt gaggtcgtg tttgtgcatg cccgggccgc    840
gatcgccgga ccgaagagga gaatctccgg aagaaggtg agcctcacca cgagctgcca    900
ccaggaagca ctaagcgagc actgccaaac aacaccagca gttctccaca gccaaagaag    960
aaacctttgg acggagaata tttcacccct cagatccgtg gccgtgagcg gttcgagatg    1020
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                      1182
```

<210> SEQ ID NO 38
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 38

```
atggaagaac cacagtcaga tcctagcgtc gaaccacctc tgagtcagga aaccttttca    60
gacctgtgga aattgcttcc tgaaaacaac gttctgtccc cattgcctag tcaagcaatg    120
gatgatttga tgctgtcccc agacgatatt gaacaatggt tcactgaaga tccaggccca    180
gatgaagctc cacgaatgcc agaggccgct ccaccggttg ccccagcacc agcagctcct    240
acaccggcgg ccccagctcc ggccccatcc tggcctctgt catcttctgt cccttcccag    300
aaacctaccc aggcagctac ggtttccgt ctgggcttct tgcattctgg aactgccaag    360
tctgttactt gtacgtactc tccagccctt aacaagatgt tttgccaact cgcgaagacc    420
```

```
tgcccagtcc aactgtgggt cgactccacc cctccacctg gtacacgtgt ccgcgcaatg     480
gccatctaca agcagagcca gcacatgacg gaggtcgtac gacggtaccc acaccatgag     540
cgctgctcag attctgatgg tctggcgcca ccacagcatc ttatccgagt ggaaggtaac     600
ctacgcgtgg agtatctaga tgaccgcaac acttttcgac acagtgtggt ggtgccatat     660
gagccaccag aagttggctc tgactgcacc accatccact acaactatat gtgtaacagt     720
tcatgcatgg gcggcatgaa ccggcggccg atcctgacca tcatcactct cgaggattcc     780
tcaggtaatc tcctaggacg gaattccttt gaggtgcgtg tttgtgcatg cccgggccgc     840
gatcgccgga ccgaagagga gaatctccgg aagaaggtg agcctcacca cgagctgcca     900
ccaggaagca ctaagcgagc actgccaaac aacaccagca gttctccaca gccaaagaag     960
aaacctttgg acggagaata tttcacccgtt cagatccgtg gccgtgagcg gttcgagatg    1020
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                       1182
```

<210> SEQ ID NO 39
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 39

```
atggaagaac cacagtcaga tcctagcgtc gaaccacctc tgagtcagga aaccttttca     60
gacctgtgga aattgcttcc tgaaaacaac gttctgtccc cattgcctag tcaagcaatg    120
gatgatttga tgctgtcccc agacgatatt gaacaatggt tcactgaaga tccaggccca    180
gatgaagctc cacgaatgcc agaggccgct ccaccggttg ccccagcacc agcagctcct    240
acaccggcgg ccccagctcc ggccccatcc tggcctctgt catcttctgt cccttcccag    300
aaaacctacc agggcagcta cggtttccgt ctgggcttct tgcattctgg aactgccaag    360
tctgttactt gtacgtactc tccagccctt aacaagatgt tttgccaact cgcgaagacc    420
tgcccagtcc aactgtgggt cgactccacc cctccacctg gtacacgtgt ccgcgcaatg    480
gccatctaca agcagagcca gcacatgacg gaggtcgtac gacgctgtcc acaccatgag    540
cgctgctcag attctgatgg tctggcgcca ccacagcatc ttatccgagt ggaaggtaac    600
ctacgcgtgg agtatctaga tgaccgcaac acttttcgac acagtgtggt ggtgccatat    660
gagccaccag aagttggctc tgactgcacc accatccact acaactatat gtacaacagt    720
tcatgcatgg gcggcatgaa ccggcggccg atcctgacca tcatcactct cgaggattcc    780
tcaggtaatc tcctaggacg gaattccttt gaggtgcgtg tttgtgcatg cccgggccgc    840
gatcgccgga ccgaagagga gaatctccgg aagaaggtg agcctcacca cgagctgcca    900
ccaggaagca ctaagcgagc actgccaaac aacaccagca gttctccaca gccaaagaag    960
aaacctttgg acggagaata tttcacccgtt cagatccgtg gccgtgagcg gttcgagatg   1020
ttccgagagc tgaatgaggc cttagaactt aaggatgccc aggctggtaa ggagccagga   1080
ggcagccgtg ctcatagcag ccacctgaag tccaaaaagg gtcagtctac ctcccgccat   1140
aaaaaactga tgttcaagac cgaaggtcct gactcagact ga                      1182
```

<210> SEQ ID NO 40

<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 40

| | | | | | |
|---|---|---|---|---|---|
| atggaagaac | cacagtcaga | tcctagcgtc | gaaccacctc | tgagtcagga | aaccttttca | 60 |
| gacctgtgga | aattgcttcc | tgaaaacaac | gttctgtccc | cattgcctag | tcaagcaatg | 120 |
| gatgatttga | tgctgtcccc | agacgatatt | gaacaatggt | tcactgaaga | tccaggccca | 180 |
| gatgaagctc | cacgaatgcc | agaggccgct | ccaccggttg | ccccagcacc | agcagctcct | 240 |
| acaccggcgg | ccccagctcc | ggccccatcc | tggcctctgt | catcttctgt | cccttcccag | 300 |
| aaaacctacc | agggcagcta | cggtttccgt | ctgggcttct | tgcattctgg | aactgccaag | 360 |
| tctgttactt | gtacgtactc | tccagcccct | aacaagatgt | tttgccaact | cgcgaagacc | 420 |
| tgcccagtcc | aactgtgggt | cgactccacc | cctccacctg | gtacacgtgt | ccgcgcaatg | 480 |
| gccatctaca | agcagagcca | gcacatgacg | gaggtcgtac | gacgctgtcc | acaccatgag | 540 |
| cgctgctcag | attctgatgg | tctggcgcca | ccacagcatc | ttatccgagt | ggaaggtaac | 600 |
| ctacgcgtgg | agtatctaga | tgaccgcaac | acttttcgac | acagtgtggt | ggtgccatat | 660 |
| gagccaccag | aagttggctc | tgactgcacc | accatccact | acaactatat | gtgtaacagt | 720 |
| tcatgcatgg | gcggcatgaa | ccggcggccg | atcctgacca | tcatcactct | cgaggattcc | 780 |
| tcaggtaatc | tcctaggacg | gaattccttt | gaggtcgtg | tttgtgcatg | cctcggccgc | 840 |
| gatcgccgga | ccgaagagga | gaatctccgg | aagaaggtg | agcctcacca | cgagctgcca | 900 |
| ccaggaagca | ctaagcgagc | actgccaaac | aacaccagca | gttctccaca | gccaaagaag | 960 |
| aaacctttgg | acggagaata | tttcaccctt | cagatccgtg | gccgtgagcg | gttcgagatg | 1020 |
| ttccgagagc | tgaatgaggc | cttagaactt | aaggatgccc | aggctggtaa | ggagccagga | 1080 |
| ggcagccgtg | ctcatagcag | ccacctgaag | tccaaaaagg | gtcagtctac | ctcccgccat | 1140 |
| aaaaaactga | tgttcaagac | cgaaggtcct | gactcagact | ga | | 1182 |

<210> SEQ ID NO 41
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 41

| | | | | | |
|---|---|---|---|---|---|
| atggaagaac | cacagtcaga | tcctagcgtc | gaaccacctc | tgagtcagga | aaccttttca | 60 |
| gacctgtgga | aattgcttcc | tgaaaacaac | gttctgtccc | cattgcctag | tcaagcaatg | 120 |
| gatgatttga | tgctgtcccc | agacgatatt | gaacaatggt | tcactgaaga | tccaggccca | 180 |
| gatgaagctc | cacgaatgcc | agaggccgct | ccaccggttg | ccccagcacc | agcagctcct | 240 |
| acaccggcgg | ccccagctcc | ggccccatcc | tggcctctgt | catcttctgt | cccttcccag | 300 |
| aaaacctacc | agggcagcta | cggtttccgt | ctgggcttct | tgcattctgg | aactgccaag | 360 |
| tctgttactt | gtacgtactc | tccagcccct | aacaagatgt | tttgccaact | cgcgaagacc | 420 |
| tgcccagtcc | aactgtgggt | cgactccacc | cctccacctg | gtacacgtgt | ccgcgcaatg | 480 |
| gccatctaca | agcagagcca | gcacatgacg | gaggtcgtac | gacgctgtcc | acaccatgag | 540 |
| cgctgctcag | attctgatgg | tctggcgcca | ccacagcatc | ttatccgagt | ggaaggtaac | 600 |
| ctacgcgtgg | agtatctaga | tgaccgcaac | acttttcgac | acagtgtggt | ggtgccatat | 660 |

```
gagccaccag aagttggctc tgactgcacc accatccact acaactatat gtgtaacagt    720
tcatgcatgg gcggcatgaa ccggcggccg atcctgacca tcatcactct cgaggattcc    780
tcaggtaatc tcctagagcg gaattccttt gaggtgcgtg tttgtgcatg cccgggccgc    840
gatcgccgga ccgaagagga gaatctccgg aagaaggtg agcctcacca cgagctgcca    900
ccaggaagca ctaagcgagc actgccaaac aacaccagca gttctccaca gccaaagaag    960
aaacctttgg acggagaata tttcacccct cagatccgtg gccgtgagcg gttcgagatg   1020
ttccgagagc tgaatgaggc cttagaactt aaggatgccc aggctggtaa ggagccagga   1080
ggcagccgtg ctcatagcag ccacctgaag tccaaaaagg gtcagtctac ctcccgccat   1140
aaaaaactga tgttcaagac cgaaggtcct gactcagact ga                      1182
```

<210> SEQ ID NO 42
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 42

```
atggaagaac cacagtcaga tcctagcgtc gaaccacctc tgagtcagga aaccttttca     60
gacctgtgga aattgcttcc tgaaaacaac gttctgtccc cattgcctag tcaagcaatg    120
gatgatttga tgctgtcccc agacgatatt gaacaatggt tcactgaaga tccaggccca    180
gatgaagctc cacgaatgcc agaggccgct ccaccggttg ccccagcacc agcagctcct    240
acaccggcgg ccccagctcc ggccccatcc tggcctctgt catcttctgt cccttcccag    300
aaaacctacc agggcagcta cggtttccgt ctgggcttct tgcattctgg aactgccaag    360
tctgttactt gtacgtactc tccagcccct aacaagatgt tttgccaact cgcgaagacc    420
tgcccagtcc aactgtgggt cgactccacc cctccacctg gtacacgtgt ccgcgcaatg    480
gccatctaca gcagagcca gcacatgacg gaggtcgtac gacgctgtcc acaccatgag    540
cgctgctcag attctgatgg tctggcgcca ccacagcatc ttatccgagt ggaaggtaac    600
ctacgcgtgg agtatctaga tgaccgcaac acttttcgac acagtgtggt ggtgccatat    660
gagccaccag aagttggctc tgactgcacc accatccact acaactatat gtgtaacagt    720
tcatgcatgg gcggcatgaa ccggcggccg atcctgacca tcatcactct cgaggattcc    780
tcaggtaatc tcctaggacg gaattccttt gaggtgcgtg tttgtgcatg cccgggcaaa    840
gatcgccgga ccgaagagga gaatctccgg aagaaggtg agcctcacca cgagctgcca    900
ccaggaagca ctaagcgagc actgccaaac aacaccagca gttctccaca gccaaagaag    960
aaacctttgg acggagaata tttcacccct cagatccgtg gccgtgagcg gttcgagatg   1020
ttccgagagc tgaatgaggc cttagaactt aaggatgccc aggctggtaa ggagccagga   1080
ggcagccgtg ctcatagcag ccacctgaag tccaaaaagg gtcagtctac ctcccgccat   1140
aaaaaactga tgttcaagac cgaaggtcct gactcagact ga                      1182
```

<210> SEQ ID NO 43
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 43

-continued

```
atggaagaac cacagtcaga tcctagcgtc gaaccacctc tgagtcagga aaccttttca      60
gacctgtgga aattgcttcc tgaaaacaac gttctgtccc cattgcctag tcaagcaatg     120
gatgatttga tgctgtcccc agacgatatt gaacaatggt tcactgaaga tccaggccca     180
gatgaagctc cacgaatgcc agaggccgct ccaccggttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagcccct aacaagatgt tttgccaact cgcgaagacc     420
tgcccagtcc aactgtgggt cgactccacc cctccacctg tacacgtgt ccgcgcaatg      480 gccatctaca agcagagcca gcacatgacg gaggtcgtac gacgctgtcc acaccatgag     540
cgctgctcag attctgatgg tctggcgcca ccacagcatc ttatccgagt ggaaggtaac     600
ctacgcgtgg agtatctaga tgaccgcaac acttttcgaa gatctgtggt ggtgccatat     660
gagccaccag aagttggctc tgactgcacc accatccact acaactatat gtgtaacagt     720
tcatgcatgg gcggcatgaa ccggcggccg atcctgacca tcatcactct cgaggattcc     780
tcaggtaatc tcctaggacg gaattccttt gaggtgcgtg tttgtgcatg cccgggccgc     840
gatcgccgga ccgaagagga gaatctccgg aagaaggtg agcctcacca cgagctgcca      900
ccaggaagca ctaagcgagc actgccaaac aacaccagca gttctccaca gccaaagaag     960
aaacctttgg acggagaata tttcaccctt cagatccgtg gccgtgagcg gttcgagatg    1020
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                       1182
```

<210> SEQ ID NO 44
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 44

```
atggaagaac cacagtcaga tcctagcgtc gaaccacctc tgagtcagga aaccttttca      60
gacctgtgga aattgcttcc tgaaaacaac gttctgtccc cattgcctag tcaagcaatg     120
gatgatttga tgctgtcccc agacgatatt gaacaatggt tcactgaaga tccaggccca     180
gatgaagctc cacgaatgcc agaggccgct ccaccggttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagcccct aacaagatgt tttgccaact cgcgaagacc     420
tgcccagtcc aactgtgggt cgactccacc cctccacctg tacacgtgt ccgcgcaatg      480 gccatctaca agcagagcca gcacatgacg gaggtcgtac gacgctgtcc acaccatgag     540
cgctgctcag attctgatgg tctggcgcca ccacagcatc ttatccgagt ggaaggtaac     600
ctacgcgtgg agtatctaga tgaccgcaac acttttcgac acagtgtggt ggtgccatat     660
gagccaccag aagttggctc tgactgcacc accatccact acaactatat gtgtaacagt     720
tcatgcatgg gcggcatgaa ccggcggccg atcctgacca tcatcactct cgaggattcc     780
tcaggtaatc tccttcgaag gaattccttt gaggtgcgtg tttgtgcatg cccgggccgc     840
gatcgccgga ccgaagagga gaatctccgg aagaaggtg agcctcacca cgagctgcca      900
```

```
ccaggaagca ctaagcgagc actgccaaac aacaccagca gttctccaca gccaaagaag      960
aaacctttgg acggagaata tttcacccct cagatccgtg gccgtgagcg gttcgagatg     1020
ttccgagagc tgaatgaggc cttagaactt aaggatgccc aggctggtaa ggagccagga     1080
ggcagccgtg ctcatagcag ccacctgaag tccaaaaagg gtcagtctac ctcccgccat     1140
aaaaaactga tgttcaagac cgaaggtcct gactcagact ga                        1182

<210> SEQ ID NO 45
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 45
atggaagaac cacagtcaga tcctagcgtc gaaccacctc tgagtcagga aaccttttca       60
gacctgtgga aattgcttcc tgaaaacaac gttctgtccc cattgcctag tcaagcaatg      120
gatgatttga tgctgtcccc agacgatatt gaacaatggt tcactgaaga tccaggccca      180
gatgaagctc cacgaatgcc agaggccgct ccaccggttg ccccagcacc agcagctcct      240
acaccggcgg ccccagctcc ggccccatcc tggcctctgt catcttctgt cccttcccag      300
aaaacctacc aggcagcta cggtttccgt ctgggcttct tgcattctgg aactgccaag      360
tctgttactt gtacgtactc tccagcccct aacaagatgt tttgccaact cgcgaagacc      420
tgcccagtcc aactgtgggt cgactccacc cctccacctg gtacacgtgt ccgcgcaatg      480
gccatctaca gcagagcca gcacatgacg gaggtcatgc gacgctgtcc acaccatgag      540
cgctgctcag attctgatgg tctggcgcca ccacagcatc ttatccgagt ggaaggtaac      600
ctacgcgtgg agtatctaga tgaccgcaac actttttcgac acagtgtggt ggtgccatat      660
gagccaccag aagttggctc tgactgcacc accatccact acaactatat gtgtaacagt      720
tcatgcatgg gcggcatgaa ccggcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaggtg agcctcacca cgagctgcca      900
ccaggaagca ctaagcgagc actgccaaac aacaccagca gttctccaca gccaaagaag      960
aaacctttgg acggagaata tttcacccct cagatccgtg gccgtgagcg gttcgagatg     1020
ttccgagagc tgaatgaggc cttagaactt aaggatgccc aggctggtaa ggagccagga     1080
ggcagccgtg ctcatagcag ccacctgaag tccaaaaagg gtcagtctac ctcccgccat     1140
aaaaaactga tgttcaagac cgaaggtcct gactcagact ga                        1182

<210> SEQ ID NO 46
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 46
atggaagaac cacagtcaga tcctagcgtc gaaccacctc tgagtcagga aaccttttca       60
gacctgtgga aattgcttcc tgaaaacaac gttctgtccc cattgcctag tcaagcaatg      120
gatgatttga tgctgtcccc agacgatatt gaacaatggt tcactgaaga tccaggccca      180
gatgaagctc cacgaatgcc agaggccgct ccaccggttg ccccagcacc agcagctcct      240
```

```
acaccggcgg ccccagctcc ggccccatcc tggcctctgt catcttctgt cccttcccag      300
aaaacctacc agggcagcta cggtttccgt ctgggcttct tgcattctgg aactgccaag      360
tctgttactt gtacgtactc tccagcccct aacaagatgt tttgccaact cgcgaagacc      420
tgcccagtcc aactgtgggt cgactccacc cctccacctg gtacacgtgt ccgcgcaatg      480
gccatctaca agcagagcca gcacatgacg gaggtcgtac gacgctgtcc acaccatgag      540
cgctgctcag attctgatgg tctggcgcca ccacagcatc ttacacgagt ggaaggtaac      600
ctacgcgtgg agtatctaga tgaccgcaac acttttcgac acagtgtggt ggtgccatat      660
gagccaccag aagttggctc tgactgcacc accatcccac taactatat gtgtaacagt       720 tcatgcatgg gcggcatgaa ccggcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaggtg agcctcacca cgagctgcca       900
ccaggaagca ctaagcgagc actgccaaac acaccagca gttctccaca gccaaagaag       960
aaacctttgg acggagaata tttcacccctt cagatccgtg gccgtgagcg gttcgagatg    1020
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                      1182

<210> SEQ ID NO 47
<211> LENGTH: 1181
<212> TYPE: DNA
<213> ORGANISM: Artificial Sequence
<220> FEATURE:
<223> OTHER INFORMATION: Produced by genetic engineering

<400> SEQUENCE: 47
tggaagaacc acagtcagat cctagcgtcg aaccacctct gagtcaggaa accttttcag       60
acctgtggaa attgcttcct gaaaacaacg ttctgtcccc attgcctagt caagcaatgg      120
atgatttgat gctgtcccca gacgatattg acaatggtt cactgaagat ccaggcccag       180
atgaagctcc acgaatgcca gaggccgctc caccggttgc cccagcacca gcagctccta      240
caccggcggc cccagctccg gccccatcct ggcctctgtc atcttctgtc ccttcccaga      300
aaacctacca gggcagctac ggtttccgtc tgggcttctt gcattctgga actgccaagt      360
ctgttacttg tacgtactct ccagccctta acaagatgtt ttaccaactc gcgaagacct      420
gcccagtcca actgtgggtc gactccaccc ctccacctgg tacacgtgtc cgcgcaatgg      480
ccatctacaa gcagagccag cacatgacgg aggtcgtacg acgctgtcca ccatgagc       540 gctgctcaga ttctgatggt ctggcgccac cacagcatct tatccgagtg gaaggtaacc      600
tacgcgtgga gtatctagat gaccgcaaca cttttcgaca cagtgtggtg gtgccatatg      660
agccaccaga agttggctct gactgcacca ccatccacta caactatatg tgtaacagtt      720
catgcatggg cggcatgaac cggcggccga tcctgaccat catcactctc gaggattcct      780
caggtaatct cctaggacgg aattcctttg aggtgcgtgt tgtgcatgc ccgggccgcg       840 atcgccggac cgaagaggag aatctccgga gaaaggtga gcctcaccac gagctgccac      900
caggaagcac taagcgagca ctgccaaaca acaccagcag ttctccacag ccaaagaaga      960
aacctttgga cggagaatat ttcacccttc agatccgtgg ccgtgagcgg ttcgagatgt    1020
tccgagagct gaatgaggcc ttagaactta aggatgccca ggctggtaag gagccaggag    1080
gcagccgtgc tcatagcagc cacctgaagt ccaaaaaggg tcagtctacc tcccgccata    1140
```

```
aaaaactgat gttcaagacc gaaggtcctg actcagactg a                1181

<210> SEQ ID NO 48
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 48
atggaagaac cacagtcaga tcctagcgtc gaaccacctc tgagtcagga aaccttttca    60
gacctgtgga aattgcttcc tgaaaacaac gttctgtccc cattgcctag tcaagcaatg   120
gatgatttga tgctgtcccc agacgatatt gaacaatggt tcactgaaga tccaggccca   180
gatgaagctc cacgaatgcc agaggccgct ccaccggttg ccccagcacc agcagctcct   240
acaccggcgg ccccagctcc ggccccatcc tggcctctgt catcttctgt cccttcccag   300
aaaacctacc agggcagcta cggtttccgt ctgggcttct tgcattctgg aactgccaag   360
tctgttactt gtacgtactc tccagccctt aacaagatgt tttgccaact cgcgaagacc   420
tgcccagtcc aactgtgggt cgactccacc cctccacctg gtacacgtgt ccgcgcaatg   480
gccatctaca gcagagcca gcacatgacg gaggtcgtac gacgctgtcc acaccatgag   540
cgctgctcag attctgatgg tctggcgcca ccacagcatc ttatccgagt ggaaggtaac   600
ctacgcgtgg agtatctaga tgaccgcaac acttttcgac acagtgtggt ggtgccatat   660
gagccaccag aagttggctc tgactgcacc accatccact acaactatat gtgtaactca   720
agcttcatgg gcggcatgaa ccggcggccg atcctgacca tcatcactct cgaggattcc   780
tcaggtaatc tcctaggacg gaattccttt gaggtgcgtg tttgtgcatg cccgggccgc   840
gatcgccgga ccgaagagga gaatctccgg aagaaggtg agcctcacca cgagctgcca   900
ccaggaagca ctaagcgagc actgccaaac aacaccagca gttctccaca gccaaagaag   960
aaacctttgg acggagaata tttcacccct cagatccgtg gccgtgagcg gttcgagatg   1020
ttccgagagc tgaatgaggc cttagaactt aaggatgccc aggctggtaa ggagccagga   1080
ggcagccgtg ctcatagcag ccacctgaag tccaaaaagg gtcagtctac ctcccgccat   1140
aaaaaactga tgttcaagac cgaaggtcct gactcagact ga                    1182

<210> SEQ ID NO 49
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 49
atggaagaac cacagtcaga tcctagcgtc gaaccacctc tgagtcagga aaccttttca    60
gacctgtgga aattgcttcc tgaaaacaac gttctgtccc cattgcctag tcaagcaatg   120
gatgatttga tgctgtcccc agacgatatt gaacaatggt tcactgaaga tccaggccca   180
gatgaagctc cacgaatgcc agaggccgct ccaccggttg ccccagcacc agcagctcct   240
acaccggcgg ccccagctcc ggccccatcc tggcctctgt catcttctgt cccttcccag   300
aaaacctacc agggcagcta cggtttccgt ctgggcttct tgcattctgg aactgccaag   360
tctgttactt gtacgtactc tccagccctt aacaagatgt tttgccaact cgcgaagacc   420
tgcccagtcc aactgtgggt cgactccacc cctccacctg gtacacgtgt ccgcgcaatg   480
```

```
gccatctaca agcagagcca gcacatgacg gaggtcgtac gacgctgtcc acaccatgag      540
cgctgctcag attctgatgg tctggcgcca ccacagcatc ttatccgagt ggaaggtaac      600
ctacgcgtgg agtatctaga tgaccgcaac acttttcgac acagtgtggt ggtgccatat      660
gagccaccag aagttggctc tgactgcacc accatccact acaactatat gtgtaacagt      720
tcatgcatgg gcggcatgaa ccggcggccg atcctgacca tcatcactct cgaggattcc      780
tcaggtaatc tcctaggacg gaattccttt gaggtgcgtg tttacgcgtg cccgggccgc      840
gatcgccgga ccgaagagga gaatctccgg aagaaggtg agcctcacca cgagctgcca       900
ccaggaagca ctaagcgagc actgccaaac aacaccagca gttctccaca gccaaagaag      960
aaacctttgg acggagaata tttcacccctt cagatccgtg gccgtgagcg gttcgagatg     1020
ttccgagagc tgaatgaggc cttagaactt aaggatgccc aggctggtaa ggagccagga     1080
ggcagccgtg ctcatagcag ccacctgaag tccaaaaagg gtcagtctac ctcccgccat     1140
aaaaaactga tgttcaagac cgaaggtcct gactcagact ga                        1182
```

<210> SEQ ID NO 50
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 50

```
atggaagaac cacagtcaga tcctagcgtc gaaccacctc tgagtcagga aaccttttca       60
gacctgtgga aattgcttcc tgaaaacaac gttctgtccc cattgcctag tcaagcaatg      120
gatgatttga tgctgtcccc agacgatatt gaacaatggt tcactgaaga tccaggccca      180
gatgaagctc cacgaatgcc agaggccgct ccaccggttg ccccagcacc agcagctcct      240
acaccggcgg ccccagctcc ggccccatcc tggcctctgt catcttctgt cccttcccag      300
aaaacctacc agggcagcta cggtttccgt ctgggcttct tgcattctgg aactgccaag      360
tctgttactt gtacgtactc tccagcccctt aaccgcatgt tttgccaact cgcgaagacc      420
tgcccagtcc aactgtgggt cgactccacc cctccacctg gtacacgtgt ccgcgcaatg      480
gccatctaca agcagagcca gcacatgacg gaggtcgtac gacgctgtcc acaccatgag      540
cgctgctcag attctgatgg tctggcgcca ccacagcatc ttatccgagt ggaaggtaac      600
ctacgcgtgg agtatctaga tgaccgcaac acttttcgac acagtgtggt ggtgccatat      660
gagccaccag aagttggctc tgactgcacc accatccact acaactatat gtgtaacagt      720
tcatgcatgg gcggcatgaa ccggcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaggtg agcctcacca cgagctgcca       900
ccaggaagca ctaagcgagc actgccaaac aacaccagca gttctccaca gccaaagaag      960
aaacctttgg acggagaata tttcacccctt cagatccgtg gccgtgagcg gttcgagatg     1020
ttccgagagc tgaatgaggc cttagaactt aaggatgccc aggctggtaa ggagccagga     1080
ggcagccgtg ctcatagcag ccacctgaag tccaaaaagg gtcagtctac ctcccgccat     1140
aaaaaactga tgttcaagac cgaaggtcct gactcagact ga                        1182
```

<210> SEQ ID NO 51
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 51

| | | | | | |
|---|---|---|---|---|---|
| atggaagaac | cacagtcaga | tcctagcgtc | gaaccacctc | tgagtcagga | aaccttttca | 60 |
| gacctgtgga | aattgcttcc | tgaaaacaac | gttctgtccc | cattgcctag | tcaagcaatg | 120 |
| gatgatttga | tgctgtcccc | agacgatatt | gaacaatggt | tcactgaaga | tccaggccca | 180 |
| gatgaagctc | cacgaatgcc | agaggccgct | ccaccggttg | ccccagcacc | agcagctcct | 240 |
| acaccggcgg | ccccagctcc | ggccccatcc | tggcctctgt | catcttctgt | cccttcccag | 300 |
| aaaacctacc | agggcagcta | cggtttccgt | ctgggcttct | tgcattctgg | aactgccaag | 360 |
| tctgttactt | gtacgtactc | tccagccctt | aacaagatgt | tttgccaact | cgcgaagacc | 420 |
| tgcccagtcc | aactgtgggt | cgactccacc | cctccaccgg | taacacgtgt | ccgcgcaatg | 480 |
| gccatctaca | gcagagcca | gcacatgacg | gaggtcgtac | gacgctgtcc | acaccatgag | 540 |
| cgctgctcag | attctgatgg | tctggcgcca | ccacagcatc | ttatccgagt | ggaaggtaac | 600 |
| ctacgcgtgg | agtatctaga | tgaccgcaac | acttttcgac | acagtgtggt | ggtgccatat | 660 |
| gagccaccag | aagttggctc | tgactgcacc | accatccact | acaactatat | gtgtaacagt | 720 |
| tcatgcatgg | gcggcatgaa | ccggcggccg | atcctgacca | tcatcactct | cgaggattcc | 780 |
| tcaggtaatc | tcctaggacg | gaattccttt | gaggtgcgtg | tttgtgcatg | cccgggccgc | 840 |
| gatcgccgga | ccgaagagga | gaatctccgg | aagaaggtg | agcctcacca | cgagctgcca | 900 |
| ccaggaagca | ctaagcgagc | actgccaaac | aacaccagca | gttctccaca | gccaaagaag | 960 |
| aaacctttgg | acggagaata | tttcaccctt | cagatccgtg | gccgtgagcg | gttcgagatg | 1020 |
| ttccgagagc | tgaatgaggc | cttagaactt | aaggatgccc | aggctggtaa | ggagccagga | 1080 |
| ggcagccgtg | ctcatagcag | ccacctgaag | tccaaaaagg | gtcagtctac | ctcccgccat | 1140 |
| aaaaaactga | tgttcaagac | cgaaggtcct | gactcagact | ga | | 1182 |

<210> SEQ ID NO 52
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 52

| | | | | | |
|---|---|---|---|---|---|
| atggaagaac | cacagtcaga | tcctagcgtc | gaaccacctc | tgagtcagga | aaccttttca | 60 |
| gacctgtgga | aattgcttcc | tgaaaacaac | gttctgtccc | cattgcctag | tcaagcaatg | 120 |
| gatgatttga | tgctgtcccc | agacgatatt | gaacaatggt | tcactgaaga | tccaggccca | 180 |
| gatgaagctc | cacgaatgcc | agaggccgct | ccaccggttg | ccccagcacc | agcagctcct | 240 |
| acaccggcgg | ccccagctcc | ggccccatcc | tggcctctgt | catcttctgt | cccttcccag | 300 |
| aaaacctacc | agggcagcta | cggtttccgt | ctgggcttct | tgcattctgg | aactgccaag | 360 |
| tctgttactt | gtacgtactc | tccagccctt | aacaagatgt | tttgccaact | cgcgaagacc | 420 |
| tgcccagtcc | aactgtgggt | cgactccacc | cctccacctg | gtacacgtgt | ccgcgcaatg | 480 |
| acaatctaca | gcagagcca | gcacatgacg | gaggtcgtac | gacgctgtcc | acaccatgag | 540 |
| cgctgctcag | attctgatgg | tctggcgcca | ccacagcatc | ttatccgagt | ggaaggtaac | 600 |
| ctacgcgtgg | agtatctaga | tgaccgcaac | acttttcgac | acagtgtggt | ggtgccatat | 660 |
| gagccaccag | aagttggctc | tgactgcacc | accatccact | acaactatat | gtgtaacagt | 720 |

```
tcatgcatgg gcggcatgaa ccggcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaaggtg agcctcacca cgagctgcca      900
ccaggaagca ctaagcgagc actgccaaac aacaccagca gttctccaca gccaaagaag      960
aaacctttgg acggagaata tttcacccct cagatccgtg gccgtgagcg gttcgagatg     1020
ttccgagagc tgaatgaggc cttagaactt aaggatgccc aggctggtaa ggagccagga     1080
ggcagccgtg ctcatagcag ccacctgaag tccaaaaagg gtcagtctac ctcccgccat     1140
aaaaaactga tgttcaagac cgaaggtcct gactcagact ga                        1182
```

<210> SEQ ID NO 53
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 53

```
atggaagaac cacagtcaga tcctagcgtc gaaccacctc tgagtcagga aaccttttca       60
gacctgtgga aattgcttcc tgaaaacaac gttctgtccc cattgcctag tcaagcaatg      120
gatgatttga tgctgtcccc agacgatatt gaacaatggt tcactgaaga tccaggccca      180
gatgaagctc cacgaatgcc agaggccgct ccaccggttg ccccagcacc agcagctcct      240
acaccggcgg ccccagctcc ggccccatcc tggcctctgt catcttctgt cccttcccag      300
aaaacctacc agggcagcta cggtttccgt ctgggcttct tgcattctgg aactgccaag      360
tctgttactt gtacgtactc tccagcccct aacaagatgt tttgccaact cgcgaagacc      420
tgcccagtcc aactgtgggt cgactccacc cctccacctg gtacacgtgt ccgcgcaatg      480
gccatctaca gcagagcca gcacatgacg gaggtcgtac gacgctgtcc acaccatgag      540
cgctgctcag attctgatgg tctggcgcca ccacagcatc ttatccgagt ggaaggtaac      600
ctacgcgtgg agtatctaga tgaccgcaac acttttcgac acagtgtggt ggtgccatat      660
gagccaccag aagttggctc tgactgcacc accatccact acaactatat gtgtaacagt      720
tcatgcatgg gcggcatgaa ccggcggccg atcctgacca tcatcactct cgaggattcc      780
tcaggtaatc tcctaggacg gaattccttt gaggtgcgtg tttgtgcatg cccgggccgc      840
gagcgccgga ccgaagagga gaatctccgg aagaaaggtg agcctcacca cgagctgcca      900
ccaggaagca ctaagcgagc actgccaaac aacaccagca gttctccaca gccaaagaag      960
aaacctttgg acggagaata tttcacccct cagatccgtg gccgtgagcg gttcgagatg     1020
ttccgagagc tgaatgaggc cttagaactt aaggatgccc aggctggtaa ggagccagga     1080
ggcagccgtg ctcatagcag ccacctgaag tccaaaaagg gtcagtctac ctcccgccat     1140
aaaaaactga tgttcaagac cgaaggtcct gactcagact ga                        1182
```

<210> SEQ ID NO 54
<211> LENGTH: 393
<212> TYPE: PRT
<213> ORGANISM: Homo sapiens

<400> SEQUENCE: 54

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30
```

```
Ser Pro Leu Pro Ser Gln Ala Met Asp Asp Leu Met Leu Ser Pro Asp
         35                  40                  45
Asp Ile Glu Gln Trp Phe Thr Glu Asp Pro Gly Pro Asp Glu Ala Pro
 50                  55                  60
Arg Met Pro Glu Ala Ala Pro Pro Val Ala Pro Ala Pro Ala Ala Pro
 65                  70                  75                  80
Thr Pro Ala Ala Pro Ala Pro Ala Pro Ser Trp Pro Leu Ser Ser Ser
                 85                  90                  95
Val Pro Ser Gln Lys Thr Tyr Gln Gly Ser Tyr Gly Phe Arg Leu Gly
                100                 105                 110
Phe Leu His Ser Gly Thr Ala Lys Ser Val Thr Cys Thr Tyr Ser Pro
                115                 120                 125
Ala Leu Asn Lys Met Phe Cys Gln Leu Ala Lys Thr Cys Pro Val Gln
        130                 135                 140
Leu Trp Val Asp Ser Thr Pro Pro Pro Gly Thr Arg Val Arg Ala Met
145                 150                 155                 160
Ala Ile Tyr Lys Gln Ser Gln His Met Thr Glu Val Val Arg Arg Cys
                165                 170                 175
Pro His His Glu Arg Cys Ser Asp Ser Asp Gly Leu Ala Pro Pro Gln
                180                 185                 190
His Leu Ile Arg Val Glu Gly Asn Leu Arg Val Glu Tyr Leu Asp Asp
                195                 200                 205
Arg Asn Thr Phe Arg His Ser Val Val Val Pro Tyr Glu Pro Pro Glu
        210                 215                 220
Val Gly Ser Asp Cys Thr Thr Ile His Tyr Asn Tyr Met Cys Asn Ser
225                 230                 235                 240
Ser Cys Met Gly Gly Met Asn Arg Arg Pro Ile Leu Thr Ile Ile Thr
                245                 250                 255
Leu Glu Asp Ser Ser Gly Asn Leu Leu Gly Arg Asn Ser Phe Glu Val
                260                 265                 270
Arg Val Cys Ala Cys Pro Gly Arg Asp Arg Arg Thr Glu Glu Glu Asn
        275                 280                 285
Leu Arg Lys Lys Gly Glu Pro His His Glu Leu Pro Pro Gly Ser Thr
        290                 295                 300
Lys Arg Ala Leu Pro Asn Asn Thr Ser Ser Pro Gln Pro Lys Lys Lys
305                 310                 315                 320
Lys Pro Leu Asp Gly Glu Tyr Phe Thr Leu Gln Ile Arg Gly Arg Glu
                325                 330                 335
Arg Phe Glu Met Phe Arg Glu Leu Asn Glu Ala Leu Glu Leu Lys Asp
                340                 345                 350
Ala Gln Ala Gly Lys Glu Pro Gly Gly Ser Arg Ala His Ser Ser His
        355                 360                 365
Leu Lys Ser Lys Lys Gly Gln Ser Thr Ser Arg His Lys Lys Leu Met
        370                 375                 380
Phe Lys Thr Glu Gly Pro Asp Ser Asp
385                 390

<210> SEQ ID NO 55
<211> LENGTH: 393
<212> TYPE: PRT
<213> ORGANISM: Homo sapiens

<400> SEQUENCE: 55

Met Glu Glu Pro Gln Ser Asp Pro Ser Val Glu Pro Pro Leu Ser Gln
```

```
                1               5                   10                  15
        Glu Thr Phe Ser Asp Leu Trp Lys Leu Leu Pro Glu Asn Asn Val Leu
                        20                  25                  30

Ser Pro Leu Pro Ser Gln Ala Met Asp Asp Leu Met Leu Ser Pro Asp
                        35                  40                  45

Asp Ile Glu Gln Trp Phe Thr Glu Asp Pro Gly Pro Asp Glu Ala Pro
                        50                  55                  60

Arg Met Pro Glu Ala Ala Pro Arg Val Ala Pro Ala Pro Ala Ala Pro
        65                      70                  75                  80

Thr Pro Ala Ala Pro Ala Pro Ser Trp Pro Leu Ser Ser Ser
                                85                  90                  95

Val Pro Ser Gln Lys Thr Tyr Gln Gly Ser Tyr Gly Phe Arg Leu Gly
                        100                 105                 110

Phe Leu His Ser Gly Thr Ala Lys Ser Val Thr Cys Thr Tyr Ser Pro
                        115                 120                 125

Ala Leu Asn Lys Met Phe Cys Gln Leu Ala Lys Thr Cys Pro Val Gln
                        130                 135                 140

Leu Trp Val Asp Ser Thr Pro Pro Gly Thr Arg Val Arg Ala Met
        145                     150                 155                 160

Ala Ile Tyr Lys Gln Ser Gln His Met Thr Glu Val Val Arg Cys
                        165                 170                 175

Pro His His Glu Arg Cys Ser Asp Ser Asp Gly Leu Ala Pro Pro Gln
                        180                 185                 190

His Leu Ile Arg Val Glu Gly Asn Leu Arg Val Glu Tyr Leu Asp Asp
                        195                 200                 205

Arg Asn Thr Phe Arg His Ser Val Val Val Pro Tyr Glu Pro Pro Glu
                        210                 215                 220

Val Gly Ser Asp Cys Thr Thr Ile His Tyr Asn Tyr Met Cys Asn Ser
        225                     230                 235                 240

Ser Cys Met Gly Gly Met Asn Arg Arg Pro Ile Leu Thr Ile Ile Thr
                        245                 250                 255

Leu Glu Asp Ser Ser Gly Asn Leu Leu Gly Arg Asn Ser Phe Glu Val
                        260                 265                 270

Arg Val Cys Ala Cys Pro Gly Arg Asp Arg Arg Thr Glu Glu Glu Asn
                        275                 280                 285

Leu Arg Lys Lys Gly Glu Pro His Glu Leu Pro Pro Gly Ser Thr
                        290                 295                 300

Lys Arg Ala Leu Pro Asn Asn Thr Ser Ser Pro Gln Pro Lys Lys
        305                     310                 315                 320

Lys Pro Leu Asp Gly Glu Tyr Phe Thr Leu Gln Ile Arg Gly Arg Glu
                        325                 330                 335

Arg Phe Glu Met Phe Arg Glu Leu Asn Glu Ala Leu Glu Leu Lys Asp
                        340                 345                 350

Ala Gln Ala Gly Lys Glu Pro Gly Gly Ser Arg Ala His Ser Ser His
                        355                 360                 365

Leu Lys Ser Lys Lys Gly Gln Ser Thr Ser Arg His Lys Lys Leu Met
                        370                 375                 380

Phe Lys Thr Glu Gly Pro Asp Ser Asp
        385                     390

<210> SEQ ID NO 56
<211> LENGTH: 393
<212> TYPE: PRT
<213> ORGANISM: Homo sapiens
```

<400> SEQUENCE: 56

```
Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Ser Asp
         35                  40                  45

Asp Ile Glu Gln Trp Phe Thr Glu Asp Pro Gly Pro Asp Glu Ala Pro
 50                  55                  60

Arg Met Pro Glu Ala Ala Pro Arg Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390
```

<210> SEQ ID NO 57
<211> LENGTH: 393
<212> TYPE: PRT
<213> ORGANISM: Homo sapiens

<400> SEQUENCE: 57

```
Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Ser Asp
         35                  40                  45

Asp Ile Glu Gln Trp Phe Thr Glu Asp Pro Gly Pro Asp Glu Ala Pro
 50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380
```

Phe Lys Thr Glu Gly Pro Asp Ser Asp
385                390

<210> SEQ ID NO 58
<211> LENGTH: 2629
<212> TYPE: DNA
<213> ORGANISM: Homo sapiens

<400> SEQUENCE: 58

| | | | | | |
|---|---|---|---|---|---|
| acttgtcatg | gcgactgtcc | agctttgtgc | caggagcctc | gcaggggttg | atgggattgg | 60 |
| ggtttttcccc | tcccatgtgc | tcaagactgg | cgctaaaagt | tttgagcttc | tcaaaagtct | 120 |
| agagccaccg | tccagggagc | aggtagctgc | tgggctccgg | ggacactttg | cgttcgggct | 180 |
| gggagcgtgc | tttccacgac | ggtgacacgc | ttccctggat | tggcagccag | actgccttcc | 240 |
| ggtcactgc | catggaggag | ccgcagtcag | atcctagcgt | cgagcccct | ctgagtcagg | 300 |
| aaacattttc | agacctatgg | aaactacttc | ctgaaaacaa | cgttctgtcc | cccttgccgt | 360 |
| cccaagcaat | ggatgatttg | atgctgtccc | cggacgatat | tgaacaatgg | ttcactgaag | 420 |
| acccaggtcc | agatgaagct | cccagaatgc | cagaggctgc | tccccgcgtg | cccctgcac | 480 |
| cagcagctcc | tacaccggcg | gcccctgcac | cagccccctc | ctggcccctg | tcatcttctg | 540 |
| tcccttccca | gaaaacctac | cagggcagct | acggtttccg | tctgggcttc | ttgcattctg | 600 |
| ggacagccaa | gtctgtgact | tgcacgtact | cccctgccct | caacaagatg | ttttgccaac | 660 |
| tggccaagac | ctgccctgtg | cagctgtggg | ttgattccac | accccgccc | ggcacccgcg | 720 |
| tccgcgccat | ggccatctac | aagcagtcac | agcacatgac | ggaggttgtg | aggcgctgcc | 780 |
| cccaccatga | gcgctgctca | gatagcgatg | gtctggcccc | tcctcagcat | cttatccgag | 840 |
| tggaaggaaa | tttgcgtgtg | gagtatttgg | atgcagaaa | cacttttcga | catagtgtgg | 900 |
| tggtgcccta | tgagccgcct | gaggttggct | ctgactgtac | caccatccac | tacaactaca | 960 |
| tgtgtaacag | ttcctgcatg | ggcggcatga | accggaggcc | catcctcacc | atcatcacac | 1020 |
| tggaagactc | cagtggtaat | ctactgggac | ggaacagctt | tgaggtgcgt | gtttgtgcct | 1080 |
| gtcctgggag | agaccggcgc | acagaggaag | agaatctccg | caagaaaggg | gagcctcacc | 1140 |
| acgagctgcc | cccagggagc | actaagcgag | cactgcccaa | caacaccagc | tcctctcccc | 1200 |
| agccaaagaa | gaaaccactg | gatggagaat | atttcaccct | tcagatccgt | gggcgtgagc | 1260 |
| gcttcgagat | gttccgagag | ctgaatgagg | ccttggaact | caaggatgcc | caggctggga | 1320 |
| aggagccagg | ggggagcagg | gctcactcca | gccacctgaa | gtccaaaaag | ggtcagtcta | 1380 |
| cctcccgcca | taaaaaactc | atgttcaaga | cagaagggcc | tgactcagac | tgacattctc | 1440 |
| cacttcttgt | tccccactga | cagcctccca | cccccatctc | tccctcccct | gccattttgg | 1500 |
| gttttgggtc | tttgaaccct | tgcttgcaat | aggtgtgcgt | cagaagcacc | caggacttcc | 1560 |
| atttgctttg | tcccggggct | ccactgaaca | agttggcctg | cactggtgtt | ttgttgtggg | 1620 |
| gaggaggatg | gggagtagga | cataccagct | tagattttaa | ggttttact | gtgagggatg | 1680 |
| tttgggagat | gtaagaaatg | ttcttgcagt | taagggttag | tttacaatca | gccacattct | 1740 |
| aggtaggtag | gggcccactt | caccgtacta | accagggaag | ctgtccctca | tgttgaattt | 1800 |
| tctctaactt | caaggcccat | atctgtgaaa | tgctggcatt | tgcacctacc | tcacagagtg | 1860 |
| cattgtgagg | gttaatgaaa | taatgtacat | ctggccttga | aaccaccttt | tattacatgg | 1920 |
| ggtctaaaac | ttgacccct | tgagggtgcc | tgttccctct | ccctctccct | gttggctggt | 1980 |
| gggttggtag | tttctacagt | tgggcagctg | gttaggtaga | gggagttgtc | aagtcttgct | 2040 |

-continued

```
ggcccagcca aaccctgtct gacaacctct tggtcgacct tagtacctaa aaggaaatct      2100
caccccatcc cacaccctgg aggatttcat ctcttgtata tgatgatctg gatccaccaa      2160
gacttgtttt atgctcaggg tcaatttctt ttttcttttt tttttttttt tttcttttc       2220 tttgagactg ggtctcgctt tgttgcccag gctggagtgg agtggcgtga tcttggctta     2280
ctgcagcctt tgcctcccg gctcgagcag tcctgcctca gcctccggag tagctgggac      2340
cacaggttca tgccaccatg gccagccaac ttttgcatgt tttgtagaga tggggtctca     2400
cagtgttgcc caggctggtc tcaaactcct gggctcaggc gatccacctg tctcagcctc     2460
ccagagtgct gggattacaa ttgtgagcca ccacgtggag ctggaagggt caacatcttt     2520
tacattctgc aagcacatct gcattttcac cccacccttc ccctccttct cccttttat      2580 atcccatttt tatatcgatc tcttatttta caataaaact ttgctgcca                 2629

<210> SEQ ID NO 59
<211> LENGTH: 2629
<212> TYPE: DNA
<213> ORGANISM: Homo sapiens

<400> SEQUENCE: 59
acttgtcatg gcgactgtcc agctttgtgc caggagcctc gcaggggttg atgggattgg       60
ggttttcccc tcccatgtgc tcaagactgg cgctaaaagt tttgagcttc tcaaaagtct      120
agagccaccg tccagggagc aggtagctgc tgggctccgg ggacactttg cgttcgggct      180
gggagcgtgc tttccacgac ggtgacacgc ttccctggat tggcagccag actgccttcc     240
gggtcactgc catggaggag ccgcagtcag atcctagcgt cgagccccct ctgagtcagg     300
aaacattttc agacctatgg aaactacttc ctgaaaacaa cgttctgtcc cccttgccgt     360
cccaagcaat ggatgatttg atgctgtccc cggacgatat tgaacaatgg ttcactgaag     420
acccaggtcc agatgaagct cccagaatgc cagaggctgc tccccccgtg gcccctgcac     480
cagcagctcc tacaccggcg gcccctgcac cagcccccctc ctggcccctg tcatcttctg    540
tcccttccca gaaaacctac cagggcagct acggtttccg tctgggcttc ttgcattctg    600
ggacagccaa gtctgtgact tgcacgtact cccctgccct caacaagatg ttttgccaac    660
tggccaagac ctgccctgtg cagctgtggg ttgattccac accccgccc ggcacccgcg    720 tccgcgccat ggccatctac aagcagtcac agcacatgac ggaggttgtg aggcgctgcc    780
cccaccatga gcgctgctca gatagcgatg gtctggcccc tcctcagcat cttatccgag    840
tggaaggaaa tttgcgtgtg gagtatttgg atgacagaaa cacttttcga catagtgtgg    900
tggtgcccta tgagccgcct gaggttggct ctgactgtac caccatccac tacaactaca     960
tgtgtaacag ttcctgcatg ggcggcatga accggaggcc catcctcacc atcatcacac    1020
tggaagactc cagtggtaat ctactgggac ggaacagctt tgaggtgcgt gtttgtgcct    1080
gtcctgggag agaccggcgc acagaggaag agaatctccg caagaaaggg gagcctcacc    1140
acgagctgcc cccagggagc actaagcgag cactgcccaa caacaccagc tcctctcccc    1200
agccaaagaa gaaaccactg gatggagaat atttcaccct tcagatccgt gggcgtgagc    1260
gcttcgagat gttccgagag ctgaatgagg ccttggaact caaggatgcc caggctggga    1320
aggagccagg ggggagcagg gctcactcca gccacctgaa gtccaaaaag ggtcagtcta    1380
cctcccgcca taaaaaactc atgttcaaga cagaagggcc tgactcagac tgacattctc     1440
cacttcttgt tccccactga cagcctccca ccccatctc tccctcccct gccattttgg    1500
gttttgggtc tttgaaccct tgcttgcaat aggtgtgcgt cagaagcacc caggacttcc    1560
```

```
atttgctttg tcccggggct ccactgaaca agttggcctg cactggtgtt ttgttgtggg    1620
gaggaggatg gggagtagga cataccagct tagattttaa ggtttttact gtgagggatg    1680
tttgggagat gtaagaaatg ttcttgcagt taagggttag tttacaatca gccacattct    1740
aggtaggtag gggcccactt caccgtacta accagggaag ctgtccctca tgttgaattt    1800
tctctaactt caaggcccat atctgtgaaa tgctggcatt tgcacctacc tcacagagtg    1860
cattgtgagg gttaatgaaa taatgtacat ctggccttga aaccaccttt tattacatgg    1920
ggtctaaaac ttgaccccct tgagggtgcc tgttccctct ccctctccct gttggctggt    1980
gggttggtag tttctacagt tgggcagctg gttaggtaga gggagttgtc aagtcttgct    2040
ggcccagcca aaccctgtct gacaacctct tggtcgacct tagtacctaa aaggaaatct    2100
caccccatcc cacaccctgg aggatttcat ctcttgtata tgatgatctg gatccaccaa    2160
gacttgtttt atgctcaggg tcaatttctt ttttctttt tttttttttt tttcttttc    2220 tttgagactg gtctcgctt tgttgcccag gctggagtgg agtggcgtga tcttggctta    2280
ctgcagcctt tgcctcccg gctcgagcag tcctgcctca gcctccggag tagctgggac    2340
cacaggttca tgccaccatg gccagccaac ttttgcatgt tttgtagaga tggggtctca    2400
cagtgttgcc caggctggtc tcaaaactcct gggctcaggc gatccacctg tctcagcctc    2460
ccagagtgct gggattacaa ttgtgagcca ccacgtggag ctggaagggt caacatcttt    2520
tacattctgc aagcacatct gcattttcac cccacccttc ccctccttct ccctttttat    2580
atcccatttt tatatcgatc tcttatttta caataaaact ttgctgcca                2629

<210> SEQ ID NO 60
<211> LENGTH: 2629
<212> TYPE: DNA
<213> ORGANISM: Homo sapiens

<400> SEQUENCE: 60
acttgtcatg gcgactgtcc agctttgtgc caggagcctc gcaggggttg atgggattgg     60
ggttttcccc tccatgtgc tcaagactgg cgctaaaagt tttgagcttc tcaaaagtct    120
agagccaccg tccagggagc aggtagctgc tgggctccgg ggacactttg cgttcgggct    180
gggagcgtgc tttccacgac ggtgacacgc ttccctggat tggcagccag actgccttcc    240
gggtcactgc catggaggag ccgcagtcag atcctagcgt cgagccccct ctgagtcagg    300
aaacattttc agacctatgg aaactacttc ctgaaaacaa cgttctgtcc cccttgccgt    360
cccaagcaat ggatgatttg atgctgtcct cggacgatat tgaacaatgg ttcactgaag    420
acccaggtcc agatgaagct cccagaatgc cagaggctgc tccccgcgtg gcccctgcac    480
cagcagctcc tacaccggcg gcccctgcac cagccccctc ctggcccctg tcatcttctg    540
tcccttccca gaaaacctac cagggcagct acgtttccg tctgggcttc ttgcattctg    600
ggacagccaa gtctgtgact tgcacgtact cccctgccct caacaagatg ttttgccaac    660
tggccaagac ctgccctgtg cagctgtggg ttgattccac accccgccc ggcacccgcg    720 tccgcgccat ggccatctac aagcagtcac agcacatgac ggaggttgtg aggcgctgcc    780 ccaccatga gcgctgctca gatagcgatg gtctggcccc tcctcagcat cttatccgag    840
tggaaggaaa tttgcgtgtg gagtatttgg atgacagaaa cactttttcga catagtgtgg    900 tggtgcccta tgagccgcct gaggttggct ctgactgtac caccatccac tacaactaca    960
tgtgtaacag ttcctgcatg ggcggcatga accggaggcc catcctcacc atcatcacac   1020
```

```
tggaagactc cagtggtaat ctactgggac ggaacagctt tgaggtgcgt gtttgtgcct    1080
gtcctgggag agaccggcgc acagaggaag agaatctccg caagaaaggg gagcctcacc    1140
acgagctgcc cccagggagc actaagcgag cactgcccaa caacaccagc tcctctcccc    1200
agccaaagaa gaaaccactg gatggagaat atttcaccct tcagatccgt gggcgtgagc    1260
gcttcgagat gttccgagag ctgaatgagg ccttggaact caaggatgcc caggctggga    1320
aggagccagg ggggagcagg gctcactcca gccacctgaa gtccaaaaag ggtcagtcta    1380
cctcccgcca taaaaaactc atgttcaaga cagaagggcc tgactcagac tgacattctc    1440
cacttcttgt tccccactga cagcctccca ccccatctc tccctcccct gccattttgg    1500
gttttgggtc tttgaaccct tgcttgcaat aggtgtgcgt cagaagcacc caggacttcc    1560
atttgctttg tcccggggct ccactgaaca agttggcctg cactggtgtt ttgttgtggg    1620
gaggaggatg gggagtagga cataccagct tagatttaa ggttttact gtgagggatg    1680 tttgggagat gtaagaaatg ttcttgcagt taagggttag tttacaatca gccacattct    1740
aggtaggtag gggcccactt caccgtacta accagggaag ctgtccctca tgttgaattt    1800
tctctaactt caaggcccat atctgtgaaa tgctggcatt tgcacctacc tcacagagtg    1860
cattgtgagg gttaatgaaa taatgtacat ctggccttga aaccacctt tattacatgg    1920 ggtctaaaac ttgacccct tgagggtgcc tgttccctct ccctctccct gttggctggt    1980
gggttggtag tttctacagt tgggcagctg gttaggtaga gggagttgtc aagtcttgct    2040
ggcccagcca aaccctgtct gacaacctct tggtcgacct tagtacctaa aaggaaatct    2100 cacccatcc cacaccctgg aggatttcat ctcttgtata tgatgatctg gatccaccaa    2160
gacttgtttt atgctcaggg tcaatttctt ttttctttt ttttttttt tttcttttc     2220 tttgagactg ggtctcgctt tgttgcccag gctggagtgg agtggcgtga tcttggctta    2280
ctgcagcctt tgcctcccg gctcgagcag tcctgcctca gcctccggag tagctgggac    2340
cacaggttca tgccaccatg gccagccaac ttttgcatgt tttgtagaga tggggtctca    2400
cagtgttgcc caggctggtc tcaaactcct gggctcaggc gatccacctg tctcagcctc    2460
ccagagtgct gggattacaa ttgtgagcca ccacgtggag ctggaagggt caacatcttt    2520
tacattctgc aagcacatct gcattttcac cccacccttc cctccttct ccctttttat    2580 atcccatttt tatatcgatc tcttatttta caataaaact ttgctgcca              2629
```

<210> SEQ ID NO 61
<211> LENGTH: 2629
<212> TYPE: DNA
<213> ORGANISM: Homo sapiens

<400> SEQUENCE: 61

```
acttgtcatg gcgactgtcc agctttgtgc caggagcctc gcaggggttg atgggattgg      60
ggttttcccc tccatgtgc tcaagactgg cgctaaaagt tttgagcttc tcaaaagtct     120
agagccaccg tccagggagc aggtagctgc tgggctccgg ggacactttg cgttcgggct     180
gggagcgtgc tttccacgac ggtgacacgc ttccctggat tggcagccag actgccttcc     240
gggtcactgc catggaggag ccgcagtcag atcctagcgt cgagccccct ctgagtcagg     300
aaacattttc agacctatgg aaactacttc ctgaaaacaa cgttctgtcc ccttgccgt     360 cccaagcaat ggatgatttg atgctgtcct cggacgatat tgaacaatgg ttcactgaag     420
acccaggtcc agatgaagct cccagaatgc cagaggctgc tccccccgtg gcccctgcac     480
cagcagctcc tacaccggcg gcccctgcac cagccccctc ctggcccctg tcatcttctg     540
```

-continued

```
tcccttccca gaaaacctac cagggcagct acggtttccg tctgggcttc ttgcattctg      600
ggacagccaa gtctgtgact tgcacgtact ccoctgccct caacaagatg ttttgccaac      660
tggccaagac ctgccctgtg cagctgtggg ttgattccac accccgccc ggcacccgcg       720
tccgcgccat ggccatctac aagcagtcac agcacatgac ggaggttgtg aggcgctgcc      780
cccaccatga gcgctgctca gatagcgatg gtctggcccc tcctcagcat cttatccgag      840
tggaaggaaa tttgcgtgtg gagtatttgg atgacagaaa cacttttcga catagtgtgg      900
tggtgcccta tgagccgcct gaggttggct ctgactgtac caccatccac tacaactaca      960
tgtgtaacag ttcctgcatg ggcggcatga accggaggcc catcctcacc atcatcacac     1020
tggaagactc cagtggtaat ctactgggac ggaacagctt tgaggtgcgt gtttgtgcct     1080
gtcctgggag agaccggcgc acagaggaag agaatctccg caagaaaggg gagcctcacc     1140
acgagctgcc cccagggagc actaagcgag cactgcccaa caacaccagc tcctctcccc     1200
agccaaagaa gaaaccactg gatggagaat atttcaccct tcagatccgt gggcgtgagc     1260
gcttcgagat gttccgagag ctgaatgagg ccttggaact caaggatgcc caggctggga     1320
aggagccagg ggggagcagg gctcactcca gccacctgaa gtccaaaaag ggtcagtcta     1380
cctcccgcca taaaaaactc atgttcaaga cagaagggcc tgactcagac tgacattctc     1440
cacttcttgt tccccactga cagcctccca ccccatctc tccctcccct gccattttgg      1500
gttttgggtc tttgaaccct tgcttgcaat aggtgtgcgt cagaagcacc caggacttcc     1560
atttgctttg tcccggggct ccactgaaca agttggcctg cactggtgtt ttgttgtggg     1620
gaggaggatg gggagtagga cataccagct tagattttaa ggtttttact gtgagggatg     1680
tttgggagat gtaagaaatg ttcttgcagt taagggttag tttacaatca gccacattct     1740
aggtaggtag gggcccactt caccgtacta accagggaag ctgtccctca tgttgaattt     1800
tctctaactt caaggcccat atctgtgaaa tgctggcatt tgcacctacc tcacagagtg     1860
cattgtgagg gttaatgaaa taatgtacat ctggccttga aaccacccttt tattacatgg    1920
ggtctaaaac ttgaccccct tgagggtgcc tgttccctct ccctctccct gttggctggt     1980
gggttggtag tttctacagt tgggcagctg gttaggtaga gggagttgtc aagtcttgct     2040
ggcccagcca aaccctgtct gacaacctct tggtcgacct tagtacctaa aaggaaatct     2100
caccccatcc cacaccctgg aggatttcat ctcttgtata tgatgatctg gatccaccaa     2160
gacttgtttt atgctcaggg tcaatttctt ttttctttttt tttttttttt tttcttttc    2220
tttgagactg gtctcgctt tgttgcccag gctggagtgg agtggcgtga tcttggctta      2280
ctgcagcctt tgcctccccg gctcgagcag tcctgcctca gcctccggag tagctgggac    2340
cacaggttca tgccaccatg gccagccaac ttttgcatgt tttgtagaga tggggtctca    2400
cagtgttgcc caggctggtc tcaaactcct gggctcaggc gatccacctg tctcagcctc    2460
ccagagtgct gggattacaa ttgtgagcca ccacgtggag ctggaagggt caacatcttt    2520
tacattctgc aagcacatct gcattttcac cccacccttc ccctccttct ccctttttat    2580
atcccatttt tatatcgatc tcttatttta caataaaact ttgctgcca              2629
```

<210> SEQ ID NO 62
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 62

```
atggaagaac cacagtcaga tcctagcgtc gaaccacctc tgagtcagga aaccttttca      60
gacctgtgga aattgcttcc tgaaaacaac gttctgtccc cattgcctag tcaagcaatg     120
gatgatttga tgctgtcccc agacgatatt gaacaatggt tcactgaaga tccaggccca     180
gatgaagctc cacgaatgcc agaggccgct ccacgcgttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagccctt aacaagatgt tttgccaact cgcgaagacc     420
tgcccagtcc aactgtgggt cgactccacc cctccacctg gtacacgtgt ccgcgcaatg     480
gccatctaca agcagagcca gcacatgacg gaggtcgtac gacgctgtcc acaccatgag     540
cgctgctcag attctgatgg tctggcgcca ccacagcatc ttatccgagt ggaaggtaac     600
ctacgcgtgg agtatctaga tgaccgcaac acttttcgac acagtgtggt ggtgccatat     660
gagccaccag aagttggctc tgactgcacc accatccact acaactatat gtgtaacagt     720
tcatgcatgg gcggcatgaa ccggcggccg atcctgacca tcatcactct cgaggattcc     780
tcaggtaatc tcctaggacg gaattccttt gaggtgcgtg tttgtgcatg cccgggccgc     840
gatcgccgga ccgaagagga gaatctccgg aagaaaggtg agcctcacca cgagctgcca     900
ccaggaagca ctaagcgagc actgccaaac aacaccagca gttctccaca gccaaagaag     960
aaaccttgg acgagaata tttcacccctt cagatccgtg gccgtgagcg gttcgagatg    1020
ttccgagagc tgaatgaggc cttagaactt aaggatgccc aggctggtaa ggagccagga    1080
ggcagccgtg ctcatagcag ccacctgaag tccaaaaagg gtcagtctac ctcccgccat    1140
aaaaaactga tgttcaagac cgaaggtcct gactcagact ga                       1182
```

<210> SEQ ID NO 63
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 63

```
atggaagaac cacagtcaga tcctagcgtc gaaccacctc tgagtcagga aaccttttca      60
gacctgtgga aattgcttcc tgaaaacaac gttctgtccc cattgcctag tcaagcaatg     120
gatgatttga tgctgtcctc ggacgatatt gaacaatggt tcactgaaga tccaggccca     180
gatgaagctc cacgaatgcc agaggccgct ccacgcgttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagccctt aacaagatgt tttgccaact cgcgaagacc     420
tgcccagtcc aactgtgggt cgactccacc cctccacctg gtacacgtgt ccgcgcaatg     480
gccatctaca agcagagcca gcacatgacg gaggtcgtac gacgctgtcc acaccatgag     540
cgctgctcag attctgatgg tctggcgcca ccacagcatc ttatccgagt ggaaggtaac     600
ctacgcgtgg agtatctaga tgaccgcaac acttttcgac acagtgtggt ggtgccatat     660
gagccaccag aagttggctc tgactgcacc accatccact acaactatat gtgtaacagt     720
tcatgcatgg gcggcatgaa ccggcggccg atcctgacca tcatcactct cgaggattcc     780
tcaggtaatc tcctaggacg gaattccttt gaggtgcgtg tttgtgcatg cccgggccgc     840
```

```
gatcgccgga ccgaagagga gaatctccgg aagaaaggtg agcctcacca cgagctgcca    900
ccaggaagca ctaagcgagc actgccaaac aacaccagca gttctccaca gccaaagaag    960
aaacctttgg acgagaata tttcacccctt cagatccgtg gccgtgagcg gttcgagatg   1020
ttccgagagc tgaatgaggc cttagaactt aaggatgccc aggctggtaa ggagccagga   1080
ggcagccgtg ctcatagcag ccacctgaag tccaaaaagg gtcagtctac ctcccgccat   1140
aaaaaactga tgttcaagac cgaaggtcct gactcagact ga                      1182
```

<210> SEQ ID NO 64
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 64

```
atggaagaac cacagtcaga tcctagcgtc gaaccacctc tgagtcagga aaccttttca     60
gacctgtgga aattgcttcc tgaaaacaac gttctgtccc cattgcctag tcaagcaatg    120
gatgatttga tgctgtcctc ggacgatatt gaacaatggt tcactgaaga tccaggccca    180
gatgaagctc cacgaatgcc agaggccgct ccaccggttg ccccagcacc agcagctcct    240
acaccggcgg ccccagctcc ggccccatcc tggcctctgt catcttctgt cccttcccag    300
aaaacctacc aggcagcta cggtttccgt ctgggcttct tgcattctgg aactgccaag    360
tctgttactt gtacgtactc tccagccctt aacaagatgt tttgccaact cgcgaagacc    420
tgcccagtcc aactgtgggt cgactccacc cctccacctg gtacacgtgt ccgcgcaatg    480
gccatctaca agcagagcca gcacatgacg gaggtcgtac gacgctgtcc acaccatgag    540
cgctgctcag attctgatgg tctggcgcca ccacagcatc ttatccgagt ggaaggtaac    600
ctacgcgtgg agtatctaga tgaccgcaac acttttcgac acagtgtggt ggtgccatat    660
gagccaccag aagttggctc tgactgcacc accatccact acaactatat gtgtaacagt    720
tcatgcatgg gcggcatgaa ccggcggccg atcctgacca tcatcactct cgaggattcc    780
tcaggtaatc tcctaggacg gaattccttt gaggtgcgtg tttgtgcatg cccgggccgc    840
gatcgccgga ccgaagagga gaatctccgg aagaaaggtg agcctcacca cgagctgcca    900
ccaggaagca ctaagcgagc actgccaaac aacaccagca gttctccaca gccaaagaag    960
aaacctttgg acgagaata tttcacccctt cagatccgtg gccgtgagcg gttcgagatg   1020
ttccgagagc tgaatgaggc cttagaactt aaggatgccc aggctggtaa ggagccagga   1080
ggcagccgtg ctcatagcag ccacctgaag tccaaaaagg gtcagtctac ctcccgccat   1140
aaaaaactga tgttcaagac cgaaggtcct gactcagact ga                      1182
```

<210> SEQ ID NO 65
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 65

```
atggaagaac cacagtcaga tcctagcgtc gaaccacccc tgagtcagga aaccttttca     60
gatctgtgga agcttcttcc tgaaaacaac gttctgtccc cattgcctag tcaagcaatg    120
gatgatttga tgctgagccc agacgatatt gaacaatggt tcactgagga tccaggccca    180
```

```
gatgaagctc cacgaatgcc agaggccgct ccacgcgttg ccccagcacc agcagctcct      240
acaccggcgg ccccagctcc ggccccatcc tggcctctgt catcttctgt cccttcccag      300
aaaacctacc agggcagcta cggtttccgt ctgggcttct tgcattctgg aactgccaag      360
tctgttactt gtacgtactc tccagccctt aacaagatgt tttgccaact cgcgaagacc      420
tgcccagtcc aactgtgggt cgactccacc cctccacctg gtacacgtgt ccgcgcaatg      480
gccatctaca agcagagcca gcacatgacg gaggtcgtac gacgctgtcc acaccatgag      540
cgctgctcag attctgatgg tctggcgcca ccacagcatc ttatccgagt ggaaggtaac      600
ctacgcgtgg agtatctaga tgaccgcaac acttttcgac acagtgtggt ggtgccatat      660
gagccaccag aagttggctc tgactgcacc accatccact acaactatat gtgtaacagt      720
tcatgcatgg gcggcatgaa ccggcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaaggtg agcctcacca cgagctgcca      900
ccaggaagca ctaagcgagc actgccaaac aacaccagca gttctccaca gccaaagaag      960
aaacctttgg acgagaata tttcacccctt cagatccgtg gccgtgagcg gttcgagatg      1020
ttccgagagc tgaatgaggc cttagaactt aaggatgccc aggctggtaa ggagccagga      1080
ggcagccgtg ctcatagcag ccacctgaag tccaaaaagg gtcagtctac ctcccgccat      1140
aaaaaactga tgttcaagac cgaaggtcct gactcagact ga                       1182

<210> SEQ ID NO 66
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 66
atggaagaac cacagtcaga tcctagcgtc gaaccacccc tgagtcagga aaccttttca      60
gatctgtgga agcttcttcc tgaaaacaac gttctgtccc cattgcctag tcaagcaatg     120
gatgatttga tgctgagctc ggacgatatt gaacaatggt tcactgagga tccaggccca     180
gatgaagctc cacgaatgcc agaggccgct ccacgcgttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagccctt aacaagatgt tttgccaact cgcgaagacc     420
tgcccagtcc aactgtgggt cgactccacc cctccacctg gtacacgtgt ccgcgcaatg     480
gccatctaca agcagagcca gcacatgacg gaggtcgtac gacgctgtcc acaccatgag     540
cgctgctcag attctgatgg tctggcgcca ccacagcatc ttatccgagt ggaaggtaac     600
ctacgcgtgg agtatctaga tgaccgcaac acttttcgac acagtgtggt ggtgccatat     660
gagccaccag aagttggctc tgactgcacc accatccact acaactatat gtgtaacagt     720
tcatgcatgg gcggcatgaa ccggcggccg atcctgacca tcatcactct cgaggattcc     780
tcaggtaatc tcctaggacg gaattccttt gaggtgcgtg tttgtgcatg cccgggccgc     840
gatcgccgga ccgaagagga gaatctccgg aagaaaggtg agcctcacca cgagctgcca     900
ccaggaagca ctaagcgagc actgccaaac aacaccagca gttctccaca gccaaagaag     960
aaacctttgg acgagaata tttcacccctt cagatccgtg gccgtgagcg gttcgagatg      1020
ttccgagagc tgaatgaggc cttagaactt aaggatgccc aggctggtaa ggagccagga     1080
```

| ggcagccgtg ctcatagcag ccacctgaag tccaaaaagg gtcagtctac ctcccgccat | 1140 |
| aaaaaactga tgttcaagac cgaaggtcct gactcagact ga | 1182 |

<210> SEQ ID NO 67
<211> LENGTH: 1182
<212> TYPE: DNA
<213> ORGANISM: Artificial Sequence
<220> FEATURE:
<223> OTHER INFORMATION: Produced by genetic engineering

<400> SEQUENCE: 67

| atggaagaac cacagtcaga tcctagcgtc gaaccacccc tgagtcagga aaccttttca | 60 |
| gatctgtgga agcttcttcc tgaaaacaac gttctgtccc cattgcctag tcaagcaatg | 120 |
| gatgatttga tgctgagctc ggacgatatt gaacaatggt tcactgagga tccaggccca | 180 |
| gatgaagctc cacgaatgcc agaggccgct ccaccggttg ccccagcacc agcagctcct | 240 |
| acaccggcgg ccccagctcc ggccccatcc tggcctctgt catcttctgt cccttcccag | 300 |
| aaaacctacc aggcagcta cggtttccgt ctgggcttct tgcattctgg aactgccaag | 360 |
| tctgttactt gtacgtactc tccagccctt aacaagatgt tttgccaact cgcgaagacc | 420 |
| tgcccagtcc aactgtgggt cgactccacc cctccacctg gtacacgtgt ccgcgcaatg | 480 |
| gccatctaca gcagagcca gcacatgacg gaggtcgtac gacgctgtcc acaccatgag | 540 |
| cgctgctcag attctgatgg tctggcgcca ccacagcatc ttatccgagt ggaaggtaac | 600 |
| ctacgcgtgg agtatctaga tgaccgcaac acttttcgac acagtgtggt ggtgccatat | 660 |
| gagccaccag aagttggctc tgactgcacc accatccact acaactatat gtgtaacagt | 720 |
| tcatgcatgg gcggcatgaa ccggcggcg atcctgacca tcatcactct cgaggattcc | 780 |
| tcaggtaatc tcctaggacg gaattccttt gaggtgcgtg tttgtgcatg cccgggccgc | 840 |
| gatcgccgga ccgaagagga gaatctccgg aagaaaggtg agcctcacca cgagctgcca | 900 |
| ccaggaagca ctaagcgagc actgccaaac aacaccagca gttctccaca gccaaagaag | 960 |
| aaaccttttgg acgagaata tttcacccct cagatccgtg gccgtgagcg gttcgagatg | 1020 |
| ttccgagagc tgaatgaggc cttagaactt aaggatgccc aggctggtaa ggagccagga | 1080 |
| ggcagccgtg ctcatagcag ccacctgaag tccaaaaagg gtcagtctac ctcccgccat | 1140 |
| aaaaaactga tgttcaagac cgaaggtcct gactcagact ga | 1182 |

<210> SEQ ID NO 68
<211> LENGTH: 1181
<212> TYPE: DNA
<213> ORGANISM: Artificial Sequence
<220> FEATURE:
<223> OTHER INFORMATION: Produced by genetic engineering

<400> SEQUENCE: 68

| atggaagaac cacagtcaga tcctagcgtc gaaccacccc tgagtcagga aaccttttca | 60 |
| gatctgtgga agcttcttcc tgaaaacaac gttctgtccc cattgcctag tcaagcaatg | 120 |
| gatgatttga tgctgagccc agacgatatt gaacaatggt tcactgagga tccaggccca | 180 |
| gatgaagctc cacgaatgcc agaggccgct ccacgcgttg ccccagcacc agcagctcct | 240 |
| acaccggcgg ccccagctcc ggccccatcc tggcctctgt catcttctgt cccttcccag | 300 |
| aaaacctacc aggcagcta cggtttccgt ctgggcttct tgcattctgg aactgccaag | 360 |
| tctgttactt gtacgtactc tccagccctt aacaagatgt tttgccaact cgcgaagacc | 420 |

-continued

```
tgcccagtcc aactgtgggt cgactccacc cctccacctg gtacacgtgt ccgcgcaatg      480
gccatctaca agcagagcca gcacatgacg gaggtcgtac gacgctgtcc acaccatgag      540
cgctgctcag attctgatgg tctggcgcca ccacagcatc ttatccgagt ggaaggtaac      600
ctacgcgtgg agtatctaga tgaccgcaac acttttcgac acagtgtggt ggtgccatat      660
gagccaccag aagttggctc tgactgcacc accatccact acaactatat gtgtaacagt      720
tcatgcatgg gcggcatgaa ccggcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaaggtg agcctcacca cgagctgcca      900
ccaggaagca ctaagcgagc actgccaaac aacacgagct cttctccaca gccaaagaag      960 aaaccttttgg acgagaata tttcaccctg cagatccgtg gccgtgagcg gttcgagatg     1020
ttccgagagc tgaatgaggc cttagaactt aaggatgccc aggctggtaa ggagccagga     1080
ggcagccggg cccattcgtc tcacctgaag tccaaaaagg gtcagtctac tagtcgccat     1140
aaaaaactga gttcaagacc gaaggtcctg actcagactg a                        1181
```

<210> SEQ ID NO 69
<211> LENGTH: 1181
<212> TYPE: DNA
<213> ORGANISM: Artificial Sequence
<220> FEATURE:
<223> OTHER INFORMATION: Produced by genetic engineering

<400> SEQUENCE: 69

```
atggaagaac cacagtcaga tcctagcgtc gaaccacccc tgagtcagga aaccttttca       60
gatctgtgga agcttcttcc tgaaaacaac gttctgtccc cattgcctag tcaagcaatg      120
gatgatttga tgctgagctc ggacgatatt gaacaatggt tcactgagga tccaggccca      180
gatgaagctc cacagaatgc cagaggccgct ccacgcgttg ccccagcacc agcagctcct     240
acaccggcgg ccccagctcc ggccccatcc tggcctctgt catcttctgt cccttcccag      300
aaaacctacc agggcagcta cggtttccgt ctgggcttct tgcattctgg aactgccaag      360
tctgttactt gtacgtactc tccagccctt aacaagatgt tttgccaact cgcgaagacc      420
tgcccagtcc aactgtgggt cgactccacc cctccacctg gtacacgtgt ccgcgcaatg      480
gccatctaca agcagagcca gcacatgacg gaggtcgtac gacgctgtcc acaccatgag      540
cgctgctcag attctgatgg tctggcgcca ccacagcatc ttatccgagt ggaaggtaac      600
ctacgcgtgg agtatctaga tgaccgcaac acttttcgac acagtgtggt ggtgccatat      660
gagccaccag aagttggctc tgactgcacc accatccact acaactatat gtgtaacagt      720
tcatgcatgg gcggcatgaa ccggcggccg atcctgacca tcatcactct cgaggattcc      780
tcaggtaatc tcctaggacg gaattccttt gaggtgcgtg tttgtgcatg cccgggccgc      840
gatcgccgga ccgaagagga gaatctccgg aagaaaggtg agcctcacca cgagctgcca      900
ccaggaagca ctaagcgagc actgccaaac aacacgagct cttctccaca gccaaagaag      960 aaaccttttgg acgagaata tttcaccctg cagatccgtg gccgtgagcg gttcgagatg     1020
ttccgagagc tgaatgaggc cttagaactt aaggatgccc aggctggtaa ggagccagga     1080
ggcagccggg cccattcgtc tcacctgaag tccaaaaagg gtcagtctac tagtcgccat     1140
aaaaaactga gttcaagacc gaaggtcctg actcagactg a                        1181
```

<210> SEQ ID NO 70
<211> LENGTH: 1181

-continued

```
<212> TYPE: DNA
<213> ORGANISM: Artificial Sequence
<220> FEATURE:
<223> OTHER INFORMATION: Produced by genetic engineering

<400> SEQUENCE: 70
atggaagaac cacagtcaga tcctagcgtc gaaccacccc tgagtcagga aaccttttca      60
gatctgtgga agcttcttcc tgaaaacaac gttctgtccc cattgcctag tcaagcaatg     120
gatgatttga tgctgagccc agacgatatt gaacaatggt tcactgagga tccaggccca     180
gatgaagctc cacgaatgcc agaggccgct ccacgcgttg ccccagcacc agcagctcct     240
acaccggcgg ccccagctcc ggccccatcc tggcctctgt catcttctgt cccttcccag     300
aaaacctacc agggcagcta cggtttccgt ctgggcttct tgcattctgg aactgccaag     360
tctgttactt gtacgtactc tccagccctt aacaagatgt tttgccaact cgcgaagacc     420
tgcccagtcc aactgtgggt cgactccacc cctccacctg gtacacgtgt ccgcgcaatg     480
gccatctaca agcagagcca gcacatgacg gaggtcgtac gacgctgtcc acaccatgag     540
cgctgctcag attctgatgg tctggcgcca ccacagcatc ttatccgagt ggaaggtaac     600
ctacgcgtgg agtatctaga tgaccgcaac acttttcgac acagtgtggt ggtgccatat     660
gagccaccag aagttggctc tgactgcacc accatccact acaactatat gtgtaacagt     720
tcatgcatgg gcggcatgaa ccggcggccg atcctgacca tcatcactct cgaggattcc     780
tcaggtaatc tcctaggacg gaattccttt gaggtgcgtg tttgtgcatg cccgggccgc     840
gatcgccgga ccgaagagga gaatctccgg aagaaaggtg agcctcacca cgagctgcca     900
ccaggaagca ctaagcgagc actgccaaac aacacgagct cttctccaca gccaaagaag     960
aaacctttgg acgagaata  tttcacccctg cagatccgtg gccgtgagcg gttcgagatg    1020
ttccgagagc tgaatgaggc cttagaactt aaggatgccc aggctggtaa ggagccagga    1080
ggcagccggg cccattcgtc tcacctgaag tccaaaaagg gtcagtctac tagtcgccat    1140
aaaaaactga gttcaagacc gaaggtcctg actcagactg a                        1181

<210> SEQ ID NO 71
<211> LENGTH: 1179
<212> TYPE: DNA
<213> ORGANISM: Homo sapiens
<220> FEATURE:
<221> NAME/KEY: CDS
<222> LOCATION: (1)...(1179)
<221> NAME/KEY: misc_feature
<222> LOCATION: (1)...(1179)
<223> OTHER INFORMATION: n = A,T,C or G

<400> SEQUENCE: 71 atg gar gar ccn car nnn gay ccn nnn gtn gar ccn ccn ytn nnn car       48
Met Glu Glu Pro Gln Ser Asp Pro Ser Val Glu Pro Pro Leu Ser Gln
 1               5                  10                  15 gar acn tty nnn gay ytn tgg aar ytn ytn ccn gar aay aay gtn ytn       96
Glu Thr Phe Ser Asp Leu Trp Lys Leu Leu Pro Glu Asn Asn Val Leu
             20                  25                  30 nnn ccn ytn ccn nnn car gcn atg gay gay ytn atg ytn nnn ccn gay      144
Ser Pro Leu Pro Ser Gln Ala Met Asp Asp Leu Met Leu Ser Pro Asp
         35                  40                  45 gay ath gar car tgg tty acn gar gay ccn ggn ccn gay gar gcn ccn      192
Asp Ile Glu Gln Trp Phe Thr Glu Asp Pro Gly Pro Asp Glu Ala Pro
     50                  55                  60 nnn atg ccn gar gcn gcn ccn ccn gtn gcn ccn gcn ccn gcn gcn ccn      240
Arg Met Pro Glu Ala Ala Pro Pro Val Ala Pro Ala Pro Ala Ala Pro
```

```
                65                  70                  75                  80
acn ccn gcn gcn ccn gcn ccn gcn ccn nnn tgg ccn ytn nnn nnn nnn          288
Thr Pro Ala Ala Pro Ala Pro Ala Pro Ser Trp Pro Leu Ser Ser Ser
                    85                  90                  95 gtn ccn nnn car aar acn tay car ggn nnn tay ggn tty nnn ytn ggn          336
Val Pro Ser Gln Lys Thr Tyr Gln Gly Ser Tyr Gly Phe Arg Leu Gly
            100                 105                 110 tty ytn cay nnn ggn acn gcn aar nnn gtn acn tgy acn tay nnn ccn          384
Phe Leu His Ser Gly Thr Ala Lys Ser Val Thr Cys Thr Tyr Ser Pro
        115                 120                 125 gcn ytn aay aar atg tty tgy car ytn gcn aar acn tgy ccn gtn car          432
Ala Leu Asn Lys Met Phe Cys Gln Leu Ala Lys Thr Cys Pro Val Gln
    130                 135                 140 ytn tgg gtn gay nnn acn ccn ccn ggn acn nnn gtn nnn gcn atg              480
Leu Trp Val Asp Ser Thr Pro Pro Gly Thr Arg Val Arg Ala Met
145                 150                 155                 160 gcn ath tay aar car nnn car cay atg acn gar gtn gtn nnn nnn tgy          528
Ala Ile Tyr Lys Gln Ser Gln His Met Thr Glu Val Val Arg Arg Cys
                165                 170                 175 ccn cay cay gar nnn tgy nnn gay nnn gay ggn ytn gcn ccn ccn car          576
Pro His His Glu Arg Cys Ser Asp Ser Asp Gly Leu Ala Pro Pro Gln
            180                 185                 190 cay ytn ath nnn gtn gar ggn aay ytn nnn gtn gar tay ytn gay gay          624
His Leu Ile Arg Val Glu Gly Asn Leu Arg Val Glu Tyr Leu Asp Asp
        195                 200                 205 nnn aay acn tty nnn cay nnn gtn gtn gtn ccn tay gar ccn ccn gar          672
Arg Asn Thr Phe Arg His Ser Val Val Val Pro Tyr Glu Pro Pro Glu
    210                 215                 220 gtn ggn nnn gay tgy acn acn ath cay tay aay tay atg tgy aay nnn          720
Val Gly Ser Asp Cys Thr Thr Ile His Tyr Asn Tyr Met Cys Asn Ser
225                 230                 235                 240 nnn tgy atg ggn ggn atg aay nnn nnn ccn ath ytn acn ath ath acn          768
Ser Cys Met Gly Gly Met Asn Arg Arg Pro Ile Leu Thr Ile Ile Thr
                245                 250                 255 ytn gar gay nnn nnn ggn aay ytn ytn ggn nnn aay nnn tty gar gtn          816
Leu Glu Asp Ser Ser Gly Asn Leu Leu Gly Arg Asn Ser Phe Glu Val
            260                 265                 270 nnn gtn tgy gcn tgy ccn ggn nnn gay nnn nnn acn gar gar gar aay          864
Arg Val Cys Ala Cys Pro Gly Arg Asp Arg Arg Thr Glu Glu Glu Asn
        275                 280                 285 ytn nnn aar aar ggn gar ccn cay cay gar ytn ccn ccn ggn nnn acn          912
Leu Arg Lys Lys Gly Glu Pro His His Glu Leu Pro Pro Gly Ser Thr
    290                 295                 300 aar nnn gcn ytn ccn aay aay acn nnn nnn nnn ccn car ccn aar aar          960
Lys Arg Ala Leu Pro Asn Asn Thr Ser Ser Ser Pro Gln Pro Lys Lys
305                 310                 315                 320 aar ccn ytn gay ggn gar tay tty acn ytn car ath nnn ggn nnn gar         1008
Lys Pro Leu Asp Gly Glu Tyr Phe Thr Leu Gln Ile Arg Gly Arg Glu
                325                 330                 335 nnn tty gar atg tty nnn gar ytn aay gar gcn ytn gar ytn aar gay         1056
Arg Phe Glu Met Phe Arg Glu Leu Asn Glu Ala Leu Glu Leu Lys Asp
            340                 345                 350 gcn car gcn ggn aar gar ccn ggn ggn nnn nnn gcn cay nnn nnn cay         1104
Ala Gln Ala Gly Lys Glu Pro Gly Gly Ser Arg Ala His Ser Ser His
        355                 360                 365 ytn aar nnn aar aar ggn car nnn acn nnn nnn cay aar aar ytn atg         1152
Leu Lys Ser Lys Lys Gly Gln Ser Thr Ser Arg His Lys Lys Leu Met
    370                 375                 380 tty aar acn gar ggn ccn gay nnn gay                                     1179
Phe Lys Thr Glu Gly Pro Asp Ser Asp
```

-continued

```
Phe Lys Thr Glu Gly Pro Asp Ser Asp
385                 390
```